(12) United States Patent
Lu et al.

(10) Patent No.: US 11,446,332 B2
(45) Date of Patent: Sep. 20, 2022

(54) COMBINATORIAL CANCER IMMUNOTHERAPY

(71) Applicant: Senti Biosciences, Inc., South San Francisco, CA (US)

(72) Inventors: Timothy Kuan-Ta Lu, Cambridge, MA (US); Russell Morrison Gordley, San Francisco, CA (US); Jack Tzu-Chiao Lin, Redwood City, CA (US); Brian Scott Garrison, San Jose, CA (US); Philip Janmin Lee, Alameda, CA (US); Alba Gonzalez-Junca, San Francisco, CA (US); Don-Hong Wang, South San Francisco, CA (US)

(73) Assignee: SENTI BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 16/604,973

(22) PCT Filed: Apr. 13, 2018

(86) PCT No.: PCT/US2018/027492
§ 371 (c)(1),
(2) Date: Oct. 11, 2019

(87) PCT Pub. No.: WO2018/191619
PCT Pub. Date: Oct. 18, 2018

(65) Prior Publication Data
US 2020/0206271 A1 Jul. 2, 2020

Related U.S. Application Data

(60) Provisional application No. 62/583,343, filed on Nov. 8, 2017, provisional application No. 62/485,295, filed on Apr. 13, 2017.

(51) Int. Cl.
*A61K 35/28* (2015.01)
*A61P 35/00* (2006.01)
*A61K 39/395* (2006.01)
*A61K 39/00* (2006.01)

(52) U.S. Cl.
CPC .......... *A61K 35/28* (2013.01); *A61K 39/3955* (2013.01); *A61P 35/00* (2018.01); *A61K 2039/5156* (2013.01)

(58) Field of Classification Search
CPC .............. A61K 35/28; A61K 39/3955; A61K 2039/5156; A61K 38/195; A61K 38/208; A61K 38/215; A61K 38/217; A61K 39/395; A61P 35/00; C07K 16/2818; C12N 2510/00; C12N 15/63; C12N 5/0663; C12N 5/0636
See application file for complete search history.

(56) References Cited

U.S. PATENT DOCUMENTS

| | | |
|---|---|---|
| 4,965,195 A | 10/1990 | Namen et al. |
| 5,328,988 A | 7/1994 | Namen et al. |
| 5,486,359 A | 1/1996 | Caplan et al. |
| 5,536,657 A | 7/1996 | Chua et al. |
| 5,554,512 A | 9/1996 | Lyman et al. |
| 5,591,625 A | 1/1997 | Gerson et al. |
| 5,674,486 A | 10/1997 | Sobol et al. |
| 5,705,149 A | 1/1998 | Namen et al. |
| 5,780,268 A | 7/1998 | Coleman et al. |
| 5,827,735 A | 10/1998 | Young et al. |
| 5,965,122 A | 10/1999 | Namen et al. |
| 5,981,724 A | 11/1999 | Armitage et al. |
| 6,153,182 A | 11/2000 | Lillard, Jr. |
| 6,156,301 A | 12/2000 | Namen et al. |
| 6,187,307 B1 | 2/2001 | Cohen |
| 6,307,024 B1 | 10/2001 | Novak et al. |
| 6,361,997 B1 | 3/2002 | Huss |
| 6,392,126 B1 | 5/2002 | Mahajan |
| 6,632,424 B1 | 10/2003 | Lyman et al. |
| 6,686,178 B2 | 2/2004 | Novak et al. |
| 6,929,932 B2 | 8/2005 | Presnell et al. |
| 7,534,867 B1 | 5/2009 | Hannum et al. |
| 7,611,699 B2 | 11/2009 | Novak et al. |
| 7,833,754 B2 | 11/2010 | Felber et al. |
| 7,993,918 B2 | 8/2011 | Paludan et al. |
| 7,998,472 B2 | 11/2011 | Huss et al. |

(Continued)

FOREIGN PATENT DOCUMENTS

EP 1658853 A1 5/2006
JP 2011-507807 A 3/2011
(Continued)

OTHER PUBLICATIONS

Xu et al. "Bone marrow-derived mesenchymal stem cells co-expressing interleukin-18 and interferon-β exhibit potent antitumor effect against intracranial glioma in rats."Oncol Rep. Oct. 2015;34(4):1915-22. (Year: 2015).*
Reardon et al. "Glioblastoma Eradication Following Immune Checkpoint Blockade in an Orthotopic, Immunocompetent Model." Cancer Immunol Res. Feb. 2016;4(2):124-35 (Year: 2016).*
Shoji et al. "Local convection-enhanced delivery of an anti-CD40 agonistic monoclonal antibody induces antitumor effects in mouse glioma models."Neuro-Oncology 18(8), 1120-1128, 2016 (Year: 2016).*
Lesterhuis et al. "Synergistic effect of CTLA-4 blockade and cancer chemotherapy in the induction of anti-tumor immunity."PLoS One. Apr. 23, 2013;8(4):e61895. (Year: 2013).*

(Continued)

*Primary Examiner* — Titilayo Moloye
(74) *Attorney, Agent, or Firm* — Goodwin Procter LLP

(57) ABSTRACT

Provided herein are methods and compositions for dynamically controlling and targeting multiple immunosuppressive mechanisms in cancer. Some aspects provide cells engineered to produce multiple effector molecules, each of which modulates a different immunosuppressive mechanisms of a tumor, as well as methods of using the cells to treat cancer, such as ovarian, breast, or colon cancer.

18 Claims, 54 Drawing Sheets
Specification includes a Sequence Listing.

(56) References Cited

U.S. PATENT DOCUMENTS

| | | |
|---|---|---|
| 8,071,741 B2 | 12/2011 | Filpula et al. |
| 8,178,660 B2 | 5/2012 | Weiner et al. |
| 8,318,483 B2 | 11/2012 | Mistry et al. |
| 8,367,409 B2 | 2/2013 | Abbot et al. |
| 8,741,283 B2 | 6/2014 | Filpula et al. |
| 8,765,462 B2 | 7/2014 | Medin et al. |
| 9,198,938 B2 | 12/2015 | Abbot et al. |
| 9,303,080 B2 | 4/2016 | Felber et al. |
| 9,434,925 B2 | 9/2016 | Nelson |
| 9,487,800 B2 | 11/2016 | Schonfeld et al. |
| 9,492,482 B2 | 11/2016 | Beech et al. |
| 9,725,492 B2 | 8/2017 | Felber et al. |
| 9,790,261 B2 | 10/2017 | Felber et al. |
| 10,022,405 B2 | 7/2018 | Medin et al. |
| 10,046,049 B2 | 8/2018 | Beech et al. |
| 10,155,024 B2 | 12/2018 | Cho et al. |
| 10,201,592 B2 | 2/2019 | Wong et al. |
| 2001/0023070 A1 | 9/2001 | Ebner et al. |
| 2003/0003545 A1 | 1/2003 | Ebner et al. |
| 2004/0033217 A1 | 2/2004 | Vanguri et al. |
| 2004/0076622 A1 | 4/2004 | Studeny et al. |
| 2005/0037218 A1 | 2/2005 | Lottes et al. |
| 2005/0037306 A1 | 2/2005 | Nakatsu |
| 2006/0035373 A1* | 2/2006 | Zhang ................. C12N 5/0606 435/366 |
| 2007/0119895 A1 | 5/2007 | Pesch et al. |
| 2007/0149493 A1 | 6/2007 | Ross |
| 2008/0150368 A1 | 6/2008 | Gurcan |
| 2008/0253960 A1 | 10/2008 | Zheng et al. |
| 2009/0285805 A1 | 11/2009 | Grosveld et al. |
| 2010/0135958 A1 | 6/2010 | Hwu et al. |
| 2010/0255572 A1 | 10/2010 | Schmidt et al. |
| 2012/0051210 A1 | 3/2012 | Komatsu |
| 2014/0011881 A1 | 1/2014 | Shin et al. |
| 2014/0050709 A1 | 2/2014 | Leen et al. |
| 2014/0255363 A1 | 9/2014 | Metelitsa et al. |
| 2015/0035235 A1 | 2/2015 | Tsuda |
| 2015/0123183 A1 | 5/2015 | Kato et al. |
| 2015/0203820 A1 | 7/2015 | Wang et al. |
| 2016/0008435 A1 | 1/2016 | Cho et al. |
| 2016/0026854 A1 | 1/2016 | Hwang et al. |
| 2016/0146819 A1 | 5/2016 | Ince |
| 2016/0220612 A1 | 8/2016 | Mazzolini et al. |
| 2016/0237407 A1 | 8/2016 | Wagner et al. |
| 2017/0044227 A1 | 2/2017 | Schonfeld et al. |
| 2017/0128569 A1 | 5/2017 | Beech et al. |
| 2017/0133175 A1 | 5/2017 | Lin et al. |
| 2017/0133633 A1 | 5/2017 | Wang et al. |
| 2017/0142367 A1 | 5/2017 | Nakano et al. |
| 2017/0209492 A1 | 7/2017 | June et al. |
| 2017/0239297 A1 | 8/2017 | Gunther et al. |
| 2018/0044392 A1 | 2/2018 | Felber et al. |
| 2018/0071295 A1 | 3/2018 | Kuo et al. |
| 2018/0140686 A1 | 5/2018 | Varadarajan et al. |
| 2018/0160993 A9 | 6/2018 | Lee et al. |
| 2018/0161026 A1 | 6/2018 | Housman et al. |
| 2018/0161038 A1 | 6/2018 | Lorenzo |
| 2018/0162939 A1 | 6/2018 | Ma et al. |
| 2018/0170390 A1 | 6/2018 | Tatsushiro et al. |
| 2018/0191619 A1 | 7/2018 | Karthikeyan et al. |
| 2018/0213731 A1 | 8/2018 | Wykman et al. |
| 2019/0183977 A1 | 6/2019 | Wong et al. |
| 2020/0171093 A1 | 6/2020 | Lu et al. |
| 2021/0228640 A1 | 7/2021 | Lu et al. |

FOREIGN PATENT DOCUMENTS

| | | | |
|---|---|---|---|
| JP | 2015-523083 A | 8/2015 | |
| KR | 100788930 B1 | 12/2007 | |
| WO | WO-1995/027722 A1 | 10/1995 | |
| WO | WO-1998/017799 A1 | 4/1998 | |
| WO | WO-2005/037218 A2 | 4/2005 | |
| WO | WO-2005/037306 A1 | 4/2005 | |
| WO | WO-2007/119895 A1 | 10/2007 | |
| WO | WO-2007/149493 A2 | 12/2007 | |
| WO | WO-2008/150368 A1 | 12/2008 | |
| WO | WO-2012/051210 A2 | 4/2012 | |
| WO | WO-2014/011881 A2 | 1/2014 | |
| WO | WO-2015/035235 A1 | 3/2015 | |
| WO | WO-2015/123183 A1 | 8/2015 | |
| WO | WO-2016/026854 A2 | 2/2016 | |
| WO | WO-2016026854 A2 * | 2/2016 | ............ A61K 35/17 |
| WO | WO-2016/146819 A1 | 9/2016 | |
| WO | 2017/015427 A1 | 1/2017 | |
| WO | 2017/141181 A1 | 8/2017 | |
| WO | WO-2017/133175 A1 | 8/2017 | |
| WO | WO-2017/133633 A1 | 8/2017 | |
| WO | WO-2017/142367 A1 | 8/2017 | |
| WO | WO-2017/147383 A1 | 8/2017 | |
| WO | WO-2018/033254 A2 | 2/2018 | |
| WO | WO-2018/071295 A1 | 4/2018 | |
| WO | WO-2018/160993 A1 | 9/2018 | |
| WO | WO-2018/161026 A1 | 9/2018 | |
| WO | WO-2018/161038 A1 | 9/2018 | |
| WO | WO-2018/170390 A1 | 9/2018 | |
| WO | WO-2018/191619 A1 | 10/2018 | |
| WO | WO-2018/213731 A1 | 11/2018 | |
| WO | WO-2020/081869 A1 | 4/2020 | |

OTHER PUBLICATIONS

Zhou et al. "Expression of CD40 and growth-inhibitory activity of CD40 agonist in ovarian carcinoma cells." Cancer Immunol Immunother . Oct. 2012;61(10):1735-43 (Year: 2 012).*

Aalbers, C. et al., "Preclinical Potency and Biodistribution Studies on an AAV 5 Vector Expressing Human Interferon-[beta] (ART-102) for Local Treatment of Patients with Rheumatoid Arthritis", PLOS ONE, Jun. 24, 2015, vol. 10, No. 6, pp. 1-17.

Adams, S. et al., "Immunotherapy for ovarian cancer: what are the targets of the future?", Future Oncol. 2015;11(9):1293-1296. doi: 10.2217/fon.15.44.

Beegle, J. et al., "Preclinical evaluation of mesenchymal stem cells overexpressing VEGF to treat critical limb ischemia", Mol Ther Methods Clin Dev. Aug. 24, 2016;3:16053. doi: 10.1038/mtm.2016. 53. eCollection 2016.

Chen, F. et al., "IL10-transduced mesenchymal stem cells improve the acute graft-versus-host disease protection in a murine model", Blood (2007) 110 (11): 3242. Database Biosis, Biosciences Information Service, XP002781954, Database accession No. PREV200800218514.

Chen, X. et al., "A Tumor-selective Biotherapy With Prolonged Impact on Established Metastases Based on Cytokine Gene-engineered MSCs", Mol Ther. Apr. 2008;16(4):749-56. doi: 10.1038/mt.2008.3. Epub Feb. 5, 2008.

Choi, J.J. et al., "Mesenchymal stem cells overexpressing interleukin-10 attenuate collagen-induced arthritis in mice", Clinical and Experimental Immunology, Aug. 1, 2008, vol. 152, No. 2, pp. 269-276.

Cieri, N. et al., "IL-7 and IL-15 instruct the generation of human memory stem T cells from naive precursors", Blood. Jan. 24, 2013;121 (4):573-84. doi: 10.1182/blood-2012-05-431718. Epub Nov. 15, 2012.

Cruz, C. et al., "Adverse Events Following Infusion of T Cells for Adoptive Immunotherapy: A 10 Year Experience", Cytotherapy. Oct. 2010;12(6):743-9. doi: 10.3109/14653241003709686.

Dembinski, J. et al., "Tumor Stroma Engraftment of Gene-Modified Mesenchymal Stem Cells as Anti-Tumor Therapy against Ovarian Cancer", Cytotherapy. Jan. 2013;15(1):20-32. doi: 10.1016/j.jcyt. 2012.10.003.

Deng, P. et al., "Clinical trial perspective for adult and juvenile Huntington's disease using genetically-engineered mesenchymal stem cells",Neural Regen Res. May 2016;11(5):702-5. doi: 10.4103/1673-5374.182682.

Dominici, M. et al., "Minimal criteria for defining multipotent mesenchymal stromal cells. The International Society for Cellular Therapy position statement", Cytotherapy. 2006;8(4):315-7.

Dubinett, S. et al., "Chemokines: Can Effector Cells be Re-directed to the Site of Tumor?", Cancer J. Jul.-Aug. 2010;16(4):325-35. doi: 10.1097/PPO.0b013e3181eb33bc.

(56) References Cited

OTHER PUBLICATIONS

Gao, P. et al., Therapeutic potential of human mesenchymal stem cells producing IL-12 in a mouse xenograft model of renal cell carcinoma et al., Cancer Letters 290 (2010) 157-166.

Gilham, D. et al., "CAR-T cells and solid tumors: tuning T cells to challenge an inveterate foe", Trends Mol Med. Jul. 2012;18(7):377-84. doi: 10.1016/j.molmed.2012.04.009. Epub May 19, 2012.

Hamanishi J. et al., "Immune checkpoint inhibition in ovarian cancer", Int Immunol. Jul. 2016;28(7):339-48. doi: 10.1093/intimm/dxw020. Epub Apr. 7, 2016.

Hu, Y.L. et al., "Mesenchymal stem cells: A promising targeted-delivery vehicle in cancer gene therapy", J Control Release, 147 (2), 154-62 Oct. 15, 2010.

Kidd, S. et al., "Direct Evidence of Mesenchymal Stem Cell Tropism for Tumor and Wounding Microenvironments using In Vivo Bioluminescence Imaging", Stem Cells. Oct. 2009;27(10):2614-23. doi 10.1002/stem.187.

Koneru, M. et al., "A phase I clinical trial of adoptive T cell therapy using IL-12 secreting MUC-16ecto directed chimeric antigen receptors for recurrent ovarian cancer", J Transl Med. Mar. 28, 2015;13:102. doi 10.1186/s12967-015-0460-x.

Lengyel, E., "Ovarian Cancer Development and Metastasis", Am J Pathol. Sep. 2010;177(3):1053-64. doi: 10.2353/ajpath.2010.100105. Epub Jul. 22, 2010.

Li, S. et al., "Oncolytic virotherapy for ovarian cancer", Oncolytic Virother. Aug. 2012;1:1-21.

Li, Y.Q. et al., "Tumor Secretion of CCL22 Activates Intratumoral Treg Infiltration and Is Independent Prognostic Predictor of Breast Cancer", PLoS One. Oct. 4, 2013;8(10):e76379. doi: 10.1371/journal.pone.0076379. eCollection 2013.

Ling, X. et al., "Mesenchymal Stem Cells Overexpressing IFN-β Inhibit Breast Cancer Growth and Metastases through Stat3 Signaling in a Syngeneic Tumor Model", Cancer Microenviron. Mar. 19, 2010;3(1):83-95. doi: 10.1007/s12307-010-0041-8.

Marofi, F. et al., "Mesenchymal Stromal/Stem Cells: A New Era in the Cell-Based Targeted Gene Therapy of Cancer", Front Immunol. Dec. 18, 2017;8:1770. doi: 10.3389/fimmu.2017.01770. eCollection 2017.

Martin, I. et al., "Challenges for mesenchymal stromal cell therapies", Sci Transl Med. Feb. 20, 2019;11(480). pii: eaat2189. doi: 10.1126/scitranslmed.aat2189.

Mirzaei, H. et al., "Application of Mesenchymal Stem Cells in Melanoma: A Potential Therapeutic Strategy for Delivery of Targeted Agents", Current Medicinal Chemistry, Jan. 1, 2016, pp. 455-463.

Mohammadi, M. et al., "Mesenchymal stem cell: a new horizon in cancer gene therapy", Cancer Gene Ther. Sep. 2016;23(9):285-6. doi: 10.1038/cgt.2016.35. Epub Aug. 19, 2016.

Nowakowski, A. et al., "Genetic Engineering of Mesenchymal Stem Cells to Induce Their Migration and Survival", Stem Cells Int. 2016;2016:4956063. doi: 10.1155/2016/4956063. Epub May 3, 2016.

Parker, B. et al., "Antitumour actions of interferons: implications for cancer therapy", Nat Rev Cancer. Mar. 2016;16(3):131-44. doi: 10.1038/nrc.2016.14.

PCT International Search Report and Written Opinion, PCT Application No. PCT/US2018/027492, dated Aug. 10, 2018, 17 pages.

PCT International Search Report, PCT Application No. PCT/US2018/022855, dated Jul. 2, 2018, 4 pages.

Schukur, L. et al., "Implantable synthetic cytokine converter cells with AND-gate logic treat experimental psoriasis", Sci Transl Med. Dec. 16, 2015;7(318):318ra201. doi: 10.1126/scitranslmed.aac4964.

Sharma, A. et al., "High Throughput Characterization of Adult Stem Cells Engineered for Delivery of Therapeutic Factors for Neuroprotective Strategies", J Vis Exp. Jan. 4, 2015;(95):e52242. doi 10.3791/52242.

Shi, Yufang, et al., "Tumour-associated mesenchymal stem/stromal cells: emerging therapeutic targets", Nature Reviews, Drug Discovery, Nov. 4, 2016, vol. 16, No. 1, pp. 35-52.

Squillaro, T. et al., "Clinical Trials With Mesenchymal Stem Cells: An Update", Cell Transplant. 2016;25(5):829-48. doi: 10.3727/096368915X689622. Epub Sep. 29, 2015.

Studeny, M. et al., "Mesenchymal Stem Cells: Potential Precursors for Tumor Stroma and Targeted-Delivery Vehicles for Anticancer Agents", J Natl Cancer Inst. Nov. 3, 2004;96(21):1593-603.

Sun, Z. et al., "The roles of mesenchymal stem cells in tumor inflammatory microenvironment", J Hematol Oncol. Feb. 6, 2014;7:14. doi: 10.1186/1756-8722-7-14.

Wang D. et al., "Allogeneic Mesenchymal Stem Cell Transplantation in Severe and Refractory Systemic Lupus Erythematosus: 4 Years of Experience", Cell Transplant. 2013;22(12):2267-77. doi 10.3727/096368911X582769c.

Wang, H. et al., "Genetically engineered bone marrow-derived mesenchymal stem cells co-expressing IFN-[gamma] and IL-10 inhibit hepatocellular carcinoma by modulating MAPK pathway", Journal of B.U.ON.: official journal of the Balkan Union of Oncology, Nov. 1, 2017, pp. 1517-1524.

Wang, V. et al., "The Transcriptional Specificity of NF-kappa β Dimers is Coded within the kappa βDNA Response Elements", Cell Reports, Oct. 2012, vol. 2, No. 4, pp. 824-839.

Waterman, R. et al., "Mesenchymal Stem Cell 1 (MSC1)-Based Therapy Attenuates Tumor Growth Whereas MSC2-Treatment Promotes Tumor Growth and Metastasis", PLoS One. 2012;7(9):e45590. doi: 10.1371/journal.pone.0045590. Epub Sep. 20, 2012.

Wiedemann, G. et al., "Cancer cell-derived IL-1a induces CCL22 and the recruitment of regulatory T cells", Oncoimmunology. Apr. 25, 2016;5(9):e1175794. eCollection 2016.

Woo, S.R. et al., "The STING pathway and the T cell-inflamed tumor Microenvironment", (2015) Trends Immunol. Apr. 2015;36(4):250-6. doi: 10.1016/j.it.2015.02.003. Epub Mar. 7, 2015.

Xie, C. et al., "Interferon-b gene-modified human bone marrow mesenchymal stem cells attenuate hepatocellular carcinoma through inhibiting AKT/FOX03a pathway", Br J Cancer. Sep. 3, 2013;109(5):1198-205. doi: 10.1038/bjc.2013.422. Epub Jul. 25, 2013.

Xishan, Z. et al., "Mouse Flk-1+Sca-1-Mesenchymal Stem Cells: Functional Plasticity In Vitro and Immunoregulation In Vivo", Transplantation, Mar. 15, 2014, vol. 97, No. 5, pp. 509-517.

Xu, G. et al., "Bone marrow-derived mesenchymal stem cells co-expressing interleukin-18 and interferon-[beta] exhibit potent antitumor effect against intracranial glioma in rats", Oncology Reports, Aug. 5, 2015, vol. 34, No. 4, pp. 1915-1922.

Zhang, Y. et al., "Gene therapy of ovarian cancer using IL-21—secreting human umbilical cord mesenchymal stem cells in nude mice", J Ovarian Res. Jan. 20, 2014;7:8. doi: 10.1186/1757-2215-7-8.

Zhao, Q. et al., "MSCs derived from iPSCs with a modified protocol are tumor-tropic but have much less potential to promote tumors than bone marrow MSCs", Proc Natl Acad Sci USA. Jan. 13, 2015;112(2):530-5. doi: 10.1073/pnas.1423008112. Epub Dec. 29, 2014.

Zhao, R. et al., "Mechanisms of and perspectives on the mesenchymal stem cell in immunotherapy", J Lab Clin Med. May 2004;143(5):284-91.

PCT International Search Report and Written Opinion, PCT Application No. PCT/US2019/056824, dated Apr. 23, 2020, 12 pages.

Roby et al., "Development of a syngeneic mouse model for events related to ovarian cancer." Carcinogenesis 21, No. 4 (2000): 585-591.

PCT/US2018/027492—International Preliminary Report on Patentability, dated Oct. 15, 2019, 8 pages.

Batra et al. "Armored Glypican-3-Specific CART Cells for the Immunotherapy of Hepatocellular Carcinoma." ASGCT 2018, May 2018 (May 1, 2018). Cell Technology . (Year: 2018).

Jayaraman et al., "CAR-T design: Elements and their synergistic function." EBioMedicine 58 (2020): 102931.

Labanieh et al., "Programming CAR-T cells to kill cancer." Nature biomedical engineering 2, No. 6 (2018): 377-391.

Li et al., "Strategies to improve the migration of mesenchymal stromal cells in cell therapy." Translational Neuroscience and Clinics 3, No. 3 (2017): 159-175.

(56) References Cited

OTHER PUBLICATIONS

Kimura et al., "Tumor-homing effect of human mesenchymal stem cells in a TH-MYCN mouse model of neuroblastoma." Journal of pediatric surgery 51, No. 12 (2016): 2068-2073.
Uchibori et al., "Cancer gene therapy using mesenchymal stem cells " International journal of hematology 99, No. 4 (2014): 377-382.
Bernardo et al., "Mesenchymal stromal cell therapy: a revolution in Regenerative Medicine?" Bone marrow transplantation 47, No. 2 (2012): 164-171.
Nayyar et al., "Overcoming resistance to natural killer cell based immunotherapies for solid tumors." Frontiers in oncology 9 (2019): 51.
Okuda et al., "Postischemic intraventricular administration of FGF-2-expressing adenoviral vectors improves neurological outcome and reduces infarct volume after permanent focal cerebral ischemia in rats." Bulletin of the Osaka Medical College 53, No. 2 (2007): 133-141.
Patel et al., "Linkers: a synergistic way for chimeric proteins." Authorea Preprints (2020).
Wahed el al., 'Recombinase polymerase amplification assay for rapid diagnostics of Dengue infection.' PLoS One 10, No. 6 (2015): 1-17.

\* cited by examiner

FIG. 19

```
                         SEQUENCE LISTING

<160> NUMBER OF SEQ ID NOS: 9

<210> SEQ ID NO 1
<211> LENGTH: 588
<212> TYPE: DNA
<213> ORGANISM: Artificial Sequence
<220> FEATURE:
<223> OTHER INFORMATION: Synthetic polynucleotide

<400> SEQUENCE: 1
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctc                  588

<210> SEQ ID NO 2
<211> LENGTH: 544
<212> TYPE: DNA
<213> ORGANISM: Artificial Sequence
<220> FEATURE:
<223> OTHER INFORMATION: Synthetic polynucleotide

<400> SEQUENCE: 2
ggatctgcga tcgctccggt gcccgtcagt gggcagagcg cacatcgccc acagtccccg      60
agaagttggg gggagggtc ggcaattgaa ccggtgccta gagaaggtgg cgcgggtaa       120 actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct tcgagggggct cgcatctctc cttcacgcgc ccgccgccct acctgaggcc     300
```

```
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctac                                                                 544

<210> SEQ ID NO 3
<211> LENGTH: 399
<212> TYPE: DNA
<213> ORGANISM: Artificial Sequence
<220> FEATURE:
<223> OTHER INFORMATION: Synthetic polynucleotide

<400> SEQUENCE: 3
tttatttagt ctccagaaaa aggggggaat gaaagacccc acctgtaggt ttggcaagct     60
aggatcaagg ttaggaacag agagacagca gaatatgggc caaacaggat atctgtggta    120
agcagttcct gccccggctc agggccaaga acagttggaa cagcagaata tgggccaaac    180
aggatatctg tggtaagcag ttcctgcccc ggctcagggc caagaacaga tggtccccag    240
atgcggtccc gccctcagca gtttctagag aaccatcaga tgtttccagg gtgccccaag    300
gacctgaaat gaccctgtgc cttatttgaa ctaaccaatc agttcgcttc tcgttctgt    360 tcgcgcgctt ctgctccccg agctcaataa aagagccca                          399

<210> SEQ ID NO 4
<211> LENGTH: 511
<212> TYPE: DNA
<213> ORGANISM: Artificial Sequence
<220> FEATURE:
<223> OTHER INFORMATION: Synthetic polynucleotide

<400> SEQUENCE: 4
ggggttgggg ttgcgccttt tccaaggcag ccctgggttt gcgcagggac gcggctgctc     60
tgggcgtggt tccgggaaac gcagcggcgc cgaccctggg tctcgcacat tcttcacgtc    120
cgttcgcagc gtcacccgga tcttcgccgc taccttgtg ggcccccggc cgacgcttcc    180
tgctccgccc ctaagtcggg aaggttcctt gcggttcgcg gcgtgccgga cgtgacaaac    240
ggaagccgca cgtctcacta gtaccctcgc agacggacag cgccagggag caatggcagc    300
gcgccgaccg cgatgggctg tggccaatag cggctgctca gcggggcgcg ccgagagcag    360
cggccgggaa ggggcggtgc gggaggcggg gtgtggggcg gtagtgtggg ccctgttcct    420
gcccgcgcgg tgttccgcat tctgcaagcc tccggagcgc acgtcggcag tcggctccct    480
cgttgaccga atcaccgacc tctctcccca g                                   511

<210> SEQ ID NO 5
<211> LENGTH: 408
<212> TYPE: DNA
<213> ORGANISM: Artificial Sequence
<220> FEATURE:
<223> OTHER INFORMATION: Synthetic polynucleotide

<400> SEQUENCE: 5
gtaacgccat tttgcaaggc atggaaaaat accaaaccaa gaatagagaa gttcagatca     60
agggcgggta catgaaaata gctaacgttg ggccaaacag gatatctgcg gtgagcagtt    120
tcggccccgg cccggggcca agaacagatg gtcaccgcag tttcggcccc ggcccgaggc    180
```

```
caagaacaga tggtccccag atatggccca accctcagca gtttcttaag acccatcaga      240
tgtttccagg ctccccaag gacctgaaat gaccctgcgc cttatttgaa ttaaccaatc      300
agcctgcttc tcgcttctgt tcgcgcgctt ctgcttcccg agctctataa aagagctcac      360
aacccctcac tcggcgcgcc agtcctccga cagactgagt cgcccggg                  408

<210> SEQ ID NO 6
<211> LENGTH: 344
<212> TYPE: DNA
<213> ORGANISM: Artificial Sequence
<220> FEATURE:
<223> OTHER INFORMATION: Synthetic polynucleotide

<400> SEQUENCE: 6
ctgtggaatg tgtgtcagtt agggtgtgga aagtccccag gctccccagc aggcagaagt       60
atgcaaagca tgcatctcaa ttagtcagca accaggtgtg aaagtcccc aggctcccca      120 gcaggcagaa gtatgcaaag catgcatctc aattagtcag caaccatagt cccgccccta      180
actccgccca tcccgcccct aactccgccc agttccgccc attctccgcc ccatggctga      240
ctaatttttt ttatttatgc agaggccgag gccgcctctg cctctgagct attccagaag      300
tagtgaggag gctttttggg aggcctaggc ttttgcaaaa agct                      344

<210> SEQ ID NO 7
<211> LENGTH: 1229
<212> TYPE: DNA
<213> ORGANISM: Artificial Sequence
<220> FEATURE:
<223> OTHER INFORMATION: Synthetic polynucleotide

<400> SEQUENCE: 7
gcgccgggtt ttggcgcctc ccgcgggcgc cccctcctc acggcgagcg ctgccacgtc        60
agacgaaggg cgcaggagcg ttcctgatcc ttccgcccgg acgctcagga cagcggcccg      120
ctgctcataa gactcggcct tagaaccccca gtatcagcag aaggacattt taggacggga      180
cttgggtgac tctagggcac tggttttctt tccagagagc ggaacaggcg aggaaaagta      240
gtcccttctc ggcgattctg cggagggatc tccgtggggc ggtgaacgcc gatgattata      300
taaggacgcg ccgggtgtgg cacagctagt tccgtcgcag ccgggatttg ggtcgcggtt      360
cttgtttgtg gatcgctgtg atcgtcactt ggtgagttgc gggctgctgg gctgccggg      420 gctttcgtgg ccgccgggcc gctcggtggg acggaagcgt gtggagagac cgccaagggc      480
tgtagtctgg gtccgcgagc aaggttgccc tgaactgggg gttgggggga gcgcacaaaa      540
tggcggctgt tcccgagtct tgaatggaag acgcttgtaa ggcgggctgt gaggtcgttg      600
aaacaaggtg gggggcatgg tgggcggcaa gaacccaagg tcttgaggcc ttcgctaatg      660
cgggaaagct cttattcggg tgagatgggc tgggcacca tctgggacc ctgacgtgaa       720 gtttgtcact gactggagaa ctcgggtttg tcgtctggtt gcggggcgg cagttatgcg       780 gtgccgttgg gcagtgcacc cgtacctttg ggagcgcgcg cctcgtcgtg tcgtgacgtc      840
acccgttctg ttggcttata atgcagggtg gggccacctg ccggtaggtg tgcggtaggc      900
ttttctccgt cgcaggacgc agggttcggg cctaggtag gctctcctga atcgacaggc      960
gccggacctc tggtgagggg aggataagt gaggcgtcag ttctctggt cggttttag      1020 tacctatctt cttaagtagc tgaagctccg gttttgaact atgcgctcgg ggttggcgag     1080
tgtgttttgt gaagtttttt aggcaccttt tgaaatgtaa tcatttggt caatatgtaa      1140 ttttcagtgt tagactagta aagcttctgc aggtcgactc tagaaaattg tccgctaaat     1200
```
tctggccgtt tttggctttt ttgttagac                                     1229

<210> SEQ ID NO 8
<211> LENGTH: 6029
<212> TYPE: DNA
<213> ORGANISM: Artificial Sequence
<220> FEATURE:
<223> OTHER INFORMATION: Synthetic polynucleotide

<400> SEQUENCE: 8
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata aacgggtctc     240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agaccctttt agtcagtgtg gaaaatctct agcagtggcg     420
cccgaacagg gacctgaaag cgaaagggaa accagagctc tctcgacgca ggactcggct     480
tgctgaagcg cgcacggcaa gaggcgaggg gcggcgactg gtgagtacgc caaaaatttt     540
gactagcgga ggctagaagg agagagatgg gtgcgagagc gtcagtatta agcggggggag     600
aattagatcg cgatgggaaa aaattcggtt aaggccaggg ggaaagaaaa aatataaatt     660
aaaacatata gtatgggcaa gcaggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aaagacacca aggaagcttt agacaagata gaggaagagc aaaacaaaag     900
taagaccacc gcacagcaag cggccactga tcttcagacc tggaggagga gatatgaggg     960
acaattggag aagtgaatta tataaatata agtagtaaa aattgaacca ttaggagtag    1020
cacccaccaa ggcaaagaga agagtggtgc agagagaaaa aagagcagtg gaataggag     1080
cttttgttcct tgggttcttg ggagcagcag gaagcactat gggcgcagcc tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg gaaagatacc taaaggatca acagctcctg gggatttggg    1320
gttgctctgg aaaactcatt tgcaccactg ctgtgccttg gaatgctagt tggagtaata    1380
aatctctgga acagattgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta cataacaaa    1560
ttggctgtgg tatataaaat tattcataat gatagtagga ggcttggtag gtttaagaat    1620
agttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggtt    1800
aactttttaaa agaaaagggg ggattggggg gtacagtgca ggggaaagaa tagtagacat    1860
aatagcaaca gacatacaaa ctaaagaatt acaaaaacaa attacaaaaa tcaaaatttt    1920
atctcgacat ggtggcgacc ggtagcgcta gcggatcgat aagcttgata tcgcctgcag    1980

```
ccgaattcct tgacttggga tccgcgtcaa gtggagcaag gcaggtggac agtcctgcag    2040
gcatgcgtga ctgactgagg ccgcgactct agtttaaact gcgtgactga ctctagaaga    2100
tccggcagtg cggccgcgtc gacaatcaac ctctggatta caaaatttgt gaaagattga    2160
ctggtattct taactatgtt gctccttttq cgctatgtgg atacgctgct ttaatgcctt    2220
tgtatcatgc tattgcttcc cgtatggctt tcattttctc ctccttgtat aaatcctggt    2280
tgctgtctct ttatgaggag ttgtggcccg ttgtcaggca acgtggcgtg gtgtgcactg    2340
tgtttgctga cgcaaccccc actggttggg gcattgccac cacctgtcag ctcctttccg    2400
ggactttcgc tttccccctc cctattgcca cggcggaact catcgccgcc tgccttgccc    2460
gctgctggac aggggctcgg ctgttgggca ctgacaattc cgtggtgttg tcggggaaat    2520
catcgtcctt ccttggctg ctcgcctgtg ttgccacctg gattctgcgc gggacgtcct    2580
tctgctacgt ccccttcggcc ctcaatccag cggaccttcc ttcccgcggc ctgctgccgg    2640
ctctgcggcc tcttccgcgt cttcgccttc gccctcagac gagtcggatc tccctttggg    2700
ccgcctcccc gcctggtacc tttaagacca atgacttaca aggcagctgt agatcttagc    2760 cacttttta aagaaaaggg gggactggaa gggctaattc actcccaacg aaaataagat    2820
ctgctttttg cttgtactgg gtctctctgg ttagaccaga tctgagcctg ggagctctct    2880
ggctaactag ggaacccact gcttaagcct caataaagct tgccttgagt gcttcaagta    2940
gtgtgtgccc gtctgttgtg tgactctggt aactagagat ccctcagacc cttttagtca    3000
gtgtggaaaa tctctagcag tagtagttca tgtcatctta ttattcagta tttataactt    3060
gcaaagaaat gaatatcaga gagtgagagg aacttgttta ttgcagctta taatggttac    3120
aaataaagca atagcatcac aaatttcaca aataaagcat ttttttcact gcattctagt    3180
tgtggtttgt ccaaactcat caatgtatct tatcatgtct ggctctagct atcccgcccc    3240
taactccgcc cagttccgcc cattctccgc cccatggctg actaatttt tttatttatg    3300 cagaggccga ggccgcctcg gcctctgagc tattccagaa gtagtgagga ggcttttttg    3360
gaggcctaga cttttgcaga cacggcccaa attcgtaatc atggtcatag ctgtttcctg    3420
tgtgaaattg ttatccgctc acaattccac acaacatacg agccgaagc ataaagtgta    3480 aagcctgggg tgcctaatga gtgagctaac tcacattaat tgcgttgcgc tcactgcccg    3540
ctttccagtc gggaaacctg tcgtgccagc tgcattaatg aatcggccaa cgcgcgggga    3600
gaggcggttt gcgtattggg cgctcttccg cttcctcgct cactgactcg ctgcgctcgg    3660
tcgttcggct gcggcgagcg gtatcagctc actcaaaggc ggtaatacgg ttatccacag    3720
aatcagggga taacgcagga aagaacatgt gagcaaaagg ccagcaaaag gccaggaacc    3780
gtaaaaaggc cgcgttgctg gcgttttcc ataggctccg ccccctgac gagcatcaca    3840 aaaatcgacg ctcaagtcag aggtggcgaa acccgacagg actataaaga taccaggcgt    3900
ttccccctgg aagctccctc gtgcgctctc ctgttccgac cctgccgctt accggatacc    3960
tgtccgcctt tctcccttcg ggaagcgtgg cgctttctca tagctcacgc tgtaggtatc    4020
tcagttcggt gtaggtcgtt cgctccaagc tgggctgtgt gcacgaaccc cccgttcagc    4080
ccgaccgctg cgccttatcc ggtaactatc gtcttgagtc aacccggta agacacgact    4140 tatcgccact ggcagcagcc actggtaaca ggattagcag agcgaggtat gtaggcggtg    4200
ctacagagtt cttgaagtgg tggcctaact acggctacac tagaaggaca gtatttggta    4260
tctgcgctct gctgaagcca gttaccttcg gaaaaagagt tggtagctct tgatccggca    4320
aacaaaccac cgctggtagc ggtggttttt tgtttgcaa gcagcagatt acgcgcagaa    4380
```

```
aaaaaggatc tcaagaagat cctttgatct tttctacggg gtctgacgct cagtggaacg    4440
aaaactcacg ttaagggatt ttggtcatga gattatcaaa aaggatcttc acctagatcc    4500
ttttaaatta aaaatgaagt tttaaatcaa tctaaagtat atatgagtaa acttggtctg    4560
acagttacca atgcttaatc agtgaggcac ctatctcagc gatctgtcta tttcgttcat    4620
ccatagttgc ctgactcccc gtcgtgtaga taactacgat acgggagggc ttaccatctg    4680
gccccagtgc tgcaatgata ccgcgagacc cacgctcacc ggctccagat ttatcagcaa    4740
taaaccagcc agccggaagg gccgagcgca gaagtggtcc tgcaacttta tccgcctcca    4800
tccagtctat taattgttgc cgggaagcta gagtaagtag ttcgccagtt aatagtttgc    4860
gcaacgttgt tgccattgct acaggcatcg tggtgtcacg ctcgtcgttt ggtatggctt    4920
cattcagctc cggttcccaa cgatcaaggc gagttacatg atcccccatg ttgtgcaaaa    4980
aagcggttag ctccttcggt cctccgatcg ttgtcagaag taagttggcc gcagtgttat    5040
cactcatggt tatggcagca ctgcataatt ctcttactgt catgccatcc gtaagatgct    5100
tttctgtgac tggtgagtac tcaaccaagt cattctgaga atagtgtatg cggcgaccga    5160
gttgctcttg cccggcgtca atacgggata ataccgcgcc acatagcaga actttaaaag    5220
tgctcatcat tggaaaacgt tcttcggggc gaaaactctc aaggatctta ccgctgttga    5280
gatccagttc gatgtaaccc actcgtgcac ccaactgatc ttcagcatct tttactttca    5340
ccagcgtttc tgggtgagca aaaacaggaa ggcaaaatgc cgcaaaaaag ggaataaggg    5400
cgacacggaa atgttgaata ctcatactct tcctttttca atattattga agcatttatc    5460
agggttattg tctcatgagc ggatacatat ttgaatgtat ttagaaaaat aaacaaatag    5520
gggttccgcg cacatttccc cgaaaagtgc cacctgacgt ctaagaaacc attattatca    5580
tgacattaac ctataaaaat aggcgtatca cgaggccctt tcgtctcgcg cgtttcggtg    5640
atgacggtga aaacctctga cacatgcagc tcccggagac ggtcacagct tgtctgtaag    5700
cggatgccgg gagcagacaa gcccgtcagg gcgcgtcagc gggtgttggc gggtgtcggg    5760
gctggcttaa ctatgcggca tcagagcaga ttgtactgag agtgcaccat atgcggtgtg    5820
aaataccgca cagatgcgta aggagaaaat accgcatcag gcgccattcg ccattcaggc    5880
tgcgcaactg ttgggaaggg cgatcggtgc gggcctcttc gctattacgc cagctggcga    5940
aagggggatg tgctgcaagg cgattaagtt gggtaacgcc agggttttcc cagtcacgac    6000
gttgtaaaac gacggccagt gccaagctg                                      6029

<210> SEQ ID NO 9
<211> LENGTH: 1179
<212> TYPE: DNA
<213> ORGANISM: Artificial Sequence
<220> FEATURE:
<223> OTHER INFORMATION: Synthetic polynucleotide

<400> SEQUENCE: 9
ggctccggtg cccgtcagtg ggcagagcgc acatcgccca cagtccccga gaagttgggg     60
ggaggggtcg gcaattgaac cggtgcctag agaaggtggc gcggggtaaa ctgggaaagt    120
gatgccgtgt actggctccg ccttttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccacct ggctgcagta cgtgattctt gatcccgagc ttcgggttgg aagtgggtgg    360
```

```
gagagttcga ggccttgcgc ttaaggagcc ccttcgcctc gtgcttgagt tgaggcctgg    420
cctgggcgct ggggccgccg cgtgcgaatc tggtggcacc ttcgcgcctg tctcgctgct    480
ttcgataagt ctctagccat ttaaaatttt tgatgacctg ctgcgacgct ttttttctgg    540
caagatagtc ttgtaaatgc gggccaagat ctgcacactg gtatttcggt ttttggggcc    600 gcggcggcg  acggggcccg tgcgtcccag cgcacatgtt cggcgaggcg gggcctgcga    660
gcgcgaccac cgagaatcgg acggggtag  tctcaagctg gccggcctgc tctggtgcct    720
gtcctcgcgc cgccgtgtat cgccccgccc cgggcggcaa ggctggcccg gtcggcacca    780
gttgcgtgag cggaaagatg gccgcttccc ggtcctgctg cagggagctc aaaatggagg    840
acgcggcgct cgggagagcg ggcgggtgag tcacccacac aaaggaaaag ggcctttccg    900
tcctcagccg tcgcttcatg tgactccacg gagtaccggg cgccgtccag gcacctcgat    960
tagttctcga gcttttggag tacgtcgtct ttaggttggg gggaggggtt ttatgcgatg   1020
gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gttttttttct tccatttcag gtgtcgtga                        1179
```

COMBINATORIAL CANCER IMMUNOTHERAPY

RELATED APPLICATIONS

This application is the National Stage of International Application No. PCT/US2018/027492, filed Apr. 13, 2018, which claims the benefit under 35 U.S.C. § 119(e) of U.S. provisional application No. 62/485,295, filed Apr. 13, 2017, and U.S. provisional application No. 62/583,343, filed Nov. 8, 2017, each of which is incorporated by reference herein in its entirety.

SEQUENCE LISTING

The instant application contains a Sequence Listing with 9 sequences which has been submitted via EFS-Web and is hereby incorporated by reference in its entirety. Said ASCII copy, created on Oct. 11, 2019, is named STB004US Sequence Listing.txt, and is 16,295 bytes in size.

BACKGROUND

There are more than 22,000 new cases of ovarian cancer and more than 14,000 deaths each year in the United States (Siegel R L, et al. (2016) CA Cancer J Clin 66(1):7-30), with an estimated annual healthcare burden of greater than $600M (Dizon D M J (2010) Gynecol Oncol 116(3)). Conventional approaches, such as chemotherapy (e.g., carboplatin/cisplatin and/or paclitaxel), are often unable to cure ovarian cancer. Approximately 70% of patients do not achieve remission on first-line chemotherapy, and 40-50% of patients that do have a remission will relapse within three years.

Treatment of other cancers, such as breast cancer and colon cancer, is associated with five-year survival rates of 85% and 65%, respectively. Therapies often include a combination of invasive surgeries and chemotherapies.

SUMMARY

Provided herein, in some embodiments, is a combinatorial cell-based immunotherapy for the targeted treatment of cancer, such as ovarian cancer, breast cancer, colon cancer, lung cancer, and pancreatic cancer. This combinatorial immunotherapy relies on engineered cell circuits that enable multifactorial modulation within and/or near a tumor (a "tumor microenvironment (TME)"). Despite exciting advancements in combinatorial immunotherapy, its efficacy against cancer has been limited due in part to the following challenges. It is difficult to deliver multiple therapies simultaneously to achieve maximal efficacy without triggering significant side effects. It is also difficult in clinical trials to determine the appropriate dosing and timing of multiple systemically-administered and/or locally-injected therapies. The combinatorial immunotherapy provided herein, however, is tumor-specific and effective yet limits systemic toxicity. This combinatorial immunotherapy can be used to deliver to a tumor microenvironment multiple immunomodulatory effector molecules, in some instances, from a single delivery vehicle. Advantageously, cell circuits of the present disclosure are, in some embodiments, engineered in mesenchymal stem cells (MSCs), which are able to selectively home to tumors (including metastases), are able to produce a pro-inflammatory/immunostimulatory secretome and under certain conditions an anti-inflammatory secretome, and are hypoimmunogenic. These characteristics, among others, enable their use for allogenic cell therapies, for example, without significant safety issues, side effects, or rejection.

It has been increasingly recognized that tumors are a complex interplay between the tumor cells and the surrounding stroma, which includes the extracellular matrix, cancer-associated stromal cells (MSCs and fibroblasts), tumor vasculature, and the immune system. The TME suppresses anti-tumor immune responses through multiple mechanisms that target both the innate and adaptive immune system of the patient. For example, tumors can recruit and induce regulatory T cells that suppress the anti-tumor activity of conventional T cells by elaborating specific chemokines such as CCL22. Tumors can also express molecules that inhibit the activity of T cells and NK cells, such as immune checkpoints such as PD-L1. Thus, targeting a single pathway is likely insufficient for achieving robust efficacy against solid tumors.

Thus, the present disclosure, in some aspects, provides mesenchymal stem cells (MSCs) engineered to produce multiple effector molecules, at least two of which modulate different tumor-mediated immunosuppressive mechanisms (e.g., targeting multiple pathways). In some embodiments, an effector molecule (a) stimulates T cell signaling, activity and/or recruitment, (b) stimulates antigen presentation and/or processing, (c) stimulates natural killer cell-mediated cytotoxic signaling, activity and/or recruitment, (d) stimulates dendritic cell differentiation and/or maturation, (e) stimulates immune cell recruitment, (f) stimulates pro-inflammatory macrophage signaling, activity and/or recruitment, or inhibits anti-inflammatory macrophage signaling, activity and/or recruitment, (g) stimulates stroma degradation, (h) stimulates immunostimulatory metabolite production, (i) stimulates Type I interferon signaling, (j) inhibits negative costimulatory signaling, (k) inhibits pro-apoptotic signaling of anti-tumor immune cells (e.g., T cells/NK cells) or induces apoptosis of cancer cells, (l) inhibits T regulatory (Treg) cell signaling, activity and/or recruitment, (m) inhibits tumor checkpoint molecules, (n) stimulates stimulator of interferon genes (STING) signaling, (o) inhibits myeloid-derived suppressor cell signaling, activity and/or recruitment, (p) degrades immunosuppressive factors/metabolites, (q) inhibits vascular endothelial growth factor signaling, and/or (r) directly kills tumor cells. For example, one effector molecule produced by an engineered MSCs may stimulate an anti-tumor immune-mediated mechanism or immunostimulatory mechanism in the TME, while another effector molecule produced by the same MSC (or a different MSC) may inhibit an immunosuppressive mechanism in the TME (e.g., a CD28/B7 family pathway (e.g. PD-1, CTLA-4, CD28) or IL-10). As another example, one effector molecule produced by an engineered MSC may stimulate an inflammatory pathway (e.g., TNF Receptor Superfamily pathway (e.g., OX40, CD137, CD40, GITR), a common gamma-chain family pathway (e.g. IL-2, IL-4, IL-7, IL-9, IL15, IL-21) or Toll-like Receptor pathway (e.g. TLR4, TLR9)) in the tumor microenvironment, while another effector molecule produced by the same MSC (or a different MSC) may inhibit a negative regulator (e.g., Stat3, Bruton's tyrosine kinase, c-kit, and/or SOCS-1) of inflammation in the tumor microenvironment.

Non-limiting examples of effector molecules encompassed by the present disclosure include cytokines, antibodies, chemokines, nucleotides, peptides, enzymes, and oncolytic viruses. For example, MSCs may be engineered to express (and typically secrete) at least one, two, three or more of the following effector molecules: IL-12, IL-16, IFN-β, IFN-γ, IL-2, IL-15, IL-7, IL-36γ, IL-18, IL-10, IL-21, OX40-ligand, CD40L, anti-PD-1 antibodies, anti-PD-L1 antibodies, anti-CTLA-4 antibodies, anti-TGFβ antibodies, anti-TNFR2, MIP1α (CCL3), MIP1β (CCL5), CCL21, CpG oligodeoxynucleotides, and anti-tumor peptides (e.g., anti-microbial peptides having anti-tumor activity, see, e.g., Gaspar, D. et al. *Front Microbiol.* 2013; 4: 294; Chu, H. et al. PLoS One. 2015; 10(5): e0126390, and website:aps.unmc.edu/AP/main.php).

Also provided herein are the methods comprising culturing the mesenchymal stem cells to produce the effector molecules.

Further provided herein are methods comprising delivering to a subject the mesenchymal stem cells to produce in vivo at least one effector molecule produced by the mesenchymal stem cells. In some embodiments, the effector molecules are produced in or delivered to a tumor microenvironment.

Further still, provided herein are methods of treating a cancer, comprising delivering to subject diagnosed with a cancer the mesenchymal stem cells. In some embodiments, the cancer is ovarian cancer, although other cancers/tumors may be treated. For example, the methods provided herein may be used to treat bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and/or uterine tumors.

BRIEF DESCRIPTION OF THE DRAWINGS

FIG. 10A shows that engineered MSCs expressing GFP do not elicit toxicity. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 10A represents an individual mouse. FIG. 10B shows the tumor weight for individual mice in each treatment.

FIG. 17A shows the tumor volume of the individual group. FIG. 17B shows body weight (top), tumor volume (bottom), and survival rate (right).

FIG. 18D shows the percentage of regulatory T cells (Treg) in the total CD3 population. There was a significant decrease in the numbers of Tregs in the tumor microenvironment treated with engineered MSC-IL2 and CCL21a.

FIG. 19 includes data indicating that intraperitoneally injected murine BM-derived MSCs (BM-MSCs) home to the site of CT26 colon cancer tumors in vivo. A brief experimental protocol is provided in the top left corner. The bottom left image (Luciferase Signal (Tumor-Specific)) shows visualization of CT26 tumor cells expressing a luciferase reporter in vivo prior to MSC injection. Fluorescently labeled MSCs were intraperitoneally injected into mice bearing CT26 tumors (Tumor+) and the location of MSCs was visualized with DiR signal analysis. The localization of MSCs in mice bearing CT26 tumors (Tumor+) is shown for one day and three days after MSC injection (DiR signal (MSC-Specific), Tumor+). The results of DiR signal analysis performed on controls (MSC alone, Tumor alone and negative control) are shown as indicated.

FIG. 21B shows the immune profile of three (3) mice in the day 18 group to better characterize the tumor microenvironment.

FIG. 23A shows a significant increase in infiltrating CD3 and CD8 cytotoxic T population in the combo group compared to the group dosed with naïve MSC. FIG. 23B shows a significant reduction in granulocytic myeloid-derived suppressor cells (gMDSCs) and macrophage population in the combo group compared to group treated with Naïve MSC.

FIG. 24A and FIG. 24B show that samples with more CD3+ and CD8+ T cells (top left and center graph) correlate strongly with a decrease in tumor weight. These figures also show that samples with fewer CD11b myeloid cells, including macrophage, dendritic cells, and MDSC, display lower tumor burden (lower center and right graph of FIG. 24A and upper row of FIG. 24B).

FIG. 25A shows that all three lots of MSC-IL12+MSC-CCL21a can reduce tumor burden in both subcutaneous and intraperitoneal model (first 5 graphs are from the SC model and last 3 are from the IP model). Tumors from all mice were collected on day 11. FIG. 25B shows the average tumor weight from each group.

FIG. 26B shows the tumor weight for individual mice in each treatment. MSC-IL12+MSC-CCL21a shows best efficacy compared to mice injected with naïve MSC. Treatment efficacy was also observed in the group treated with MSC-IFNb+MSC-CCL21a.

FIGS. 27A-27B are graphs that show immune profiles of each group treated with indicated engineered MSC. A consistent decrease in macrophage population was observed after treating with MSC-IL12+MSC-CCL21a (FIG. 27A). A general trend of increased infiltration in CD3+population and decreased infiltration in CD11b+population was also observed when compared to group treated with MSC-IL12+MSC-CCL21a against naïve MSC (FIG. 27A and FIG. 27B).

FIG. 28A-28B show the correlation of immune infiltration with tumor weight. Samples with low macrophage and dendritic cells have lower tumor burden (FIG. 28B, top center and top right).

FIG. 29 shows graphs combining the in vivo data from the colorectal cancer models above (FIG. 22A and FIG. 26A). The combined CT26 data from FIG. 22A and FIG. 26A capture three groups: Tumor only (PBS), treated with naïve MSC, and treated with MSC-IL12+MSC-CCL21a.

DETAILED DESCRIPTION

Figure 1:
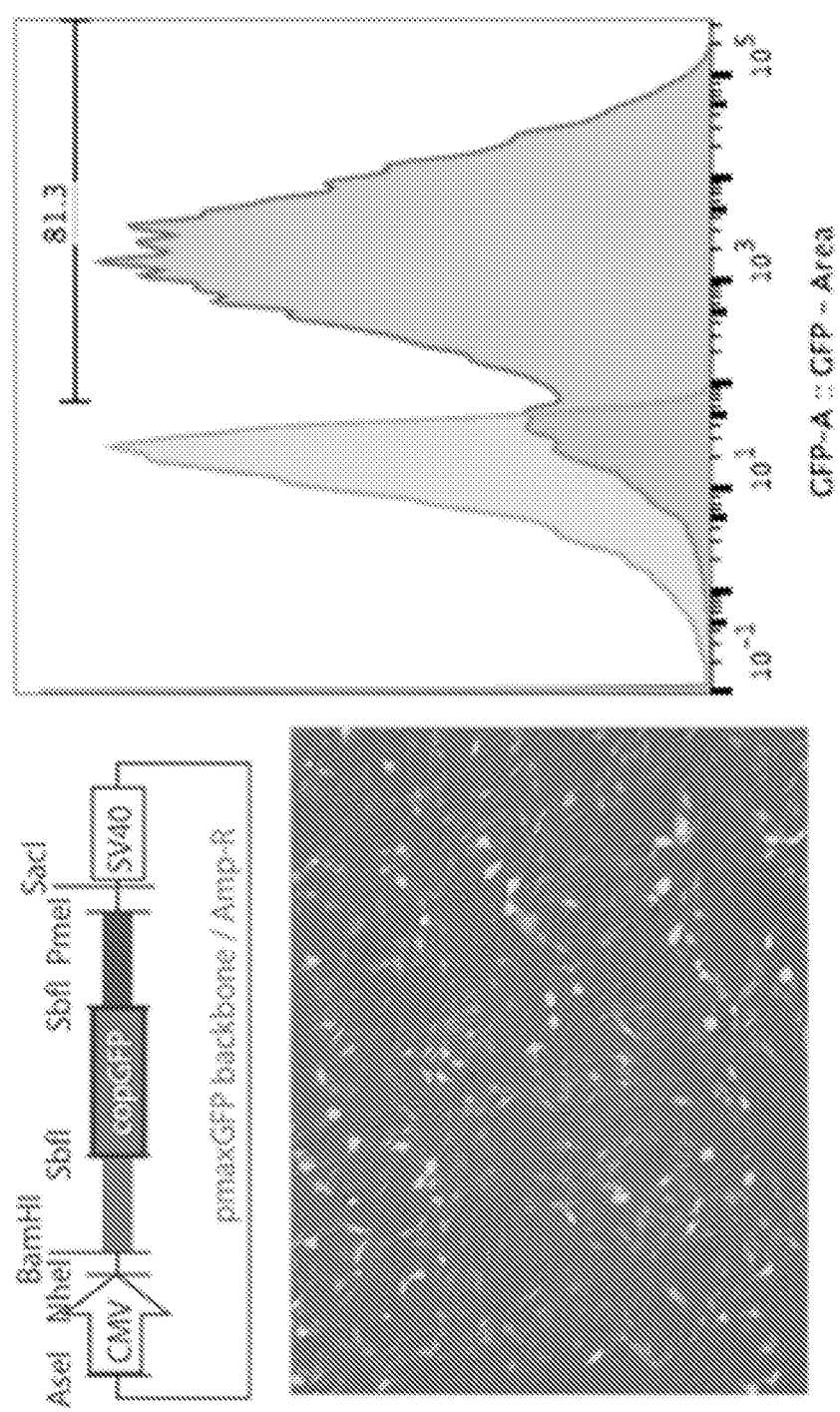
FIG. 1 shows expression of GFP in human MSCs using a nucleofected plasmid with an artificial 5' UTR (bar upstream of copGFP) and 3' UTR (bar downstream of copGFP). >80% of surviving MSCs express high levels of GFP in this protocol (dark gray histogram).

Mesenchymal stem cells (MSCs) (also referred to as mesenchymal stromal cells) are a subset of non-hematopoietic adult stem cells that originate from the mesoderm. They possess self-renewal ability and multilineage differentiation into not only mesoderm lineages, such as chondrocytes, osteocytes and adipocytes, but also ectodermic cells and endodermic cells. MSCs, free of both ethical concerns and teratoma formation, are the major stem cell type used for cell therapy for treatment of both immune diseases and non-immune diseases. They can be easily isolated from the bone marrow, adipose tissue, the umbilical cord, fetal liver, muscle, and lung and can be successfully expanded in vitro. Further, when MSCs are delivered exogenously and systemically to humans and animals, they tend to home to (migrate directly to) damaged tissue sites with inflammation, including tumor microenvironments and metastatic regions. The inflammation-directed MSC homing involves several important cell trafficking-related molecules, including chemokines, adhesion molecules, and matrix metalloproteinases (MMPs).

Provided herein are methods of engineering immune cells, such as MSCs, to produce effector molecules that modulate different tumor-mediated immunosuppressive mechanisms. These MSCs are referred to herein as "engineered MSCs." These MSCs, which typically contain engineered nucleic acid, do not occur in nature. In some embodiments, the MSCs are engineered to include a nucleic acid comprising a promoter operably linked to a nucleotide sequence encoding an effector molecule, for example, one that stimulates an immune response.

An "effector molecule," refers to a molecule (e.g., a nucleic acid such as DNA or RNA, or a protein (polypeptide) or peptide) that binds to another molecule and modulates the biological activity of that molecule to which it binds. For example, an effector molecule may act as a ligand to increase or decrease enzymatic activity, gene expression, or cell signaling. Thus, in some embodiments, an effector molecule modulates (activates or inhibits) different immunomodulatory mechanisms. By directly binding to and modulating a molecule, an effector molecule may also indirectly modulate a second, downstream molecule. In some embodiments, an effector molecule is a secreted molecule, while in other embodiments, an effector molecule is bound to the cell surface or remains intracellular. For example, effector molecules include intracellular transcription factors, microRNA, and shRNAs that modify the internal cell state to, for example, enhance immunomodulatory activity, homing properties, or persistence of the cell. Non-limiting examples of effector molecules include cytokines, chemokines, enzymes that modulate metabolite levels, antibodies or decoy molecules that modulate cytokines, homing molecules, and/or integrins.

The term "modulate" encompasses maintenance of a biological activity, inhibition (partial or complete) of a biological activity, and stimulation/activation (partial or complete) of a biological activity. The term also encompasses decreasing or increasing (e.g., enhancing) a biological activity. Two different effector molecules are considered to "modulate different tumor-mediated immunosuppressive mechanisms" when one effector molecule modulates a tumor-mediated immunosuppressive mechanism (e.g., stimulates T cell signaling) that is different from the tumor-mediated immunosuppressive mechanism modulated by the other effector molecule (e.g., stimulates antigen presentation and/or processing).

Modulation by an effector molecule may be direct or indirect. Direct modulation occurs when an effector molecule binds to another molecule and modulates activity of that molecule. Indirect modulation occurs when an effector molecule binds to another molecule, modulates activity of that molecule, and as a result of that modulation, the activity of yet another molecule (to which the effector molecule is not bound) is modulated.

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in an increase in an immunostimulatory and/or anti-tumor immune response by at least 20%, at least 30%, at least 40%, at least 50%, at least 60%, at least 70%, at least 80%, at least 90%, at least 100%. In some embodiments, modulation of a tumor-mediated immunosuppressive mechanism results in an increase in an immunostimulatory and/or anti-tumor immune response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "an increase" in an immunostimulatory and/or anti-tumor immune response, for example, systemically or in a tumor microenvironment, is relative to the immunostimulatory and/or anti-tumor immune response that would otherwise occur, in the absence of the effector molecule(s).

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in an increase in an immunostimulatory and/or anti-tumor immune response by at least 3 fold, at least 5 fold, at least 10 fold, at least 20 fold, at least 50 fold, or at least 100 fold. In some embodiments, modulation of a tumor-mediated immunosuppressive mechanism results in an increase in an immunostimulatory and/or anti-tumor immune response by 2-10, 2-20, 2-30, 2-40, 2-50, 2-60, 2-70, 2-80, 2-90, or 2-100 fold.

Non-limiting examples of immunostimulatory and/or anti-tumor immune mechanisms include T cell signaling, activity and/or recruitment, antigen presentation and/or processing, natural killer cell-mediated cytotoxic signaling, activity and/or recruitment, dendritic cell differentiation and/or maturation, immune cell recruitment, pro-inflammatory macrophage signaling, activity and/or recruitment, stroma degradation, immunostimulatory metabolite production, stimulator of interferon genes (STING) signaling (which increases the secretion of IFN and Th1 polarization, promoting an anti-tumor immune response), and/or Type I interferon signaling. An effector molecule may stimulate at least one (one or more) of the foregoing immunostimulatory mechanisms, thus resulting in an increase in an immunostimulatory response. Changes in the foregoing immunostimulatory and/or anti-tumor immune mechanisms may be assessed, for example, using in vitro assays for T cell proliferation or cytotoxicity, in vitro antigen presentation assays, expression assays (e.g., of particular markers), and/or cell secretion assays (e.g., of cytokines).

In some embodiments, modulation of a tumor-mediated immunosuppressive mechanism by at least one effector molecule results in a decrease in an immunosuppressive response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in a decrease in an immunosuppressive response by at least 20%, at least 30%, at least 40%, at least 50%, at least 60%, at least 70%, at least 80%, at least 90%, at least 100%. In some embodiments, modulation of a tumor-mediated immunosuppressive mechanism results in a decrease in an immunosuppressive response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "a decrease" in an immunosuppressive response, for example, systemically or in a tumor microenvironment, is relative to the immunosuppressive response that would otherwise occur, in the absence of the effector molecule(s).

In some embodiments, modulation of a tumor-mediated immunosuppressive mechanism by at least one effector molecule results in a decrease in an immunosuppressive response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in a decrease in an immunosuppressive response by at least 3 fold, at least 5 fold, at least 10 fold, at least 20 fold, at least 50 fold, or at least 100 fold. In some embodiments, modulation of a tumor-mediated immunosuppressive mechanism results in a decrease in an immunosuppressive response by 2-10, 2-20, 2-30, 2-40, 2-50, 2-60, 2-70, 2-80, 2-90, or 2-100 fold.

Non-limiting examples of immunosuppressive mechanisms include negative costimulatory signaling, pro-apoptotic signaling of cytotoxic cells (e.g., T cells and/or NK cells), T regulatory (Treg) cell signaling, tumor checkpoint molecule production/maintenance, myeloid-derived suppressor cell signaling, activity and/or recruitment, immunosuppressive factor/metabolite production, and/or vascular endothelial growth factor signaling. An effector molecule may inhibit at least one (one or more) of the foregoing immunosuppressive mechanisms, thus resulting in a decrease in an immunosuppressive response. Changes in the foregoing immunosuppressive mechanisms may be assessed, for example, by assaying for an increase in T cell proliferation and/or an increase in IFNγ production (negative co-stimulatory signaling, $T_{reg}$ cell signaling and/or MDSC); Annexin V/PI flow staining (pro-apoptotic signaling); flow staining for expression, e.g., PDL1 expression (tumor checkpoint molecule production/maintenance); ELISA, LUMINEX®, RNA via qPCR, enzymatic assays, e.g., IDO tryptophan catabolism (immunosuppressive factor/metabolite production); and phosphorylation of PI3K, Akt, p38 (VEGF signaling).

In some embodiments, MSCs are engineered to express membrane-tethered anti-CD3 and/or anti-CD28 agonist extracellular domains.

In some embodiments, MSCs are engineered to produce at least two (e.g., 2, 3, 4, 5, 6, 7, 8, 9, 10 or more) effector molecules, each of which modulates a different tumor-mediated immunosuppressive mechanism. In other embodiments, MSCs are engineered to produce at least one effector molecule that is not natively produced by the MSCs. Such an effector molecule may, for example, complement the function of effector molecules natively produced by the MSCs.

In some embodiments, effector molecules function additively: the effect of two effector molecules, for example, may be equal to the sum of the effect of the two effector molecules functioning separately. In other embodiments, effector molecules function synergistically: the effect of two effector molecules, for example, may be greater than the combined function of the two effector molecules. The present disclosure also encompasses additivity and synergy between an effector molecule(s) and the immune cell (e.g., MSC) from which they are produced.

Effector molecules that modulate tumor-mediated immunosuppressive mechanisms may be, for example, secreted factors (e.g., cytokines, chemokines, antibodies, and/or decoy receptors that modulate extracellular mechanisms involved in the immune system), intracellular factors that control cell state (e.g., microRNAs and/or transcription factors that modulate the state of cells to enhance pro-inflammatory properties), factors packaged into exosomes (e.g., microRNAs, cytosolic factors, and/or extracellular factors), surface displayed factors (e.g., checkpoint inhibitors, TRAIL), and and/or metabolic genes (e.g., enzymes that produce/modulate or degrade metabolites or amino acids).

In some embodiments, effector molecules may be selected from the following non-limiting classes of molecules: cytokines, antibodies, chemokines, nucleotides, peptides, and enzymes. Non-limiting examples of the foregoing classes of effector molecules are listed in

TABLE 1

Exemplary Effector Molecules

| Effector name | Category | Function |
|---|---|---|
| anti-CD40 | Agonist antibody | Stimulates T-cells |
| anti PD-1/PD-L1 | Agonist antibody | Remove checkpoint |
| anti-CTLA-4 | Agonist antibody | Remove checkpoint |
| anti-VEGF | Antagonist antibody | Neutralizes an immunosuppressive/angiogenesis factor |
| anti-TNFa | Antagonist antibody | Neutralizes cytokine/pro-tumor factor |
| anti-IL-10 | Antagonist antibody | Neutralizes immunosuppressive cytokine |
| anti-SDF1/CXCL12 | Antagonist antibody | Neutralizes pro-tumor chemokine |
| (TβRII)2 trap | Capture trap | Neutralizes an immunosuppressive cytokine |
| CCL21 | Chemokine | Attracts leukocytes/NK |
| CCL1 | Chemokine | Attracts leukocytes/NK |
| CCL17 | Chemokine | Attracts leukocytes/NK |
| CCL19 | Chemokine | Attracts leukocytes/NK |
| CCL21 | Chemokine | Attracts leukocytes/NK |
| CCL20 | Chemokine | Attracts leukocytes/NK |
| CCL21a | Chemokine | Attracts leukocytes/NK |
| MIP1b (CCL5) | Chemokine | Attracts leukocytes/NK |
| CXCL10 | Chemokine | Attracts leukocytes/NK |
| CXCL11 | Chemokine | Attracts leukocytes/NK |
| CCL2 | Chemokine | Attracts monocytes |
| MIP-1alpha (CCL3) | Chemokine | Attracts leukocytes/NK |
| XCL1 | Chemokine | Attracts leukocytes/NK |
| IFNbeta | Cytokine | T cell response, tumor cell killing |
| IFNgamma | Cytokine | T cell response, tumor cell killing |
| IL-12 | Cytokine | T cells, NK cells |
| IL-1beta | Cytokine | T cells, NK cells |
| IL-15 | Cytokine | Stimulates T-cells and NK |
| IL-2 | Cytokine | Stimulates T-cells and NK |
| IL-21 | Cytokine | Stimulates T-cells |
| IL-24 | Cytokine | Stimulates T-cells |
| IL36-gamma | Cytokine | Stimulates T-cells |
| IL-7 | Cytokine | Stimulates T-cells |
| IL-22 | Cytokine | Stimulates T-cells |
| IL-18 | Cytokine | Stimulates T-cells |
| Granzymes/Perforin | Enzyme | Direct tumor cell killing |
| OX86 (anti-OX40) | ligand | Stimulates T-cells |
| anti-TGFbeta | Neutralizing antibody | Neutralizes an Immunosuppressive cytokine |
| TRAIL | Receptor/ligand | Direct tumor cell killing |
| FASL (CD49L) | Receptor/ligand | Direct tumor cell killing |
| OX40-L | Receptor/Ligand | Stimulates T-cells |
| cGAS | secreted molecule | Stimulates antigen-presenting cells |
| 41BBL | secreted molecule | Co-activation of T-cells |
| CD40L | secreted molecule | Stimulates T-cells |
| GM-CSF | secreted molecule | Growth factor for monocytes |
| STING | secreted molecule | Stimulates antigen-presenting cells |
| HAC-V 'microbody'_PD1 | Antagonist antibody | inhibits checkpoint |
| yCD | Pro-drug | Converts to cytotoxic molecule upon activation |
| CpG/Nucleotides | Nucleotides | STING agonist |

In some embodiments, MSCs comprise an engineered nucleic acid that comprises a promoter operably linked to a nucleotide sequence encoding an effector molecule. In some embodiments, an engineered nucleic acid comprises a promoter operably linked to a nucleotide sequence encoding at least 2 effector molecules. For example, the engineered nucleic acid may comprise a promoter operably linked to a nucleotide sequence encoding at least 3, at least 4, at least 5, at least 6, at least 7, at least 8, at least 8, at least 9, or at least 10 effector molecules. In some embodiments, an engineered nucleic acid comprises a promoter operably linked to a nucleotide sequence encoding 1, 2, 3, 4, 5, 6, 7, 8, 9, 10, or more effector molecules.

MSCs, in some embodiments, are engineered to include at least two engineered nucleic acids, each comprising a promoter operably linked to a nucleotide sequence encoding at least one (e.g., 1, 2 or 3) effector molecule. For example, the MSCs may be engineered to comprise at least 2, at least 3, at least 4, at least 5, at least 6, at least 7, at least 8, at least 8, at least 9, or at least 10, engineered nucleic acids, each comprising a promoter operably linked to a nucleotide sequence encoding at least one (e.g., 1, 2 or 3) effector molecule. In some embodiments, the MSCs are engineered to comprise 2, 3, 4, 5, 6, 7, 8, 9, 10, or more engineered nucleic acids, each comprising a promoter operably linked to a nucleotide sequence encoding at least one (e.g., 1, 2 or 3) effector molecule.

An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. The term "engineered nucleic acids" includes recombinant nucleic acids and synthetic nucleic acids. A "recombinant nucleic acid" refers to a molecule that is constructed by joining nucleic acid molecules and, in some embodiments, can replicate in a live cell. A "synthetic nucleic acid" refers to a molecule that is amplified or chemically, or by other means, synthesized. Synthetic nucleic acids include those that are chemically modified, or otherwise modified, but can base pair with naturally-occurring nucleic acid molecules. Recombinant nucleic acids and synthetic nucleic acids also include those molecules that result from the replication of either of the foregoing. Engineered nucleic acid of the present disclosure may be encoded by a single molecule (e.g., included in the same plasmid or other vector) or by multiple different molecules (e.g., multiple different independently-replicating molecules).

Engineered nucleic acid of the present disclosure may be produced using standard molecular biology methods (see, e.g., Green and Sambrook, Molecular Cloning, A Laboratory Manual, 2012, Cold Spring Harbor Press). In some embodiments, engineered nucleic acid constructs are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease, the 'Y extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. In some embodiments, engineered nucleic acid constructs are produced using IN-FUSION® cloning (Clontech).

A "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous." In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see, e.g., U.S. Pat. Nos. 4,683,202 and 5,928,906).

Promoters of an engineered nucleic acid may be "inducible promoters," which refer to promoters that are characterized by regulating (e.g., initiating or activating) transcriptional activity when in the presence of, influenced by or contacted by a signal. The signal may be endogenous or a normally exogenous condition (e.g., light), compound (e.g., chemical or non-chemical compound) or protein (e.g., cytokine) that contacts an inducible promoter in such a way as to be active in regulating transcriptional activity from the inducible promoter. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

A promoter is "responsive to" or "modulated by" a local tumor state (e.g., inflammation or hypoxia) or signal if in the presence of that state or signal, transcription from the promoter is activated, deactivated, increased, or decreased. In some embodiments, the promoter comprises a response element. A "response element" is a short sequence of DNA within a promoter region that binds specific molecules (e.g., transcription factors) that modulate (regulate) gene expression from the promoter. Response elements that may be used in accordance with the present disclosure include, without limitation, a phloretin-adjustable control element (PEACE), a zinc-finger DNA-binding domain (DBD), an interferon-gamma-activated sequence (GAS) (Decker, T. et al. *J Interferon Cytokine Res.* 1997 March; 17(3):121-34, incorporated herein by reference), an interferon-stimulated response element (ISRE) (Han, K. J. et al. *J Biol Chem.* 2004 Apr. 9; 279(15):15652-61, incorporated herein by reference), a NF-kappaB response element (Wang, V. et al. Cell Reports.

2012; 2(4): 824-839, incorporated herein by reference), and a STAT5 response element (Zhang, D. et al. *J of Biol Chem.* 1996; 271: 9503-9509, incorporated herein by reference). Other response elements are encompassed herein.

Non-limiting examples of responsive promoters (e.g., TGF-beta responsive promoters) are listed in Table 2, which shows the design of the promoter and transcription factor, as well as the effect of the inducer molecule towards the transcription factor (TF) and transgene transcription (T) is shown (B, binding; D, dissociation; n.d., not determined) (A, activation; DA, deactivation; DR, derepression) (see Horner, M. & Weber, W. *FEBS Letters* 586 (2012) 20784-2096m, and references cited therein).

TABLE 2

Examples of Responsive Promoters.

| System | Promoter and operator | Transcription factor (TF) | Inducer molecule | Response to inducer TF | T |
|---|---|---|---|---|---|
| *Transcriptional activator-responsive promoters* | | | | | |
| AIR | PAIR (OalcA-PhCMVmin) | AlcR | Acetaldehyde | n.d. | A |
| ART | PART (OARG-PhCMVmin) | ArgR-VP16 | 1-Arginine | B | A |
| BIT | PBIT3 (OBirA3-PhCMVmin) | BIT (BirA-VP16) | Biotin | B | A |
| Cumate - activator | PCR5 (OCuO6-PhCMVmin) | cTA (CymR-VP16) | Cumate | D | DA |
| Cumate - reverse activator | PCR5 (OCuO6-PhCMVmin) | rcTA (rCymR-VP16) | Cumate | B | A |
| E-OFF | PETR (OETR-PhCMVmin) | ET (E-VP16) | Erythromycin | D | DA |
| NICE-OFF | PNIC (ONIC-PhCMVmin) | NT (HdnoR-VP16) | 6-Hydroxy-nicotine | D | DA |
| PEACE | PTtgR1 (OTtgR-PhCMVmin) | TtgA1 (TtgR-VP16) | Phloretin | D | DA |
| PIP-OFF | PPIR (OPIR-Phsp70min) | PIT (PIP-VP16) | Pristinamycin I | D | DA |
| QuoRex | PSCA (OscbR-PhCMVmin)PSPA (OpapRI-PhCMVmin) | SCA (ScbR-VP16) | SCB1 | D | DA |
| Redox | PROP (OROP-PhCMVmin) | REDOX (REX-VP16) | NADH | D | DA |
| TET-OFF | PhCMV*-1 (OtetO7-PhCMVmin) | tTA (TetR-VP16) | Tetracycline | D | DA |
| TET-ON | PhCMV*-1 (OtetO7-PhCMVmin) | rtTA (rTetR-VP16) | Doxycycline | B | A |
| TIGR | PCTA (OrheO-PhCMVmin) | CTA (RheA-VP16) | Heat | D | DA |
| TraR | O7x(tra box)-PhCMVmin | p65-TraR | 3-Oxo-C8-HSL | B | A |
| VAC-OFF | P1V anO2 (OVanO2-PhCMVmin) | VanA1 (VanR-VP16) | Vanillic acid | D | DA |
| *Transcriptional repressor-responsive promoters* | | | | | |
| Cumate - repressor | PCuO (PCMV5-OCuO) | CymR | Cumate | D | DR |
| E-ON | PETRON8 (PSV40-OETR8) | E-KRAB | Erythromycin | D | DR |
| NICE-ON | PNIC (PSV40-ONIC8) | NS (HdnoR-KRAB) | 6-Hydroxy-nicotine | D | DR |
| PIP-ON | PPIRON (PSV40-0PIR3) | PIT3 (PIP-KRAB) | Pristinamycin I | D | DR |
| Q-ON | PSCAON8 (PSV40-OscbR8) | SCS (ScbR-KRAB) | SCB1 | D | DR |
| TET-ON<comma> repressor-based | OtetO-PHPRT | tTS-H4 (TetR-HDAC4) | Doxycycline | D | DR |
| T-REX | PTetO (PhCMV-OtetO2) | TetR | Tetracycline | D | DR |
| UREX | PUREX8 (PSV40-OhucO8) | mUTS (KRAB-HucR) | Uric acid | D | DR |
| VAC-ON | PVanON8 (PhCMV-OVanO8) | VanA4 (VanR-KRAB) | Vanillic acid | D | DR |
| *Hybrid promoters* | | | | | |
| QuoRexPIP-ON(NOT IF gate) | OscbR8-OPIR3-PhCMVmin | SCAPIT3 | SCB1Pristinamycin I | DD | DADR |
| QuoRexE-ON(NOT IF gate) | OscbR-OETR8-PhCMVmin | SCAE-KRAB | SCB1Erythromycin | DD | DADR |
| TET-OFFE-ON(NOT IF gate) | OtetO7-OETR8-PhCMVmin | tTAE-KRAB | TetracyclineErythromycin | DD | DADR |
| TET-OFFPIP-ONE-ON | OtetO7-OPIR3-OETR8-PhCMVmin | tTAPIT3E-KRAB | TetracyclinePristinamycin IErythromycin | DDD | DADRDR |

Other non-limiting examples of promoters include the cytomegalovirus (CMV) promoter, the elongation factor 1-alpha (EF1a) promoter, the elongation factor (EFS) promoter, the MND promoter (a synthetic promoter that contains the U3 region of a modified MoMuLV LTR with myeloproliferative sarcoma virus enhancer), the phosphoglycerate kinase (PGK) promoter, the spleen focus-forming virus (SFFV) promoter, the simian virus 40 (SV40) promoter, and the ubiquitin C (UbC) promoter (see Table 3).

TABLE 3

Exemplary Promoters

| Name | DNA SEQUENCE |
| --- | --- |
| CMV | GTTGACATTGATTATTGACTAGTTATTAATAGTAATCAATTACGGGGTCATTA<br>GTTCATAGCCCATATATGGAGTTCCGCGTTACATAACTTACGGTAAATGGCCC<br>GCCTGGCTGACCGCCCAACGACCCCCGCCCATTGACGTCAATAATGACGTAT<br>GTTCCCATAGTAACGCCAATAGGGACTTTCCATTGACGTCAATGGGTGGAGT<br>ATTTACGGTAAACTGCCCACTTGGCAGTACATCAAGTGTATCATATGCCAAGT<br>ACGCCCCCTATTGACGTCAATGACGGTAAATGGCCCGCCTGGCATTATGCCC<br>AGTACATGACCTTATGGGACTTTCCTACTTGGCAGTACATCTACGTATTAGTC<br>ATCGCTATTACCATGGTGATGCGGTTTTGGCAGTACATCAATGGGCGTGGAT<br>AGCGGTTTGACTCACGGGGATTTCCAAGTCTCCACCCCATTGACGTCAATGG<br>GAGTTTGTTTTGGCACCAAAATCAACGGGACTTTCCAAAATGTCGTAACAAC<br>TCCGCCCCATTGACGCAAATGGGCGGTAGGCGTGTACGGTGGGAGGTCTATA<br>TAAGCAGAGCTC (SEQ ID NO: 1) |
| EF1a | GGCTCCGGTGCCCGTCAGTGGGCAGAGCGCACATCGCCCACAGTCCCCGAGA<br>AGTTGGGGGGAGGGGTCGGCAATTGAACCGGTGCCTAGAGAAGGTGGCGCG<br>GGGTAAACTGGGAAAGTGATGCCGTGTACTGGCTCCGCCTTTTTCCCGAGGG<br>TGGGGGAGAACCGTATATAAGTGCAGTAGTCGCCGTGAACGTTCTTTTTCGC<br>AACGGGTTTGCCGCCAGAACACAGGTAAGTGCCGTGTGTGGTTCCCGCGGGC<br>CTGGCCTCTTTACGGGTTATGGCCCTTGCGTGCCTTGAATTACTTCCACCTGG<br>CTGCAGTACGTGATTCTTGATCCCGAGCTTCGGGTTGGAAGTGGGTGGGAGA<br>GTTCGAGGCCTTGCGCTTAAGGAGCCCCTTCGCCTCGTGCTTGAGTTGAGGCC<br>TGGCCTGGGCGCTGGGGCCGCCGCGTGCGAATCTGGTGGCACCTTCGCGCT<br>GTCTCGCTGCTTTCGATAAGTCTCTAGCCATTTAAAATTTTTGATGACCTGCT<br>GCGACGCTTTTTTTCTGGCAAGATAGTCTTGTAAATGCGGGCCAAGATCTGCA<br>CACTGGTATTTCGGTTTTTGGGGCCGCGGGCGGCGACGGGGCCCGTGCGTCC<br>CAGCGCACATGTTCGGCGAGGCGGGGCCTGCGAGCGCGACCACCGAGAATC<br>GGACGGGGGTAGTCTCAAGCTGGCCGGCCTGCTCTGGTGCCTGTCCTCGCGC<br>CGCCGTGTATCGCCCCGCCCGGGCGGCAAGGCTGGCCCGGTCGGCACCAGT<br>TGCCGTGAGCGGAAAGATGGCCGCTTCCCGGTCCTGCTGCAGGGAGCTCAAAA<br>TGGAGGACGCGGCGCTCGGGAGAGCGGGCGGGTGAGTCACCCACACAAAGG<br>AAAAGGGCCTTTCCGTCCTCAGCCGTCGCTTCATGTGACTCCACGGAGTACC<br>GGGCGCCGTCCAGGCACCTCGATTAGTTCTCGAGCTTTTGGAGTACGTCGTCT<br>TTAGGTTGGGGGGAGGGGTTTTATGCGATGGAGTTTCCCCACACTGAGTGGG<br>TGGAGACTGAAGTTAGGCCAGCTTGGCACTTGATGTAATTCTCCTTGGAATTT<br>GCCCTTTTTGAGTTTGGATCTTGGTTCATTCTCAAGCCTCAGACAGTGGTTCA<br>AAGTTTTTTTCTTCCATTTCAGGTGTCGTGA |
| EFS | GGATCTGCGATCGCTCCGGTGCCCGTCAGTGGGCAGAGCGCACATCGCCCAC<br>AGTCCCCGAGAAGTTGGGGGGAGGGGTCGGCAATTGAACCGGTGCCTAGAG<br>AAGGTGGCGCGGGGTAAACTGGGAAAGTGATGTCGTGTACTGGCTCCGCCTT<br>TTTCCCGAGGGTGGGGGAGAACCGTATATAAGTGCAGTAGTCGCCGTGAACG<br>TTCTTTTTCGCAACGGGTTTGCCGCCAGAACACAGCTGAAGCTTCGAGGGGC<br>TCGCATCTCTCCTTCACGCGCCCGCCGCCCTACCTGAGGCCGCCATCCACGCC<br>GGTTGAGTCGCGTTCTGCCGCCTCCCGCCTGTGGTGCCTCCTGAACTGCGTCC<br>GCCGTCTAGGTAAGTTTAAAGCTCAGGTCGAGACCGGGCCTTTGTCCGGCGC<br>TCCCTTGGAGCCTACCTAGACTCAGCCGGCTCTCCACGCTTTGCCTGACCCTG<br>CTTGCTCAACTCTACGTCTTTGTTTCGTTTTCTGTTCTGCGCCGTTACAGATCC<br>AAGCTGTGACCGGCGCCTAC (SEQ ID NO: 2) |
| MND | TTTATTTAGTCTCCAGAAAAAGGGGGGAATGAAAGACCCCACCTGTAGGTTT<br>GGCAAGCTAGGATCAAGGTTAGGAACAGAGAGACAGCAGAATATGGGCCAA<br>ACAGGATATCTGTGGTAAGCAGTTCCTGCCCCGGCTCAGGGCCAAGAACAGT<br>TGGAACAGCAGAATATGGGCCAAACAGGATATCTGTGGTAAGCAGTTCCTGC<br>CCCGGCTCAGGGCCAAGAACAGATGGTCCCCAGATGCGGTCCCGCCCTCAGC<br>AGTTTCTAGAGAACCATCAGATGTTTCCAGGGTGCCCCAAGGACCTGAAATG<br>ACCCTGTGCCTTATTTGAACTAACCAATCAGTTCGCTTCTCGCTTCTGTTCGC<br>GCGCTTCTGCTCCCCGAGCTCAATAAAAGAGCCCA (SEQ ID NO: 3) |
| PGK | GGGGTTGGGGTTGCGCCTTTTCCAAGGCAGCCCTGGGTTTGCGCAGGGACGC<br>GGCTGCTCTGGGCGTGGTTCCGGGAAACGCAGCGGCGCCGACCCTGGGTCTC<br>GCACATTCTTCACGTCCGTTCGCAGCGTCACCCGGATCTTCGCCGCTACCCTT<br>GTGGGCCCCCCGGCGACGCTTCCTGCTCCGCCCCTAAGTCGGGAAGGTTCCT<br>TGCCGGTTCGCGGCGTGCCGGACGTGACAAACGGAAGCCGCACGTCTCACTAG<br>TACCCTCGCAGACGGACAGCGCCAGGGAGCAATGGCAGCGCGCGACCGCG<br>ATGGGCTGTGGCCAATAGCGGCTGCTCAGCGGGGCGCGCCGAGAGCAGCGG<br>CCGGGAAGGGGCGGTGCGGGAGGCGGGGTGTGGGCGGTAGTGTGGGCCCT<br>GTTCCTGCCCGCGCGGTGTTCCGCATTCTGCAAGCCTCCGGAGCGCACGTCG<br>GCAGTCGGCTCCCTCGTTGACCGAATCACCGACCTCTCTCCCCAG (SEQ ID NO: 4) |

TABLE 3-continued

Exemplary Promoters

Name DNA SEQUENCE

SFFV GTAACGCCATTTTGCAAGGCATGGAAAAATACCAAACCAAGAATAGAGAAG
TTCAGATCAAGGGCGGGTACATGAAAATAGCTAACGTTGGGCCAAACAGGA
TATCTGCGGTGAGCAGTTTCGGCCCCGGCCCGGGGCCAAGAACAGATGGTCA
CCGCAGTTTCGGCCCCGGCCCGAGGCCAAGAACAGATGGTCCCCAGATATGG
CCCAACCCTCAGCAGTTTCTTAAGACCCATCAGATGTTTCCAGGCTCCCCCAA
GGACCTGAAATGACCCTGCGCCTTATTTGAATTAACCAATCAGCCTGCTTCTC
GCTTCTGTTCGCGCGCTTCTGCTTCCCGAGCTCTATAAAAGAGCTCACAACCC
CTCACTCGGCGCGCCAGTCCTCCGACAGACTGAGTCGCCCGGG (SEQ ID NO:
5)

SV40 CTGTGGAATGTGTGTCAGTTAGGGTGTGGAAAGTCCCCAGGCTCCCCAGCAG
GCAGAAGTATGCAAAGCATGCATCTCAATTAGTCAGCAACCAGGTGTGGAAA
GTCCCCAGGCTCCCCAGCAGGCAGAAGTATGCAAAGCATGCATCTCAATTAG
TCAGCAACCATAGTCCCGCCCCTAACTCCGCCCATCCCGCCCCTAACTCCGCC
CAGTTCCGCCCATTCTCCGCCCCATGGCTGACTAATTTTTTTATTTATGCAGA
GGCCGAGGCCGCCTCTGCCTCTGAGCTATTCCAGAAGTAGTGAGGAGGCTTT
TTTGGAGGCCTAGGCTTTTGCAAAAAGCT (SEQ ID NO: 6)

UbC GCGCCGGGTTTTGGCGCCTCCCGCGGGCGCCCCCCTCCTCACGGCGAGCGCT
GCCACGTCAGACGAAGGGCGCAGGAGCGTTCCTGATCCTTCCGCCCGGACGC
TCAGGACAGCGGCCCGCTGCTCATAAGACTCGGCCTTAGAACCCCAGTATCA
GCAGAAGGACATTTTAGGACGGGACTTGGGTGACTCTAGGGCACTGGTTTTC
TTTCCAGAGAGCGGAACAGGCGAGGAAAAGTAGTCCCTTCTCGGCGATTCTG
CGGAGGGATCTCCGTGGGGCGGTGAACGCCGATGATTATATAAGGACGCGCC
GGGTGTGGCACAGCTAGTTCCGTCGCAGCCGGGATTTGGGTCGCGGTTCTTG
TTTGTGGATCGCTGTGATCGTCACTTGGTGAGTTGCGGGCTGCTGGGCTGGCC
GGGGCTTTCGTGGCCGCCGGGCCGCTCGGTGGGACGGAAGCGTGTGGAGAG
ACCGCCAAGGGCTGTAGTCTGGGTCCGCGAGCAAGGTTGCCCTGAACTGGGG
GTTGGGGGGAGCGCACAAAATGGCGGCTGTTCCCGAGTCTTGAATGGAAGAC
GCTTGTAAGGCGGGCTGTGAGGTCGTTGAAACAAGGTGGGGGGCATGGTGG
GCGGCAAGAACCCAAGGTCTTGAGGCCTTCGCTAATGCGGGAAAGCTCTTAT
TCGGGTGAGATGGGCTGGGGCACCATCTGGGGACCCTGACGTGAAGTTTGTC
ACTGACTGGAGAACTCGGGTTTGTCGTCTGGTTGCGGGGGCGGCAGTTATGC
GGTGCCGTTGGGCAGTGCACCCGTACCTTTGGGAGCGCGCGCCTCGTCGTGT
CGTGACGTCACCCGTTCTGTTGGCTTATAATGCAGGGTGGGGCCACCTGCCG
GTAGGTGTGCGGTAGGCTTTTCTCCGTCGCAGGACGCAGGGTTCGGGCCTAG
GGTAGGCTCTCCTGAATCGACAGGCGCCGGACCTCTGGTGAGGGGAGGGATA
AGTGAGGCGTCAGTTTCTTTGGTCGGTTTTATGTACCTATCTTCTTAAGTAGC
TGAAGCTCCGGTTTTGAACTATGCGCTCGGGGTTGGCGAGTGTGTTTTGTGAA
GTTTTTTAGGCACCTTTTGAAATGTAATCATTTGGGTCAATATGTAATTTTCA
GTGTTAGACTAGTAAAGCTTCTGCAGGTCGACTCTAGAAAATTGTCCGCTAA
ATTCTGGCCGTTTTTGGCTTTTTTGTTAGAC (SEQ ID NO: 7)

In some embodiments, a promoter of the present disclosure is modulated by signals within a tumor microenvironment. A tumor microenvironment is considered to modulate a promoter if, in the presence of the tumor microenvironment, the activity of the promoter is increased or decreased by at least 10%, relative to activity of the promoter in the absence of the tumor microenvironment. In some embodiments, the activity of the promoter is increased or decreased by at least 20%, at least 30%, at least 40%, at least 50%, at least 60%, at least 70%, at least 80%, at least 90%, at least 100%, relative to activity of the promoter in the absence of the tumor microenvironment. For example, the activity of the promoter is increased or decreased by 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%, relative to activity of the promoter in the absence of the tumor microenvironment.

In some embodiments, the activity of the promoter is increased or decreased by at least 2 fold (e.g., 2, 3, 4, 5, 10, 25, 20, 25, 50, or 100 fold), relative to activity of the promoter in the absence of the tumor microenvironment. For example, the activity of the promoter is increased or decreased by at least 3 fold, at least 5 fold, at least 10 fold, at least 20 fold, at least 50 fold, or at least 100 fold, relative to activity of the promoter in the absence of the tumor microenvironment. In some embodiments, the activity of the promoter is increased or decreased by 2-10, 2-20, 2-30, 2-40, 2-50, 2-60, 2-70, 2-80, 2-90, or 2-100 fold, relative to activity of the promoter in the absence of the tumor microenvironment.

In some embodiments, a promoter of the present disclosure is activated under a hypoxic condition. A "hypoxic condition" is a condition where the body or a region of the body is deprived of adequate oxygen supply at the tissue level. Hypoxic conditions can cause inflammation (e.g., the level of inflammatory cytokines increase under hypoxic conditions). In some embodiments, the promoter that is activated under hypoxic condition is operably linked to a nucleotide encoding an effector molecule that decreases the expression of activity of inflammatory cytokines, thus reducing the inflammation caused by the hypoxic condition. In some embodiments, the promoter that is activated under hypoxic conditions comprises a hypoxia responsive element (HRE). A "hypoxia responsive element (HRE)" is a response element that responds to hypoxia-inducible factor (HIF). The HRE, in some embodiments, comprises a consensus motif NCGTG (where N is either A or G).

In some embodiments, engineered MSCs produce multiple effector molecules. For example, MSCs may be engineered to produce 2-20 different effector molecules. In some embodiments, MSCs engineered to produce 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, or 19-20 effector molecules. In some embodiments, MSCs are engineered to produce 1, 2, 3, 4, 5, 6, 7, 8, 9, 10, 11, 12, 13, 14, 15, 16, 17, 18, 19, or 20 effector molecules.

Engineered MSCs of the present disclosure typically produce multiple effector molecules, at least two of which modulate different tumor-mediated immunosuppressive mechanisms. In some embodiments, at least one of the effector molecules stimulates an inflammatory pathway in the tumor microenvironment, and at least one of the effector molecules inhibits a negative regulator of inflammation in the tumor microenvironment.

A "tumor microenvironment" is the cellular environment in which a tumor exists, including surrounding blood vessels, immune cells, fibroblasts, bone marrow-derived inflammatory cells, lymphocytes, signaling molecules and the extracellular matrix (ECM) (see, e.g., Pattabiraman, D. R. & Weinberg, R. A. *Nature Reviews Drug Discovery* 13, 497-512 (2014); Balkwill, F. R. et al. *J Cell Sci* 125, 5591-5596, 2012; and Li, H. et al. *J Cell Biochem* 101(4), 805-15, 2007).

In some embodiments, MSCs are engineered to produce at least one homing molecule. "Homing," refers to active navigation (migration) of a cell to a target site (e.g., a cell, tissue (e.g., tumor), or organ). A "homing molecule" refers to a molecule that directs MSCs to a target site. In some embodiments, a homing molecule functions to recognize and/or initiate interaction of a MSC to a target site. Non-limiting examples of homing molecules include CXCR1 CCR9, CXCR2, CXCR3, CXCR4, CCR2, CCR4, FPR2, VEGFR, IL6R, CXCR1, CSCR7, and PDGFR.

In some embodiments, a homing molecule is a chemokine receptor (cell surface molecule that binds to a chemokine). Chemokines are small cytokines or signaling proteins secreted by cells that can induce directed chemotaxis in cells. Chemokines can be classified into four main subfamilies: CXC, CC, CX3C and XC, all of which exert biological effects by binding selectively to chemokine receptors located on the surface of target cells. In some embodiments, MSCs are engineered to produce CXCR4, a chemokine receptor which allows MSCs to home along a chemokine gradient towards a stromal cell-derived factor 1 (also known as SDF1, C—X—C motif chemokine 12, and CXCL12)-expressing cell, tissue, or tumor. Non-limiting examples of chemokine receptors that may be produced by the engineered MSCs of the present disclosure include: CXC chemokine receptors (e.g., CXCR1, CXCR2, CXCR3, CXCR4, CXCR5, CXCR6, and CXCR7), CC chemokine receptors (CCR1, CCR2, CCR3, CCR4, CCR5, CCR6, CCR7, CCR8, CCR9, CCR10, and CCR11), CX3C chemokine receptors (e.g., CX3CR1, which binds to CX3CL1), and XC chemokine receptors (e.g., XCR1). In some embodiments, a chemokine receptor is a G protein-linked transmembrane receptor, or a member of the tumor necrosis factor (TNF) receptor superfamily (including but not limited to TNFRSF1A, TNFRSF1B). In some embodiments, MSCs are engineered to produce CXCL8, CXCL9, and/or CXCL10 (promote T-cell recruitment), CCL3 and/or CXCL5, CCL21 (Th1 recruitment and polarization).

In some embodiments, MSCs are engineered to produce G-protein coupled receptors (GPCRs) that detect N-formylated-containing oligopeptides (including but not limited to FPR2 and FPRL1).

In some embodiments, MSCs are engineered to produce receptors that detect interleukins (including but not limited to IL6R).

In some embodiments, MSCs are engineered to produce receptors that detect growth factors secreted from other cells, tissues, or tumors (including but not limited to FGFR, PDGFR, EGFR, and receptors of the VEGF family, including but not limited to VEGF-C and VEGF-D).

In some embodiments, a homing molecule is an integrin. Integrins are transmembrane receptors that facilitate cell-extracellular matrix (ECM) adhesion. Integrins are obligate heterodimers having two subunits: α (alpha) and β (beta). The α subunit of an integrin may be, without limitation: ITGA1, ITGA2, ITGA3, ITGA4, ITGA5, ITGA6, IGTA7, ITGA8, ITGA9, IGTA10, IGTA11, ITGAD, ITGAE, ITGAL, ITGAM, ITGAV, ITGA2B, ITGAX. The β subunit of an integrin may be, without limitation: ITGB1, ITGB2, ITGB3, ITGB4, ITGB5, ITGB6, ITGB7, and ITGB8. MSCs of the present disclosure may be engineered to produce any combination of the integrin α and β subunits.

In some embodiments, a homing molecule is a matrix metalloproteinase (MMP). MMPs are enzymes that cleave components of the basement membrane underlying the endothelial cell wall. Non-limiting examples of MMPs include MMP-2, MMP-9, and MMP. In some embodiments, MSCs are engineered to produce an inhibitor of a molecule (e.g., protein) that inhibits MMPs. For example, MSCs may be engineered to express an inhibitor (e.g., an RNAi molecule) of membrane type 1 MMP (MT1-MMP) or TIMP metallopeptidase inhibitor 1 (TIMP-1).

In some embodiments, a homing molecule is a ligand that binds to selectin (e.g., hematopoietic cell E-/L-selectin ligand (HCELL), Dykstra et al., Stem Cells. 2016 October; 34(10):2501-2511) on the endothelium of a target tissue, for example.

The term "homing molecule" also encompasses transcription factors that regulate the production of molecules that improve/enhance homing of MSCs.

In some embodiments, MSC homing is increased by locally irradiating a tumor/cancer cells in a subject. Radiological tissue damage aids in MSC homing, as well as endogenous T cell homing to that damaged tissue.

Examples of Engineered Cells

Cells (e.g., MSCs) as provided herein are engineered to produce multiple effector molecules, at least two of which modulate different tumor-mediated immunosuppressive mechanisms. In some embodiments, at least one (e.g., 1, 2, 3, 4, 5, or more) effector molecule stimulates at least one immunostimulatory mechanism in the tumor microenvironment, or inhibits at least one immunosuppressive mechanism in the tumor microenvironment. In some embodiments, at least one (e.g., 1, 2, 3, 4, 5, or more) effector molecule inhibits at least one immunosuppressive mechanism in the tumor microenvironment, and at least one effector molecule (e.g., 1, 2, 3, 4, 5, or more) inhibits at least one immunosuppressive mechanism in the tumor microenvironment. In yet other embodiments, at least two (e.g., 2, 3, 4, 5, or more) effector molecules stimulate at least one immunostimulatory mechanism in the tumor microenvironment. In still other embodiments, at least two (e.g., 1, 2, 3, 4, 5, or more) effector molecules inhibit at least one immunosuppressive mechanism in the tumor microenvironment.

In some embodiments, a cell (e.g., MSC) is engineered to produce at least one effector molecule that stimulates T cell signaling, activity and/or recruitment. In some embodiments, a cell (e.g., MSC) is engineered to produce at least one effector molecule that stimulates antigen presentation and/or processing. In some embodiments, a cell (e.g., MSC) is engineered to produce at least one effector molecule that stimulates natural killer cell-mediated cytotoxic signaling, activity and/or recruitment. In some embodiments, a cell (e.g., MSC) is engineered to produce at least one effector molecule that stimulates dendritic cell differentiation and/or maturation. In some embodiments, a cell (e.g., MSC) is engineered to produce at least one effector molecule that stimulates immune cell recruitment. In some embodiments, a cell (e.g., MSC) is engineered to produce at least one effector molecule that stimulates M1 macrophage signaling, activity and/or recruitment. In some embodiments, a cell (e.g., MSC) is engineered to produce at least one effector molecule that stimulates Th1 polarization. In some embodiments, a cell (e.g., MSC) is engineered to produce at least one effector molecule that stimulates stroma degradation. In some embodiments, a cell (e.g., MSC) is engineered to produce at least one effector molecule that stimulates immunostimulatory metabolite production. In some embodiments, a cell (e.g., MSC) is engineered to produce at least one effector molecule that stimulates Type I interferon signaling. In some embodiments, a cell (e.g., MSC) is engineered to produce at least one effector molecule that inhibits negative costimulatory signaling. In some embodiments, a cell (e.g., MSC) is engineered to produce at least one effector molecule that inhibits pro-apoptotic signaling (e.g., via TRAIL) of anti-tumor immune cells. In some embodiments, a cell (e.g., MSC) is engineered to produce at least one effector molecule that inhibits T regulatory ($T_{reg}$) cell signaling, activity and/or recruitment. In some embodiments, a cell (e.g., MSC) is engineered to produce at least one effector molecule that inhibits tumor checkpoint molecules. In some embodiments, a cell (e.g., MSC) is engineered to produce at least one effector molecule that activates stimulator of interferon genes (STING) signaling. In some embodiments, a cell (e.g., MSC) is engineered to produce at least one effector molecule that inhibits myeloid-derived suppressor cell signaling, activity and/or recruitment. In some embodiments, a cell (e.g., MSC) is engineered to produce at least one effector molecule that degrades immunosuppressive factors/metabolites. In some embodiments, a cell (e.g., MSC) is engineered to produce at least one effector molecule that inhibits vascular endothelial growth factor signaling. In some embodiments, a cell (e.g., MSC) is engineered to produce at least one effector molecule that directly kills tumor cells (e.g., granzyme, perforin, oncolytic viruses, cytolytic peptides and enzymes, anti-tumor antibodies, e.g., that trigger ADCC).

In some embodiments, at least one effector molecule: stimulates T cell signaling, activity and/or recruitment, stimulates antigen presentation and/or processing, stimulates natural killer cell-mediated cytotoxic signaling, activity and/or recruitment, stimulates dendritic cell differentiation and/or maturation, stimulates immune cell recruitment, stimulates macrophage signaling, stimulates stroma degradation, stimulates immunostimulatory metabolite production, or stimulates Type I interferon signaling; and at least one effector molecule inhibits negative costimulatory signaling, inhibits pro-apoptotic signaling of anti-tumor immune cells, inhibits T regulatory (Treg) cell signaling, activity and/or recruitment, inhibits tumor checkpoint molecules, activates stimulator of interferon genes (STING) signaling, inhibits myeloid-derived suppressor cell signaling, activity and/or recruitment, degrades immunosuppressive factors/metabolites, inhibits vascular endothelial growth factor signaling, or directly kills tumor cells.

In some embodiments, a cell (e.g., MSC) is engineered to produce at least one effector molecule selected from IL-12, IFN-β, IFN-γ, IL-2, IL-15, IL-7, IL-36γ, IL-18, IL-1β, OX40-ligand, and CD40L; and/or at least one effector molecule selected from anti-PD-1 antibodies, anti-PD-L1 antibodies, anti-CTLA-4 antibodies, and anti-IL-35 antibodies; and/or at least one effector molecule selected from MIP1α (CCL3), MIP1β (CCL5), and CCL21; and/or at least one effector molecule selected from CpG oligodeoxynucleotides; and/or at least one effector molecule selected from microbial peptides.

In some embodiments, a cell (e.g., MSC) is engineered to produce IFN-β and at least one effector molecule selected from cytokines, antibodies, chemokines, nucleotides, peptides, enzymes, and stimulators of interferon genes (STINGs). In some embodiments, a cell (e.g., MSC) is engineered to produce IFN-β and at least one cytokine or receptor/ligand (e.g., IL-12, IFN-γ, IL-2, IL-15, IL-7, IL-36γ, IL-18, IL-1β, OX40-ligand, and/or CD40L).

In some embodiments, a cell (e.g., MSC) is engineered to produce IFN-β and at least one cytokine or receptor/ligand (e.g., IL-12, IFN-γ, IL-2, IL-15, IL-7, IL-36γ, IL-18, IL-1β, OX40-ligand, and/or CD40L).

In some embodiments the cytokine is produced as an engineered fusion protein with an antibody, antibody-fragment, or receptor that self-binds to the cytokine to induce cell-specific targeted binding such as with IL-2 fused to an antibody fragment preventing it from binding to Treg cells and preferentially binding to CD8 and NK cells. In some embodiments, a cell (e.g., MSC) is engineered to produce IFN-β and at least one antibody (e.g., anti-PD-1 antibody, anti-PD-L1 antibody, anti-CTLA-4 antibody, anti-VEGF, anti-TGF-β, anti-IL-10, anti-TNF-α, and/or anti-IL-35 antibody). In some embodiments, a cell (e.g., MSC) is engineered to produce IFN-β and at least one chemokine (MIP1α (CCL3), MIP1β (CCL5), and/or CCL21). In some embodiments, a cell (e.g., MSC) is engineered to produce IFN-β and at least one nucleotide (e.g., a CpG oligodeoxynucleotide). In some embodiments, a cell (e.g., MSC) is engineered to produce IFN-β and at least one peptide (e.g., an anti-tumor peptide). In some embodiments, a cell (e.g., MSC) is engineered to produce IFN-β and at least one enzyme. In some embodiments, a cell (e.g., MSC) is engineered to produce IFN-β and at least one STING activator. In some embodiments, a cell (e.g., MSC) is engineered to produce IFN-β and at least one effector with direct anti-tumor activity (e.g., oncolytic virus).

In some embodiments, a cell (e.g., MSC) is engineered to produce IFN-α and MIP1-α. In some embodiments, a cell (e.g., MSC) is engineered to produce IFN-α and MIP1-β. In some embodiments, a cell (e.g., MSC) is engineered to produce IFN-α and CXCL9. In some embodiments, a cell (e.g., MSC) is engineered to produce IFN-α and CXCL10. In some embodiments, a cell (e.g., MSC) is engineered to produce IFN-α and CXCL11. In some embodiments, a cell (e.g., MSC) is engineered to produce IFN-α and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-β and MIP1-α. In some embodiments, a cell (e.g., MSC) is engineered to produce IFN-β and MIP1-β. In some embodiments, a cell (e.g., MSC) is engineered to produce IFN-β and CXCL9. In some embodiments, a cell (e.g., MSC) is engineered to produce IFN-β and CXCL10. In some embodiments, a cell (e.g., MSC) is engineered to produce IFN-β and CXCL11. In some embodiments, a cell (e.g., MSC) is engineered to produce IFN-β and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IL-12 and MIP1-α. In some embodiments, a cell (e.g., MSC) is engineered to produce IL-12 and MIP1-β. In some embodiments, a cell (e.g., MSC) is engineered to produce IL-12 and CXCL9. In some embodiments, a cell (e.g., MSC) is engineered to produce IL-12 and CXCL10. In some embodiments, a cell (e.g., MSC) is engineered to produce IL-12 and CXCL11. In some embodiments, a cell (e.g., MSC) is engineered to produce IL-12 and CCL21. In some embodiments, the cell is engineered to further produce IFN-β, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce TNF-related apoptosis-inducing ligand (TRAIL) and MIP1-α. In some embodiments, a cell (e.g., MSC) is engineered to produce TRAIL and MIP1-β. In some embodiments, a cell (e.g., MSC) is engineered to produce TRAIL and CXCL9. In some embodiments, a cell (e.g., MSC) is engineered to produce TRAIL and CXCL10. In some embodiments, a cell (e.g., MSC) is engineered to produce TRAIL and CXCL11. In some embodiments, a cell (e.g., MSC) is engineered to produce TRAIL and CCL21. In some embodiments, the cell is engineered to further produce IL-12, IFN-γ, IL-2, IL-7, IL-15, IL36-α, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a stimulator of interferon gene (STING) and MIP1-α. In some embodiments, a cell (e.g., MSC) is engineered to produce STING and MIP1-β. In some embodiments, a cell (e.g., MSC) is engineered to produce STING and CXCL9. In some embodiments, a cell (e.g., MSC) is engineered to produce STING and CXCL10. In some embodiments, a cell (e.g., MSC) is engineered to produce STING and CXCL11. In some embodiments, a cell (e.g., MSC) is engineered to produce STING and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CD40L and MIP1-α. In some embodiments, a cell (e.g., MSC) is engineered to produce CD40L and MIP1-β. In some embodiments, a cell (e.g., MSC) is engineered to produce CD40L and CXCL9. In some embodiments, a cell (e.g., MSC) is engineered to produce CD40L and CXCL10. In some embodiments, a cell (e.g., MSC) is engineered to produce CD40L and CXCL11. In some embodiments, a cell (e.g., MSC) is engineered to produce CD40L and CCL21. In some embodiments, the cell is engineered to further produce IL-12, IFN-γ, IL-2, IL-7, IL-15, IL36-γ, IL-18, and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce cytosine deaminase and MIP1-α. In some embodiments, a cell (e.g., MSC) is engineered to produce cytosine deaminase and MIP1-β. In some embodiments, a cell (e.g., MSC) is engineered to produce cytosine deaminase and CXCL9. In some embodiments, a cell (e.g., MSC) is engineered to produce cytosine deaminase and CXCL10. In some embodiments, a cell (e.g., MSC) is engineered to produce cytosine deaminase and CXCL11. In some embodiments, a cell (e.g., MSC) is engineered to produce cytosine deaminase and CCL21. In some embodiments, the cell is engineered to further produce IL-12, IFN-γ, IL-2, IL-7, IL-15, IL36-γ, IL-18, CD40L, and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-α and IL-12. In some embodiments, a cell (e.g., MSC) is engineered to produce IFN-α and IFN-γ. In some embodiments, a cell (e.g., MSC) is engineered to produce IFN-α and IL-2. In some embodiments, a cell (e.g., MSC) is engineered to produce IFN-α and IL-7. In some embodiments, a cell (e.g., MSC) is engineered to produce IFN-α and IL-15. In some embodiments, a cell (e.g., MSC) is engineered to produce IFN-α and IL-36γ. In some embodiments, a cell (e.g., MSC) is engineered to produce IFN-α and IL-18. In some embodiments, a cell (e.g., MSC) is engineered to produce IFN-α and CD40L. In some embodiments, a cell (e.g., MSC) is engineered to produce IFN-α and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-β and IL-12. In some embodiments, a cell (e.g., MSC) is engineered to produce IFN-β and IFN-γ. In some embodiments, a cell (e.g., MSC) is engineered to produce IFN-β and IL-2. In some embodiments, a cell (e.g., MSC) is engineered to produce IFN-β and IL-7. In some embodiments, a cell (e.g., MSC) is engineered to produce IFN-β and IL-15. In some embodiments, a cell (e.g., MSC) is engineered to produce IFN-β and IL-36γ. In some embodiments, a cell (e.g., MSC) is engineered to produce IFN-β and IL-18. In some embodiments, a cell (e.g., MSC) is engineered to produce IFN-β and CD40L. In some embodiments, a cell (e.g., MSC) is engineered to produce IFN-β and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce TNF-related apoptosis-inducing ligand (TRAIL) and IL-12. In some embodiments, a cell (e.g., MSC) is engineered to produce TRAIL and IFN-γ. In some embodiments, a cell (e.g., MSC) is engineered to produce TRAIL and IL-2. In some embodiments, a cell (e.g., MSC) is engineered to produce TRAIL and IL-7. In some embodiments, a cell (e.g., MSC) is engineered to produce TRAIL and IL-15. In some embodiments, a cell (e.g., MSC) is engineered to produce TRAIL and IL-36γ. In some embodiments, a cell (e.g., MSC) is engineered to produce TRAIL and IL-18. In some embodiments, a cell (e.g., MSC) is engineered to produce TRAIL and CD40L. In some embodiments, a cell (e.g., MSC) is engineered to produce TRAIL and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a stimulator of interferon gene (STING) and IL-12. In some embodiments, a cell (e.g., MSC) is engineered to produce STING and IFN-γ. In some embodiments, a cell (e.g., MSC) is engineered to produce STING and IL-2. In some embodiments, a cell (e.g., MSC) is engineered to produce STING and IL-7. In some embodiments, a cell (e.g., MSC) is engineered to produce STING and IL-15. In some embodiments, a cell (e.g., MSC) is engineered to produce STING and IL-36γ. In some embodiments, a cell (e.g., MSC) is engineered to produce STING and IL-18. In some embodiments, a cell (e.g., MSC) is engineered to produce STING and CD40L. In some embodiments, a cell (e.g., MSC) is engineered to produce STING and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CD40L and IL-12. In some embodiments, a cell (e.g., MSC) is engineered to produce CD40L and IFN-γ. In some embodiments, a cell (e.g., MSC) is engineered to produce CD40L and IL-2. In some embodiments, a cell (e.g., MSC) is engineered to produce CD40L and IL-7. In some embodiments, a cell (e.g., MSC) is engineered to produce CD40L and IL-15. In some embodiments, a cell (e.g., MSC) is engineered to produce CD40L and IL-36γ. In some embodiments, a cell (e.g., MSC) is engineered to produce CD40L and IL-18. In some embodiments, a cell (e.g., MSC) is engineered to produce CD40L and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce cytosine deaminase and IL-12. In some embodiments, a cell (e.g., MSC) is engineered to produce cytosine deaminase and IFN-γ. In some embodiments, a cell (e.g., MSC) is engineered to produce cytosine deaminase and IL-2. In some embodiments, a cell (e.g., MSC) is engineered to produce cytosine deaminase and IL-7. In some embodiments, a cell (e.g., MSC) is engineered to produce cytosine deaminase and IL-15. In some embodiments, a cell (e.g., MSC) is engineered to produce cytosine deaminase and IL-36γ. In some embodiments, a cell (e.g., MSC) is engineered to produce cytosine deaminase and IL-18. In some embodiments, a cell (e.g., MSC) is engineered to produce cytosine deaminase and CD40L. In some embodiments, a cell (e.g., MSC) is engineered to produce cytosine deaminase and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce MIP1-α and IL-12. In some embodiments, a cell (e.g., MSC) is engineered to produce MIP1-α and MIP1-γ. In some embodiments, a cell (e.g., MSC) is engineered to produce MIP1-α and IL-2. In some embodiments, a cell (e.g., MSC) is engineered to produce MIP1-α and IL-7. In some embodiments, a cell (e.g., MSC) is engineered to produce MIP1-α and IL-15. In some embodiments, a cell (e.g., MSC) is engineered to produce MIP1-α and IL-36γ. In some embodiments, a cell (e.g., MSC) is engineered to produce MIP1-α and IL-18. In some embodiments, a cell (e.g., MSC) is engineered to produce MIP1-α and CD40L. In some embodiments, a cell (e.g., MSC) is engineered to produce MIP1-α and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce MIP1-β and IL-12. In some embodiments, a cell (e.g., MSC) is engineered to produce MIP1-β and MIP1-γ. In some embodiments, a cell (e.g., MSC) is engineered to produce MIP1-β and IL-2. In some embodiments, a cell (e.g., MSC) is engineered to produce MIP1-β and IL-7. In some embodiments, a cell (e.g., MSC) is engineered to produce MIP1-β and IL-15. In some embodiments, a cell (e.g., MSC) is engineered to produce MIP1-β and IL-36γ. In some embodiments, a cell (e.g., MSC) is engineered to produce MIP1-β and IL-18. In some embodiments, a cell (e.g., MSC) is engineered to produce MIP1-β and CD40L. In some embodiments, a cell (e.g., MSC) is engineered to produce MIP1-β and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CXCL9 and IL-12. In some embodiments, a cell (e.g., MSC) is engineered to produce CXCL9 and IFN-γ. In some embodiments, a cell (e.g., MSC) is engineered to produce CXCL9 and IL-2. In some embodiments, a cell (e.g., MSC) is engineered to produce CXCL9 and IL-7. In some embodiments, a cell (e.g., MSC) is engineered to produce CXCL9 and IL-15. In some embodiments, a cell (e.g., MSC) is engineered to produce CXCL9 and IL-36γ. In some embodiments, a cell (e.g., MSC) is engineered to produce CXCL9 and IL-18. In some embodiments, a cell (e.g., MSC) is engineered to produce CXCL9 and CD40L. In some embodiments, a cell (e.g., MSC) is engineered to produce CXCL9 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a CXCL10 and IL-12. In some embodiments, a cell (e.g., MSC) is engineered to produce CXCL10 and IFN-γ. In some embodiments, a cell (e.g., MSC) is engineered to produce CXCL10 and IL-2. In some embodiments, a cell (e.g., MSC) is engineered to produce CXCL10 and IL-7. In some embodiments, a cell (e.g., MSC) is engineered to produce CXCL10 and IL-15. In some embodiments, a cell (e.g., MSC) is engineered to produce CXCL10 and IL-36γ. In some embodiments, a cell (e.g., MSC) is engineered to produce CXCL10 and IL-18. In some embodiments, a cell (e.g., MSC) is engineered to produce CXCL10 and CD40L. In some embodiments, a cell (e.g., MSC) is engineered to produce CXCL10 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L. In some embodiments, a cell (e.g., MSC) is engineered to produce CXCL11 and IL-12. In some embodiments, a cell (e.g., MSC) is engineered to produce CXCL11 and IFN-γ. In some embodiments, a cell (e.g., MSC) is engineered to produce CXCL11 and IL-2. In some embodiments, a cell (e.g., MSC) is engineered to produce CXCL11 and IL-7. In some embodiments, a cell (e.g., MSC) is engineered to produce CXCL11 and IL-15. In some embodiments, a cell (e.g., MSC) is engineered to produce CXCL11 and IL-36γ. In some embodiments, a cell (e.g., MSC) is engineered to produce CXCL11 and IL-18. In some embodiments, a cell (e.g., MSC) is engineered to produce CXCL11 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CCL21 and IL-12. In some embodiments, a cell (e.g., MSC) is engineered to produce CCL21 and IFN-γ. In some embodiments, a cell (e.g., MSC) is engineered to produce CCL21 and IL-2. In some embodiments, a cell (e.g., MSC) is engineered to produce CCL21 and IL-7. In some embodiments, a cell (e.g., MSC) is engineered to produce CCL21 and IL-15. In some embodiments, a cell (e.g., MSC) is engineered to produce CCL21 and IL-36γ. In some embodiments, a cell (e.g., MSC) is engineered to produce CCL21 and IL-18. In some embodiments, a cell (e.g., MSC) is engineered to produce CCL21 and CD40L. In some embodiments, a cell (e.g., MSC) is engineered to produce CCL21 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-α and anti-PD-L1 antibody. In some embodiments, a cell (e.g., MSC) is engineered to produce IFN-α and OX40L. In some embodiments, a cell (e.g., MSC) is engineered to produce IFN-α and anti-CTLA4 antibody. In some embodiments, a cell (e.g., MSC) is engineered to produce IFN-α and anti-CD47 antibody. In some embodiments, the cell is engineered to further produce MIP1-α, MIP1β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce IFN-β and anti-PD-L1 antibody. In some embodiments, a cell (e.g., MSC) is engineered to produce IFN-β and OX40L. In some embodiments, a cell (e.g., MSC) is engineered to produce IFN-β and anti-CTLA4 antibody. In some embodiments, a cell (e.g., MSC) is engineered to produce IFN-β and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce TRAIL and anti-PD-L1 antibody. In some embodiments, a cell (e.g., MSC) is engineered to produce TRAIL and OX40L. In some embodiments, a cell (e.g., MSC) is engineered to produce TRAIL and anti-CTLA4 antibody. In some embodiments, a cell (e.g., MSC) is engineered to produce TRAIL and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce STING and anti-PD-L1 antibody. In some embodiments, a cell (e.g., MSC) is engineered to produce STING and OX40L. In some embodiments, a cell (e.g., MSC) is engineered to produce STING and anti-CTLA4 antibody. In some embodiments, a cell (e.g., MSC) is engineered to produce STING and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CD40L and anti-PD-L1 antibody. In some embodiments, a cell (e.g., MSC) is engineered to produce CD40L and OX40L. In some embodiments, a cell (e.g., MSC) is engineered to produce CD40L and anti-CTLA4 antibody. In some embodiments, a cell (e.g., MSC) is engineered to produce CD40L and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce cytosine deaminase and anti-PD-L1 antibody. In some embodiments, a cell (e.g., MSC) is engineered to produce cytosine deaminase and OX40L. In some embodiments, a cell (e.g., MSC) is engineered to produce cytosine deaminase and anti-CTLA4 antibody. In some embodiments, a cell (e.g., MSC) is engineered to produce cytosine deaminase and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce MIP1-α and anti-PD-L1 antibody. In some embodiments, a cell (e.g., MSC) is engineered to produce MIP1-α and OX40L. In some embodiments, a cell (e.g., MSC) is engineered to produce MIP1-α and anti-CTLA4 antibody. In some embodiments, a cell (e.g., MSC) is engineered to produce MIP1-α and anti-CD47 antibody. In some embodiments, the cell is engineered to further produce IFN-α, IFN-β, TRAIL, STING, CD40L, and/or cytosine deaminase.

In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce MIP1-β and anti-PD-L1 antibody. In some embodiments, a cell (e.g., MSC) is engineered to produce MIP1-β and OX40L. In some embodiments, a cell (e.g., MSC) is engineered to produce MIP1-β and anti-CTLA4 antibody. In some embodiments, a cell (e.g., MSC) is engineered to produce MIP1-β and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL9 and anti-PD-L1 antibody. In some embodiments, a cell (e.g., MSC) is engineered to produce CXCL9 and OX40L. In some embodiments, a cell (e.g., MSC) is engineered to produce CXCL9 and anti-CTLA4 antibody. In some embodiments, a cell (e.g., MSC) is engineered to produce CXCL9 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL10 and anti-PD-L1 antibody. In some embodiments, a cell (e.g., MSC) is engineered to produce CXCL10 and OX40L. In some embodiments, a cell (e.g., MSC) is engineered to produce CXCL10 and anti-CTLA4 antibody. In some embodiments, a cell (e.g., MSC) is engineered to produce CXCL10 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL11 and anti-PD-L1 antibody. In some embodiments, a cell (e.g., MSC) is engineered to produce CXCL11 and OX40L. In some embodiments, a cell (e.g., MSC) is engineered to produce CXCL11 and anti-CTLA4 antibody. In some embodiments, a cell (e.g., MSC) is engineered to produce CXCL11 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CCL21 and anti-PD-L1 antibody. In some embodiments, a cell (e.g., MSC) is engineered to produce CCL21 and OX40L. In some embodiments, a cell (e.g., MSC) is engineered to produce CCL21 and anti-CTLA4 antibody. In some embodiments, a cell (e.g., MSC) is engineered to produce CCL21 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce IL-12 and anti-PD-L1 antibody. In some embodiments, a cell (e.g., MSC) is engineered to produce IL-12 and OX40L. In some embodiments, a cell (e.g., MSC) is engineered to produce IL-12 and anti-CTLA4 antibody. In some embodiments, a cell (e.g., MSC) is engineered to produce IL-12 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IFN-γ and anti-PD-L1 antibody. In some embodiments, a cell (e.g., MSC) is engineered to produce IFN-γ and OX40L. In some embodiments, a cell (e.g., MSC) is engineered to produce IFN-γ and anti-CTLA4 antibody. In some embodiments, a cell (e.g., MSC) is engineered to produce IFN-γ and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-2 and anti-PD-L1 antibody. In some embodiments, a cell (e.g., MSC) is engineered to produce IL-2 and OX40L. In some embodiments, a cell (e.g., MSC) is engineered to produce IL-2 and anti-CTLA4 antibody. In some embodiments, a cell (e.g., MSC) is engineered to produce IL-2 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-7 and anti-PD-L1 antibody. In some embodiments, a cell (e.g., MSC) is engineered to produce IL-7 and OX40L. In some embodiments, a cell (e.g., MSC) is engineered to produce IL-7 and anti-CTLA4 antibody. In some embodiments, a cell (e.g., MSC) is engineered to produce IL-7 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-15 and anti-PD-L1 antibody. In some embodiments, a cell (e.g., MSC) is engineered to produce IL-15 and OX40L. In some embodiments, a cell (e.g., MSC) is engineered to produce IL-15 and anti-CTLA4 antibody. In some embodiments, a cell (e.g., MSC) is engineered to produce IL-15 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-36-γ and anti-PD-L1 antibody. In some embodiments, a cell (e.g., MSC) is engineered to produce IL-36-γ and OX40L. In some embodiments, a cell (e.g., MSC) is engineered to produce IL-36-γ and anti-CTLA4 antibody. In some embodiments, a cell (e.g., MSC) is engineered to produce IL-36-γ and anti-CD47 antibody. In some embodiments, the cell is engineered to further produce IFN-α, IFN-β, TRAIL, STING, CD40L, and/or cytosine deaminase.

In some embodiments, the cell is engineered to further produce MIP1-α, MIP1-β, CXCL9, CXCL10, CXCL11, and/or CCL21.

In some embodiments, a cell (e.g., MSC) is engineered to produce IL-18 and anti-PD-L1 antibody. In some embodiments, a cell (e.g., MSC) is engineered to produce IL-18 and OX40L. In some embodiments, a cell (e.g., MSC) is engineered to produce IL-18 and anti-CTLA4 antibody. In some embodiments, a cell (e.g., MSC) is engineered to produce IL-18 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce CD40L and anti-PD-L1 antibody. In some embodiments, a cell (e.g., MSC) is engineered to produce CD40L and OX40L. In some embodiments, a cell (e.g., MSC) is engineered to produce CD40L and anti-CTLA4 antibody. In some embodiments, a cell (e.g., MSC) is engineered to produce CD40L and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce 41BB-L and anti-PD-L1 antibody. In some embodiments, a cell (e.g., MSC) is engineered to produce 41BB-L and OX40L. In some embodiments, a cell (e.g., MSC) is engineered to produce 41BB-L and anti-CTLA4 antibody. In some embodiments, a cell (e.g., MSC) is engineered to produce 41BB-L and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

Cell Types

The present disclosure primarily refers to mesenchymal stem cells (MSCs) (e.g., human MSCs) engineered to produce multiple effector molecules. It should be understood, however, that the present disclosure is not limited to MSCs, but rather is intended to encompass other cell types (e.g., cell types of the immune system). For example, an engineered cell (engineered to produce effector molecules), as provided herein, may be selected from natural killer (NK) cells, NKT cells, innate lymphoid cells, mast cells, eosinophils, basophils, macrophages, neutrophils, and dendritic cells, T cells (e.g., CD8+ T cells, CD4+ T cells, gamma-delta T cells, and T regulatory cells (CD4+, FOXP3+, CD25+)) and B cells. Thus, MSCs of the present disclosure, in any embodiment, may be substituted for one or more of the foregoing cell types.

In some embodiments, an engineered mesenchymal stem cell is from (e.g., obtained from or derived from) bone marrow. In some embodiments, an engineered mesenchymal stem cell is from (e.g., obtained from or derived from) adipose tissue. In some embodiments, an engineered mesenchymal stem cell is from (e.g., obtained from or derived from) an umbilical cord. In some embodiments, engineered mesenchymal stem cell is from a pluripotent stem cell (e.g., an embryonic stem cell or an induced pluripotent stem cell).

Thus, the present disclosure provides a T cell (e.g., CD8+ T cell, CD4+ T cell, gamma-delta T cell, or T regulatory cell (CD4+, FOXP3+, CD25+)) engineered to produce multiple effector molecules, at least two of which modulate different tumor-mediated immunosuppressive mechanisms. In some embodiments, a B cell is engineered to produce multiple effector molecules, at least two of which modulate different tumor-mediated immunosuppressive mechanisms. In some embodiments, a NK cell is engineered to produce multiple effector molecules, at least two of which modulate different tumor-mediated immunosuppressive mechanisms. In some embodiments, a NKT cell is engineered to produce multiple effector molecules, at least two of which modulate different tumor-mediated immunosuppressive mechanisms. In some embodiments, an innate lymphoid cell is engineered to produce multiple effector molecules, at least two of which modulate different tumor-mediated immunosuppressive mechanisms. In some embodiments, a mast cell is engineered to produce multiple effector molecules, at least two of which modulate different tumor-mediated immunosuppressive mechanisms. In some embodiments, an eosinophil is engineered to produce multiple effector molecules, at least two of which modulate different tumor-mediated immunosuppressive mechanisms. In some embodiments, a basophil is engineered to produce multiple effector molecules, at least two of which modulate different tumor-mediated immunosuppressive mechanisms. In some embodiments, a macrophage is engineered to produce multiple effector molecules, at least two of which modulate different tumor-mediated immunosuppressive mechanisms. In some embodiments, a neutrophil is engineered to produce multiple effector molecules, at least two of which modulate different tumor-mediated immunosuppressive mechanisms. In some embodiments, a dendritic cell is engineered to produce multiple effector molecules, at least two of which modulate different tumor-mediated immunosuppressive mechanisms.

In some embodiments, at least one of the effector molecules stimulates an immunostimulatory mechanism in the tumor microenvironment and/or inhibits an immunosuppressive mechanism in the tumor microenvironment.

In some embodiments, at least one of the effector molecules (a) stimulates T cell signaling, activity and/or recruitment, (b) stimulates antigen presentation and/or processing, (c) stimulates natural killer cell-mediated cytotoxic signaling, activity and/or recruitment, (d) stimulates dendritic cell differentiation and/or maturation, (e) stimulates immune cell recruitment, (f) stimulates pro-inflammatory macrophage signaling, activity and/or recruitment or inhibits anti-inflammatory macrophage signaling, activity and/or recruitment, (g) stimulates stroma degradation, (h) stimulates immunostimulatory metabolite production, (i) stimulates Type I interferon signaling, (j) inhibits negative costimulatory signaling, (k) inhibits pro-apoptotic signaling of anti-tumor immune cells, (l) inhibits T regulatory ($T_{reg}$) cell signaling, activity and/or recruitment, (m) inhibits tumor checkpoint molecules, (n) stimulates stimulator of interferon genes (STING) signaling, (o) inhibits myeloid-derived suppressor cell signaling, activity and/or recruitment, (p) degrades immunosuppressive factors/metabolites, (q) inhibits vascular endothelial growth factor signaling, and/or (r) directly kills tumor cells.

The immune system includes the innate immune system and the adaptive system, each including different types of cells with specific functions. The innate immune system comprises the cells and mechanisms that defend the host from infection by other organisms. The innate immune system, providing immediate defense against infection, recognizes and responds to a pathogen in a non-specific manner and does not provide long-lasting immunity to the host. The major functions of the innate immune system (e.g., in a vertebrate such as a mammal) include: recruiting immune cells to sites of infection through the production of chemical factors, including specialized chemical mediators called cytokines and chemokines; activating the complement cascade to identify bacteria, activate cells, and promote clearance of antibody complexes or dead cells; identifying and removing foreign substances present in organs, tissues, blood and lymph by specialized white blood cells; activating the adaptive immune system through a process known as antigen presentation; and acting as a physical and chemical barrier to infectious agents.

Components of the innate immune system include physical barriers (skin, gastrointestinal tract, respiratory tract), defense mechanisms (secretions, mucous, bile), and general immune responses (inflammation). Leukocytes (also called white blood cells) and phagocytic cells are the main cell types that function in innate immune system and response, which identify and eliminate pathogens that might cause infection.

Leukocytes are not tightly associated with a particular organ or tissue and function similarly to that of independent, single-cell organisms. Leukocytes are able to move freely and interact with and capture cellular debris, foreign particles, and invading microorganisms. Unlike many other cells in the body, most innate immune leukocytes cannot divide or reproduce on their own, but are the products of multipotent hematopoietic stem cells present in the bone marrow. Types of leukocytes include, without limitation: mast cells, basophils, eosinophils, natural kill cells (NK cells), innate lymphoid cells (ILCs), and gamma-delta T cells.

Mast cells are a type of innate immune cell that reside in connective tissue and in the mucous membranes. Mast cells are associated with wound healing and defense against pathogens, but are also often associated with allergy and anaphylaxis. When activated, mast cells rapidly release characteristic granules, rich in histamine and heparin, along with various hormonal mediators and chemokines, or chemotactic cytokines into the environment. Histamine dilates blood vessels, causing the characteristic signs of inflammation, and recruits neutrophils and macrophages.

Basophils and eosinophils are cells related to the neutrophil. When activated by a pathogen encounter, histamine-releasing basophils are important in the defense against parasites and play a role in allergic reactions, such as asthma. Upon activation, eosinophils secrete a range of highly toxic proteins and free radicals that are highly effective in killing parasites, but may also damage tissue during an allergic reaction. Activation and release of toxins by eosinophils are, therefore, tightly regulated to prevent any inappropriate tissue destruction.

Natural killer cells (NK cells) are components of the innate immune system that do not directly attack invading microbes. Rather, NK cells destroy compromised host cells, such as tumor cells or virus-infected cells, which have abnormally low levels of a cell-surface marker called MHC I (major histocompatibility complex)—a situation that can arise in viral infections of host cells. NK cells are so named because of the initial notion that they do not require activation in order to kill cells with low surface MHCI molecules.

Gamma-delta T cells exhibit characteristics that place them at the border between innate and adaptive immunity. In some instances, gamma-delta T cells may be considered a component of adaptive immunity in that they rearrange TCR genes to produce junctional diversity and develop a memory phenotype. The various subsets may also be considered part of the innate immune system where a restricted TCR or NK receptors may be used as a pattern recognition receptor. For example, large numbers of Vgamma9/Vdelta2 T cells respond rapidly to common molecules produced by microbes, and highly restricted intraepithelial Vdelta1 T cells will respond to stressed epithelial cells.

Phagocytes are innate immune cells that engulf, or 'phagocytose', pathogens or particles. To engulf a particle or pathogen, a phagocyte extends portions of its plasma membrane, wrapping the membrane around the particle until it is enveloped (the particle is now inside the cell). Once inside the cell, the invading pathogen is contained inside an endosome, which merges with a lysosome. The lysosome contains enzymes and acids that kill and digest the particle or organism. In general, phagocytes patrol the body searching for pathogens, but are also able to react to a group of highly specialized molecular signals produced by other cells, called cytokines. Types of phagocytes include, without limitation: macrophages, neutrophils, and dendritic cells.

Macrophages are large phagocytic cells, which are able to move outside of the vascular system by migrating across the walls of capillary vessels and entering the areas between cells in pursuit of invading pathogens. In tissues, organ-specific macrophages are differentiated from phagocytic cells present in the blood called monocytes. Macrophages are the most efficient phagocytes and can phagocytose substantial numbers of bacteria or other cells or microbes. The binding of bacterial molecules to receptors on the surface of a macrophage triggers it to engulf and destroy the bacteria through the generation of a "respiratory burst," causing the release of reactive oxygen species. Pathogens also stimulate the macrophage to produce chemokines, which recruit other cells to the site of infection. Macrophages that encourage inflammation are called M1 macrophages, whereas those that decrease inflammation and encourage tissue repair are called M2 macrophages.

Neutrophils, along with two other cell types (eosinophils and basophils), are known as granulocytes due to the presence of granules in their cytoplasm, or as polymorphonuclear cells (PMNs) due to their distinctive lobed nuclei. Neutrophil granules contain a variety of toxic substances that kill or inhibit growth of bacteria and fungi. Similar to macrophages, neutrophils attack pathogens by activating a respiratory burst. The main products of the neutrophil respiratory burst are strong oxidizing agents including hydrogen peroxide, free oxygen radicals and hypochlorite. Neutrophils are abundant and are usually the first cells to arrive at the site of an infection.

Dendritic cells (DCs) are phagocytic cells present in tissues that are in contact with the external environment, mainly the skin (where they are often called Langerhans cells), and the inner mucosal lining of the nose, lungs, stomach, and intestines. They are named for their resemblance to neuronal dendrites, but dendritic cells are not connected to the nervous system. Dendritic cells are very important in the process of antigen presentation, and serve as a link between the innate and adaptive immune systems.

Innate lymphoid cells (ILCs) play an important role in protective immunity and the regulation of homeostasis and inflammation. ILCs are classified based on the cytokines they produce and the transcription factors regulating their development and function. Group I ILCs produce type 1 cytokines and include natural killer cells. Group 2 ILCs produce type 2 cytokines, and Group 3 ILCs produce cytokines IL-17A and IL-22. Natural killer cells destroy compromised host cells, such as tumor cells or virus-infected cells. They can recognize stressed cells in the absence of antibodies, allowing them to react quickly to compromised host cells.

A myeloid cell is a cell that functions in the innate immune system. A myeloid cell includes, without limitation, monocytes, macrophages, neutrophils, basophils, eosinophils, erythrocytes, dendritic cells, and megakaryocytes or platelets. Lymphoid cells include T cells, B cells, and natural killer cells.

The adaptive immune system produces an adaptive immune response. An adaptive immune response, in its general form, begins with the sensitization of helper (TH, $CD4^+$) and cytotoxic ($CD8^+$) T cell subsets through their interaction with antigen presenting cells (APC) that express major histocompatibility (MHC)-class I or class II molecules associated with antigenic fragments (specific amino acid sequences derived from the antigen which bind to MHC I and/or MHC II for presentation on the cell surface). The sensitized or primed CD4+ T cells produce lymphokines that participate in the activation of B cells as well as various T cell subsets. The sensitized CD8+ T cells increase in numbers in response to lymphokines and are capable of destroying any cells that express the specific antigenic fragments associated with matching MHC-encoded class I molecules. Thus, in the course of a cancerous tumor, CTL eradicate cells expressing cancer associated or cancer specific antigens, thereby limiting the progression of tumor spread and disease development.

A "B lymphocyte" or "B cell" is a type of white blood cell. B cells function in the humoral immunity component of the adaptive immune system by secreting antibodies. B cells have two major functions: they present antigens to T cells, and more importantly, they produce antibodies to neutralize infectious microbes. Antibodies coat the surface of a pathogen and serve three major roles: neutralization, opsonization, and complement activation.

Neutralization occurs when the pathogen, because it is covered in antibodies, is unable to bind and infect host cells. In opsonization, an antibody-bound pathogen serves as a red flag to alert immune cells like neutrophils and macrophages, to engulf and digest the pathogen. Complement is a process for directly destroying, or lysing, bacteria.

Antibodies are expressed in two ways. The B-cell receptor (BCR), which sits on the surface of a B cell, is actually an antibody. B cells also secrete antibodies to diffuse and bind to pathogens. This dual expression is important because the initial problem, for instance a bacterium, is recognized by a unique BCR and activates the B cell. The activated B cell responds by secreting antibodies, essentially the BCR but in soluble form. This ensures that the response is specific against the bacterium that started the whole process.

Every antibody is unique, but they fall under general categories: IgM, IgD, IgG, IgA, and IgE. (Ig is short for immunoglobulin, which is another word for antibody.) While they have overlapping roles, IgM generally is important for complement activation; IgD is involved in activating basophils; IgG is important for neutralization, opsonization, and complement activation; IgA is essential for neutralization in the gastrointestinal tract; and IgE is necessary for activating mast cells in parasitic and allergic responses.

Memory B cell activation begins with the detection and binding of their target antigen, which is shared by their parent B cell. Some memory B cells can be activated without T cell help, such as certain virus-specific memory B cells, but others need T cell help. Upon antigen binding, the memory B cell takes up the antigen through receptor-mediated endocytosis, degrades it, and presents it to T cells as peptide pieces in complex with MHC-II molecules on the cell membrane. Memory T helper (TH) cells, typically memory follicular T helper (TFH) cells, that were derived from T cells activated with the same antigen recognize and bind these MHC-II-peptide complexes through their TCR. Following TCR-MHC-II-peptide binding and the relay of other signals from the memory TFH cell, the memory B cell is activated and differentiates either into plasmablasts and plasma cells via an extrafollicular response or enter a germinal center reaction where they generate plasma cells and more memory B cells.

Regulatory B cells (Bregs) represent a small population of B cells that participates in immuno-modulation and in suppression of immune responses. These cells regulate the immune system by different mechanisms. The main mechanism is a production of anti-inflammatory cytokine interleukin 10 (IL-10). The regulatory effects of Bregs were described in various models of inflammation, autoimmune diseases, transplantation reactions, and in anti-tumor immunity.

T cells have a variety of roles and are classified by subsets. T cells are divided into two broad categories: CD8+ T cells or CD4+ T cells, based on which protein is present on the cell's surface. T cells carry out multiple functions, including killing infected cells and activating or recruiting other immune cells.

CD8+ T cells also are called cytotoxic T cells or cytotoxic lymphocytes (CTLs). They are crucial for recognizing and removing virus-infected cells and cancer cells. CTLs have specialized compartments, or granules, containing cytotoxins that cause apoptosis (programmed cell death). Because of its potency, the release of granules is tightly regulated by the immune system.

The four major $CD4^+$ T-cell subsets are Th1, Th2, Th9, Th17, Tfh (T follicular helper) and Treg, with "Th" referring to "T helper cell." Th1 cells are critical for coordinating immune responses against intracellular microbes, especially bacteria. They produce and secrete molecules that alert and activate other immune cells, like bacteria-ingesting macrophages. Th2 cells are important for coordinating immune responses against extracellular pathogens, like helminths (parasitic worms), by alerting B cells, granulocytes, and mast cells. Th17 cells are named for their ability to produce interleukin 17 (IL-17), a signaling molecule that activates immune and non-immune cells. Th17 cells are important for recruiting neutrophils.

Regulatory T cells (Tregs) monitor and inhibit the activity of other T cells. They prevent adverse immune activation and maintain tolerance, or the prevention of immune responses against the body's own cells and antigens. Type 1 regulatory T (Tr1) cells are an inducible subset of regulatory T cells that play a pivotal role in promoting and maintaining tolerance. The main mechanisms by which Tr1 cells control immune responses are the secretion of high levels of IL-10, and the killing of myeloid cells through the release of Granzyme B. In addition, there are Th3 (TGF-beta secreting), iTreg (non-thymic Tconv converted to Treg cells), and iTR35 (IL-35 converted Tconv to Treg cells).

Memory T cells are a subset of antigen-specific T cells that persist long-term after an initial T cell response. They quickly expand to large numbers of effector T cells upon re-exposure to their cognate antigen, thus providing the immune system with "memory" against past antigens. The cancer vaccine described herein provides the immune system with "memory" against the tumor specific antigen, thereby eliciting strong immune response against newly emerged cancer cells or metastasized cancer cells.

A lymphocyte or lymphoid cell is a white blood cell in a vertebrate's adaptive immune system. Lymphocytes include natural killer cells (NK cells) (which function in cell-mediated, cytotoxic innate immunity), T cells (for cell-mediated, cytotoxic adaptive immunity), and B cells (for humoral, antibody-driven adaptive immunity).

Methods

Also provided herein are methods that include culturing the engineered MSCs (or other engineered immune cell) of the present disclosure. Methods of culturing MSCs are known. In some embodiments, MSCs are culture in growth medium (e.g., MSCGM human Mesenchymal Stem Cell Growth BULLETKIT™ Medium (serum containing), THERAPEAK™ MSCGM-CD™ Mesenchymal Stem Cell Chemically Defined Medium (serum free), or RoosterBio xeno-free MSC media).

Further provided herein are methods that include delivering, or administering, to a subject (e.g., a human subject) engineered MSCs as provided herein to produce in vivo at least one effector molecule produced by the MSCs. In some embodiments, the MSCs are administered via intravenous, intraperitoneal, intratracheal, subcutaneous, intratumoral, oral, anal, intranasal (e.g., packed in a delivery particle), or arterial (e.g., internal carotid artery) routes. Thus, the MSCs may be administered systemically or locally (e.g., to a TME).

Some methods comprise selecting a subject (or patient population) having a tumor (or cancer) and treating that subject with engineered MSCs that modulate tumor-mediated immunosuppressive mechanisms.

The engineered MSCs of the present disclosure may be used, in some instances, to treat cancer, such as ovarian cancer. Other cancers are described herein. For example, the engineered MSCs may be used to treat bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and/or uterine tumors.

The methods provided herein also include delivering a preparation of engineered cells, such as engineered MSCs. A preparation, in some embodiments, is a substantially pure preparation, containing, for example, less than 5% (e.g., less than 4%, 3%, 2%, or 1%) of cells other than MSCs. A preparation may comprise $1 \times 10^5$ cells/kg to $1 \times 10^7$ cells/kg, such as MSCs.

Additional Embodiments

1. A mesenchymal stem cell engineered to produce multiple effector molecules, at least two of which modulate different tumor-mediated immunosuppressive mechanisms; or a composition comprising mesenchymal stem cells engineered to produce multiple effector molecules that modulate tumor-mediated immunosuppressive mechanisms, optionally formulated in an effective amount to reduce the volume of a tumor in a subject.

2. The mesenchymal stem cell or composition of paragraph 1, wherein at least one of the effector molecules stimulates an immunostimulatory mechanism in the tumor microenvironment and/or inhibits an immunosuppressive mechanism in the tumor microenvironment.

3. The mesenchymal stem cell or composition of paragraph 1, wherein at least one of the effector molecules (a) stimulates T cell signaling, activity and/or recruitment, (b) stimulates antigen presentation and/or processing, (c) stimulates natural killer cell-mediated cytotoxic signaling, activity and/or recruitment, (d) stimulates dendritic cell differentiation and/or maturation, (e) stimulates immune cell recruitment, (f) stimulates pro-inflammatory macrophage signaling, activity and/or recruitment or inhibits anti-inflammatory macrophage signaling, activity and/or recruitment, (g) stimulates stroma degradation, (h) stimulates immunostimulatory metabolite production, (i) stimulates Type I interferon signaling, (j) inhibits negative costimulatory signaling, (k) inhibits pro-apoptotic signaling of anti-tumor immune cells, (l) inhibits T regulatory ($T_{reg}$) cell signaling, activity and/or recruitment, (m) inhibits tumor checkpoint molecules, (n) stimulates stimulator of interferon genes (STING) signaling, (o) inhibits myeloid-derived suppressor cell signaling, activity and/or recruitment, (p) degrades immunosuppressive factors/metabolites, (q) inhibits vascular endothelial growth factor signaling, and/or (r) directly kills tumor cells.

4. The mesenchymal stem cell or composition of any one of paragraphs 1-3 comprising an engineered nucleic acid that comprises a promoter operably linked to a nucleotide sequence encoding an effector molecule.

5. The mesenchymal stem cell or composition of any one of paragraphs 1-4 comprising: (a) an engineered nucleic acid that comprises a promoter operably linked to a nucleotide sequence encoding at least two effector molecules; or (b) at least two engineered nucleic acids, each comprising a promoter operably linked to a nucleotide sequence encoding at least one effector molecule.

6. The mesenchymal stem cell or composition of any one of paragraphs 1-5, wherein the tumor is selected from bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and uterine tumors.

7. The mesenchymal stem cell or composition of any one of paragraphs 1-6, wherein at least one of the effector molecules produced by the mesenchymal stem cell or composition is selected from cytokines, receptors/ligands, antibodies, nucleotides, peptides, and enzymes.

8. The mesenchymal stem cell or composition of paragraph 7, wherein the cytokines are selected from chemokines, interferons, interleukins, lymphokines, and tumor necrosis factors.

9. The mesenchymal stem cell or composition of paragraph 8, wherein the chemokines are selected from MIP1a (CCL3), MIP1b (CCL5), CCL21, CXCL9, CXCL10 and CXCL11.

10. The mesenchymal stem cell or composition of paragraph 8 or 9, wherein the interferons are selected from IFN-β and IFN-γ.

11. The mesenchymal stem cell or composition of any one of paragraphs 8-10, wherein the interleukins are selected from the IL-12, IFN-β, IFN-γ, IL-2, IL-15, IL-7, IL-36γ, IL-18, and IL-1β.

12. The mesenchymal stem cell or composition of any one of paragraphs 7-11, wherein the receptors/ligands are selected from OX40-ligand and CD40L.

13. The mesenchymal stem cell or composition of any one of paragraphs 7-12, wherein the antibodies are selected from checkpoint inhibitors and anti-IL-35 antibodies.

14. The mesenchymal stem cell or composition of paragraph 13, wherein the checkpoint inhibitors are selected from anti-PD-1 antibodies, anti-PD-L1 antibodies, and anti-CTLA-4 antibodies.

15. The mesenchymal stem cell or composition of any one of paragraphs 7-14, wherein the nucleotides are selected from CpG oligodeoxynucleotides.

16. The mesenchymal stem cell or composition of any one of paragraphs 7-15, wherein the peptide is an anti-tumor peptide.

17. The mesenchymal stem cell or composition of any one of paragraphs 7-16, wherein the enzymes are selected from enzymes that degrade stroma, enzymes that degrade immunosuppressive metabolites, and enzymes that stimulate immunostimulatory metabolite production.

18. The mesenchymal stem cell or composition of any one of paragraphs 1-17, wherein at least one of the effector molecules is IFN-β, and wherein at least one of the effector molecules is selected from cytokines, antibodies, chemokines, nucleotides, enzymes, and oncolytic viruses.

19. The mesenchymal stem cell or composition of any one of paragraphs 1-18, wherein at least one of the effector molecules stimulates an inflammatory pathway in the tumor microenvironment, and/or at least one of the effector molecules inhibits a negative regulator of inflammation in the tumor microenvironment.

20. The mesenchymal stem cell or composition of paragraph 19, wherein the inflammatory pathway is a TNF Receptor Superfamily pathway, a common gamma-chain family pathway, or a Toll-Like Receptor pathway.

21. The mesenchymal stem cell or composition of paragraph 19 or 20, wherein the negative regulator of inflammation is Stat3, Bruton's tyrosine kinase, c-kit, or SOCS-1.

22. The mesenchymal stem cell or composition of any one of paragraphs 1-21, wherein the mesenchymal stem cell or composition is engineered to produce a homing molecule.

23. The mesenchymal stem cell or composition of paragraph 22, wherein the homing molecule is selected from: CCR9, CXCR3, CXCR4, CCR2, CCR4, FPR2, VEGFR, IL6R, CXCR1, CSCR7, and PDGFR.

24. The mesenchymal stem cell or composition of any one of paragraphs 4-23, wherein the promoter is an inducible promoter.

25. The mesenchymal stem cell or composition of any one of paragraphs 4-23, wherein the promoter is a CMV promoter, an EF1a promoter, an EFS promoter, a MND promoter, a PGK promoter, a SFFV promoter, a SV40 promoter, or a UbC promoter.

26. The mesenchymal stem cell or composition of any one of paragraphs 2-22, wherein the promoter is a synthetic promoter, optionally comprising a transcription factor binding domain.

27. The mesenchymal stem cell or composition of any one of paragraphs 2-26, wherein the promoter is modulated by a local tumor state.

28. The mesenchymal stem cell or composition of paragraph 27, wherein the local tumor state is hypoxia.

29. The mesenchymal stem cell or composition of paragraph 27, wherein the local tumor state is inflammation.

30. The mesenchymal stem cell or composition of paragraph 25, wherein inducible promoter comprises a phloretin-adjustable control element (PEACE) or a zinc-finger DNA-binding domain (DBD).

31. The mesenchymal stem cell or composition of any one of paragraphs 1-30, wherein the mesenchymal stem cell or composition is from bone marrow, adipose tissue, umbilical cord, or pluripotent stem cells.

32. The mesenchymal stem cell or composition of any one of paragraphs 1-31, wherein the mesenchymal stem cell or composition is engineered to produce IL-12 and CCL21.

33. The mesenchymal stem cell or composition of paragraph 32, wherein the mesenchymal stem cell or composition is engineered to produce IFN-β and/or IFN-γ.

34. The mesenchymal stem cell or composition of paragraph 32 or 33, wherein the mesenchymal stem cell or composition is engineered to produce an anti-CD40 antibody and/or an anti-CTLA4 antibody.

35. A method comprising culturing the mesenchymal stem cell of any one of paragraphs 1-34 to produce the effector molecules.

36. A method comprising delivering to a subject the mesenchymal stem cell or the composition of any one of paragraphs 1-34 to produce in vivo at least one effector molecule produced by the mesenchymal stem cell.

37. The method of paragraph 36, wherein the at least one effector molecule is produced in a tumor microenvironment of the subject.

38. A method of treating a cancer, comprising delivering to a subject diagnosed with a cancer the mesenchymal stem cell or the composition of any one of paragraphs 1-34.

39. The method of paragraph 38, wherein the cancer is ovarian cancer.

40. The method of paragraph 38, wherein the cancer is breast cancer.

41. The method of paragraph 38, wherein the cancer is colon cancer.

42. The method of any one of paragraphs 36-41 further comprising administering to the subject an anti-CD40 antibody and/or and anti-CTLA4 antibody.

43. A method of treating breast cancer in a subject, comprising delivering to a subject having a breast tumor a therapeutically effective amount of a preparation of mesenchymal stem cells engineered to produce IL-12 and CCL21.

44. The method of paragraph 43, wherein the preparation further comprises an anti-CD40 antibody and/or an anti-CTLA4 antibody.

45. The method of paragraph 43 further comprising administering to the subject an anti-CD40 antibody and/or an anti-CTLA4 antibody.

46. The method of any one of paragraphs 43-45, wherein the preparation comprises a pharmaceutically acceptable carrier and/or pharmaceutically acceptable excipient.

47. The method of any one of paragraphs 43-46, wherein the therapeutically effective amount reduces the volume of the breast tumor by at least 20%.

48. The method of paragraph 47, wherein the volume of the breast tumor is reduced by at least 20% within 14 days of delivering the preparation to the subject.

49. The method of paragraph 48, wherein the volume of the breast tumor is reduced by at least 20% within 7 days of delivering the preparation to the subject.

50 The method of any one of paragraphs 43-46, wherein the therapeutically effective amount reduces the volume of the breast tumor by at least 50%.

51. The method of paragraph 47, wherein the volume of the breast tumor is reduced by at least 50% within 14 days of delivering the preparation to the subject.

52. The method of paragraph 48, wherein the volume of the breast tumor is reduced by at least 50% within 7 days of delivering the preparation to the subject.

53. A method of treating colon cancer in a subject, comprising delivering to a subject having a colon tumor a therapeutically effective amount of a preparation of mesenchymal stem cells engineered to produce IL-12 and CCL21.

54. The method of paragraph 53, wherein the preparation further comprises an anti-CD40 antibody and/or an anti-CTLA4 antibody.

55. The method of paragraph 53 further comprising administering to the subject an anti-CD40 antibody and/or an anti-CTLA4 antibody.

56. The method of any one of paragraphs 53-55, wherein the preparation comprises a pharmaceutically acceptable carrier and/or pharmaceutically acceptable excipient.
57. The method of any one of paragraphs 53-56, wherein the therapeutically effective amount reduces the volume of the colon tumor by at least 20%.
58. The method of paragraph 57, wherein the volume of the colon tumor is reduced by at least 20% within 14 days of delivering the preparation to the subject.
59. The method of paragraph 58, wherein the volume of the colon tumor is reduced by at least 20% within 7 days of delivering the preparation to the subject.
60 The method of any one of paragraphs 53-56, wherein the therapeutically effective amount reduces the volume of the colon tumor by at least 50%.
61. The method of paragraph 57, wherein the volume of the colon tumor is reduced by at least 50% within 14 days of delivering the preparation to the subject.
62. The method of paragraph 58, wherein the volume of the colon tumor is reduced by at least 50% within 7 days of delivering the preparation to the subject.

EXAMPLES

Example 1

This Example describes engineering mesenchymal stem cells (MSCs) to express human immunotherapy (hIT) payloads (hMSC-hIT) and mouse MSCs (mMSCs) to express mouse immunotherapy (mIT) payloads (mMSC-mIT). DNA encoding human and murine immuno-modulatory genes (anti-PD1 antibody, anti-CTLA4 antibody, CCL21, IL2, IL12, IL15, and constitutively active STING (stimulator of interferon genes; Woo S R, et al. (2015) *Trends Immunol* 36(4):250-256) mutant) are synthesized, cloned into expression vectors, introduced into their respective mouse and human MSCs, and their expression characterized. DNA encoding the immuno-modulatory genes is then expressed in MSCs in combination with IFN-β.

Methods:

Genes encoding immunotherapy payloads that have different mechanisms of action are synthesized: 1) checkpoint inhibitors, 2) chemokines, 3) cytokines, and 4) STING (stimulator of interferon genes) pathway modulators (Woo S R, et al. (2015) Trends Immunol 36(4):250-256). For checkpoint inhibitors, anti-PD1 and anti-CTLA4 antibodies are expressed. For chemokines, CCL21, which is known to mediate trafficking of dendritic cells, CD4+ T cells, and CD8+ T cells (Dubinett S M, et al. (2010) Cancer J 16(4): 325-335) are expressed. For cytokines, IL2, IL12, and IL15 are expressed. For STING pathway modulators, an intracellular STING mutant that is constitutively active (Tang E D & Wang C Y (2015) PLoS One 10(3):e0120090) is expressed. Both mouse and human versions of the immunotherapies (mIT and hIT, respectively) are used. Additional effector molecules tested include: IL1beta, IFN-gamma, IL17, as well as IL7 (Cieri N, et al. (2013) Blood 121(4): 573-584).

These genes are encoded downstream of the CMV promoter to achieve a high level of expression. As shown in FIG. 1, GFP can be expressed at high levels in MSCs using electroporated plasmids (nucleofection technology) with the CMV promoter. The plasmids are nucleofected into MSCs. Human bone-marrow-derived MSCs (hMSCs) are purchased from commercial sources. Mouse MSCs (mMSCs) are derived from femur bone marrow (Kidd S, et al. (2009) Stem Cells 27(10):2614-2623).

Expression of the secreted therapeutic payloads is confirmed using ELISA or bead-based multiplex assays with commercially available antibodies that recognize the payloads. Alternatively, the payloads are fused with a Myc tag, and anti-Myc antibodies are used for labeling. For the constitutive STING mutant, reporter plasmids that express luciferase from the IFN-beta promoter are used to confirm activation (Fitzgerald K A, et al. (2003) Nat Immunol 4(5):491-496). Functional testing of the payloads is also carried out and described in greater detail in Example 2.

Figure 2:
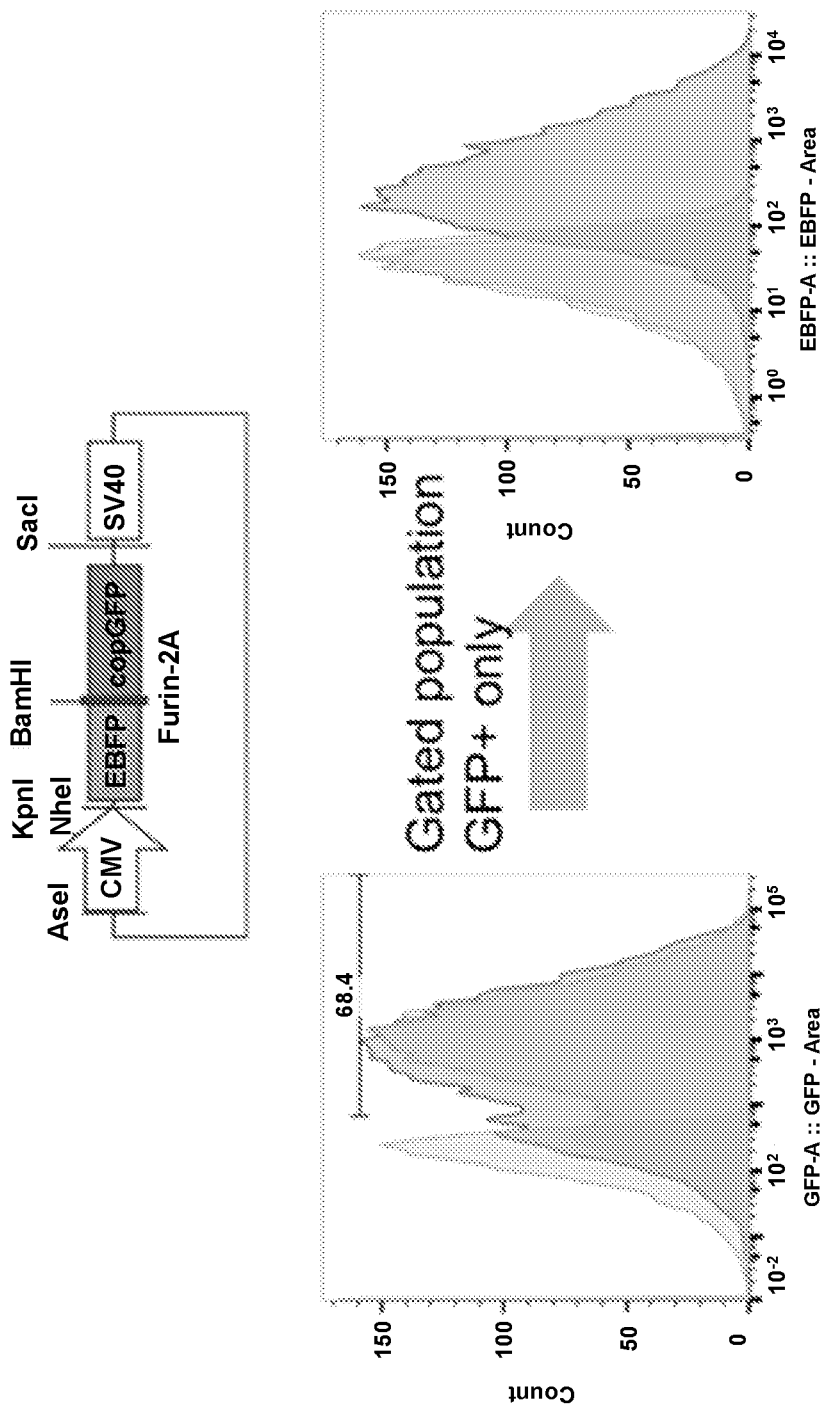
FIG. 2 shows a 2A expression vector design and flow cytometry histograms showing dual expression of "effector 1" (BFP) and "effector 2" (GFP). Left plot: The second peak histogram (medium gray) represent cells containing the BFP-2A-GFP construct, the third peak histogram (dark gray) represent cells containing the GFP expressing construct only, and the first peak histogram (light gray) represent untransfected cells. Right plot: The third peak histogram (medium gray) represent cells containing the BFP-2A-GFP construct, the second peak histogram (light gray) represent cells containing the GFP expressing construct only, and the first peak histogram (medium gray) represent untransfected cells. The shifted curve in the right plot indicates that the 2A design yields GFP cells are also co-expressing BFP.

Next, these immunotherapy payloads are expressed in combination with IFN-beta. One of the goals is to identify effectors that have additive or synergistic activity with IFN-beta against ovarian cancer cells. Two strategies are used to express combinatorial immunotherapy payloads from MSCs. (1) MSCs are nucleofected with two plasmids, one that expresses a payload from the list above and the other that encodes IFN-beta, thus resulting in a mixed population of cells expressing these genes. (2) Plasmids that co-express both a payload from the list above and IFN-beta are constructed within a single vector. Three architectures are used for this approach: (i) a single promoter that expresses the payload and IFN-beta, which are separated by a 2A 'ribosome skipping' tag (FIG. 2); (ii) a single promoter that expresses the payload and IFN-beta, which are separated by an Internal Ribosome Entry Site (IRES); and (iii) two promoters are used to independently drive the expression of a payload and IFN-beta. Distinct promoters are used express the payloads and IFN-beta (e.g., SFFV, CMV, and/or MND promoters). Different combinations of these promoters and terminating sequences are evaluated to identify configurations that express both payloads.

These strategies are tested and the expression levels of the immunotherapy payloads and IFN-beta are evaluated. Survival of the MSCs is also evaluated. CMV, SFFV, and MND promoters have already been validated in MSCs.

As an alternative to plasmid transfection and electroporation, lentiviral vectors may be used to transduce payload expression constructs into MSCs. Lentiviral vectors can be used to express GFP in MSCs (data not shown). Lentivirally engineered MSCs should be translationally viable and primed for upcoming clinical trials (Deng P, et al. (2016) Neural Regen Res 11(5):702-705; Beegle J R, et al. (2016) Mol Ther Methods Clin Dev 3:16053). In some embodiments, expression constructs may be introduced into MSCs using transposons, integrated using PhiC31 into genomic pseudosites, or using nucleases, such as zinc fingers (ZFs), clustered regularly interspaced short palindromic repeats (CRISPR), or transcription activator-like effector nucleases (TALENs).

An additional strategy that can be pursued for combinatorial immunotherapy expression is to construct one plasmid per payload, independently nucleofect each plasmid into an MSC population, and mix the resulting cell populations. Alternatively, the payloads can be encoded onto lentiviruses and multiple lentiviruses genomically integrated into MSCs.

Example 2

This Example describes the in vitro characterization of MSCs with individual and combination immunotherapy payloads. Direct anti-cancer effects of immunotherapy-expressing MSCs on cancer cells are first measured. Next, the effects of immunotherapy-expressing MSCs on co-cultures with primary immune cells (focusing on T cells) and cancer cells are measured. The immuno-stimulatory properties of immunotherapy-expressing MSCs are rank-ordered based on inflammatory biomarker panels in both mouse and human cell systems. Immunotherapy-expressing MSCs that significantly enhance cancer cell killing either on their own or together with T cells are identified, and the top candidates to advance to in vivo testing are selected.

Methods:

The immunotherapy-expressing MSCs from Example 1 are evaluated for their functional effects using in vitro models relevant to cancer therapy. Human ovarian cancer cells (e.g., OVCAR8 and SKOV3) and human immune cells isolated from circulating PBMCs are used to test the hMSCs expressing hITs. Mouse ovarian cancer cells (e.g., ID8) and mouse immune cells are used to test the mMSCs expressing mITs.

Checkpoint Inhibitors.

Cell-binding assays are used to verify the activity of the expressed antibodies. The targets of the antibodies, CTLA4 and PD1, both negatively regulate T cells, but they are upregulated at different stages of T-cell activation (Boutros C, et al. (2016) Nat Rev Clin Oncol 13(8):473-486; Valsecchi M E (2015) New Engl J Med 373(13):1270-1270). CTLA4 is briefly upregulated in the priming phase, whereas PD1 is consistently expressed in the effector phase of T cell activation (Pardoll D M (2012) Nat Rev Cancer 12(4):252-264; Legat A, et al. (2013) Front Immunol 4:455). Anti-CTLA4 antibody binds to CTLA4 on the T-cell surface, blocking CTLA4 from shutting down T-cell activation in the early stage, and the human anti-PD1 antibody binds to PD1, preventing tumor cells from inhibiting T-cell activity.

T cells are isolated from PBMC by negative selection using EASYSEP™ magnetic bead (STEMCELL Technologies). The isolated T cells are activated by Human T-Activator CD3/28 Dynabeads (Thermo Fisher) and expression of CTLA-4 and PD-1 is monitored over 5 days to select for optimal timing of expression for each surface marker. On the appropriate days, conditioned media from the MSCs expressing antibodies for CTLA-4 or PD-1, or control conditioned media from non-expressing MSCs, are applied to the activated T cells to validate direct cell-surface-receptor binding of these antibodies. Fluorochrome-labeled secondary detection antibodies together with flow cytometry should confirm binding.

Chemokines.

CCL21 chemokine functionality is confirmed using cell migration assays and isolated naive T cells, which express chemokine receptor CCR7 that is responsive to CCL21 chemotaxis. Specifically, CCL21-expressing or control MSCs are added to one compartment of a trans-well and then cell migration is assessed by isolated naive T cells from the other compartment, followed by enumeration of numbers of migrated T cells (Justus C R, et al. (2014) J Vis Exp (88)).

Cytokines.

The activity of IL2, IL12, and IL15 is measured. ELISA assays specific to IL2, IL12, and IL15 are used to detect levels of these cytokines in MSC supernatants. Functional bioactivity assays employ the CTLL-2 cell line to assess of IL2 or IL15-mediated proliferation, or the NKG cell line to assess IL12-mediated IFN-gamma production by MSC supernatants. Multiplexed cytokine profiling assays using LUMINEX® technology may also be used to assess cytokine expression and effects on immune cells.

Sting Pathway.

STING pathway activation is measured with the constitutive STING mutant payload. Using LUMINEX® beads, the secretion of Type I interferons (e.g. IFN-alpha2 and IFN-beta) with expression of the STING mutant are profiled in MSCs.

Direct Effects of Immunotherapy-Expressing MSCs on Ovarian Cancer Cells.

Any direct effects of MSCs on ovarian cancer cell growth and viability are tested in vitro. For example, mMSC or hMSC candidates are co-cultured with the mouse ovarian cancer cell line (ID8) or human ovarian cancer cell lines (OVCAR8 and SKOV3) and cancer cell cytotoxicity is measured by the well-characterized lactate dehydrogenase (LDH) assay. After 24 hours of co-culture, the supernatants are collected and measured for LDH levels correlated to cellular death via an enzymatic reaction that is subsequently quantified by specific absorbance on a plate reader. Additionally, cancer cell numbers are assessed by counting live versus dead cells by Trypan Blue exclusion and live versus apoptotic/dead cells by flow cytometric measurement using Annexin-V and propidium iodide staining.

Effects of Immunotherapy-Expressing MSCs on T Cell and Ovarian Cancer Cell Co-Culture Systems.

Tests determine whether immunotherapy-expressing MSCs can stimulate immune cells, such as T cells, to have improved anti-cancer activity against ovarian cancer cells in vitro. Specifically, mMSC-mIT candidates are co-cultured with mouse splenocytes and the ID8 cancer cell line, or hMSC-hIT candidates are co-cultured with human PBMCs and the OVCAR8 or SKOV3 cell lines. The co-culture assays entail using PBMCs/splenocytes with the ovarian cancer cells, with or without the MSCs, and stimulation with anti-CD3/28 beads. To assess cancer cell death, 16 hour killing assays are performed using techniques such as LDH cytotoxicity measurements, combining dye-labeled ovarian cancer cells with non-labeled effector PBMCs/splenocytes at fixed ratios and assaying killing by flow cytometry (Jedema I, et al. (2004) Blood 103(7):2677-2682), and apoptosis readouts by flow cytometry using Annexin-V with propidium iodide. T cell activation/proliferation is specifically assay by CFSE cell division at 3-5 days and cytokine production of IFN-gamma at 1-3 days.

An alternative strategy to generate T cells expressing CTLA-4 and PD1 is to activate with phytohaemagglutinin (PHA) to express the cell surface receptors PD1 and CTLA4. On Day 3, ~99% of the activated T cells should express PD1 while ~15% of them should express CTLA4 (Pardoll D M (2012) Nat Rev Cancer 12(4):252-264; Legat A, et al. (2013) Front Immunol 4:455). On Day 10, the activated T cells should be in the effector phase, when CTLA4 expression is downregulated but PD1 expression is maintained. Direct cell-surface-receptor binding of these antibodies is evaluated. On Day 3 and Day 10 post-induction, MSCs with the respective checkpoint inhibitor antibody expression constructs are applied to the T cell cultures. Labeled detection antibodies are used together with flow cytometry to confirm binding. Commercial antibodies are used as controls.

Example 3

This Example describes the in vivo characterization of MSCs expressing immunotherapy payloads in a syngeneic ovarian cancer model. The anti-tumor efficacy of immunotherapy-expressing MSCs is characterized using syngeneic mouse models of ovarian cancer (mMSC-mIT with mouse immune system). Tumor homing of engineered MSCs and expression of individual and combinatorial immunotherapies in a syngeneic ovarian mouse model are measured.

Ovarian tumor burden and mouse survival with engineered MSC treatments are also measured. This Example should demonstrate selective homing of engineered MSCs to the TME and localized production of immunotherapy factors in ovarian tumors versus other body sites. This Example should also demonstrate significant reductions in tumor burden and extension of mouse survival with immunotherapy-expressing engineered MSCs.

Methods:

The mouse ID8 cell line originated from spontaneous transformation of mouse ovarian epithelial surface cells (MOSE), is used to create a syngeneic ovarian tumor model (Roby K F, et al. (2000) Carcinogenesis 21(4):585-591). The ID8 cell line is infected with a lentivirus expressing *Renilla* luciferase (rLuc) to allow for in vivo bioluminescence imaging that is orthogonal to MSCs expressing Firefly luciferase (ffLuc). Successful rLuc expression is confirmed in ID8 in vitro prior to establishing the syngeneic ovarian cancer model in mice. For the syngeneic model, $5\times10^5$ ID8 cells are injected into the peritoneal cavity of C57BL/6 mice between 6 to 8 weeks old (36, 54). MSCs are nucleofected with the payload expressing plasmids from Example 1, along with an ffLuc-expressing plasmid.

mMSC-mIT candidates are introduced into the syngeneic mouse model starting on day 25 (after tumor cell injection) at a dose of $10^6$ MSC per animal once per week for 5 weeks (Dembinski J L, et al. (2013) *Cytotherapy* 15(1):20-32). The ovarian tumor load and mMSC-mIT candidates are visualized over time through rLuc and ffLuc bioluminescence imaging, respectively, as well as histological analyses following terminal time points. Mice are euthanized when they develop signs of distress, such as body-weight loss, ruffled fur, poor body posture, distended abdomen, and jaundice. Survival curves for the mice are measured. Distal metastasis of tumor cells is quantified by bioluminescence imaging (BLI) and by necropsy at time of euthanasia. Immune system profiling and activity is measured at different time points as biomarkers of response to the therapy.

To assess for variability in the expected anti-tumor effects of the MSCs, the dose of ID8 cells used to establish the model is varied (e.g., increase the number of cells to $5\times10^6$), the dose of MSCs used is changed, and the time when MSCs are delivered after tumor establishment is modulated.

Even though mMSCs have been shown to home to ovarian tumors in mouse models, it is possible that some payloads disrupt this homing activity. In these instances, expression of these payloads may be engineered to be inducible. This can be achieved, for example, with a phloretin-inducible system (Gitzinger M, et al. (2009) *Proc Natl Acad Sci USA* 106(26):10638-10643). Alternatively, the Dimerizer system may be used to link a synthetic zinc-finger DNA-binding domain with a transactivator domain using a small molecule (Clackson T, et al. (1998) *Proc Natl Acad Sci USA* 95(18):10437-10442). Alternatively or additionally, inducible payload expression constructs that are triggered in the tumor microenvironment based on signals such as low 02 may be constructed.

Lentiviral ffLuc constructs may also be used to infect MSCs.

Example 4

This Example describes the in vivo characterization of the efficacy of MSCs expressing immunotherapy payloads in xenograft models of human ovarian cancer in mice with human immune cells. The activity of engineered MSCs in human ovarian cancer models in immunodeficient mice that are engrafted with human immune cells via CD34+ cell transplants (hMSC-hIT with humanized immune system) is tested. Homing of engineered MSCs and expression of individual and combinatorial immunotherapies in human xenograft ovarian tumors in mice with human immune cells are measured. Ovarian tumor burden and mouse survival with engineered MSC treatments are also tested. This Example should demonstrate elevated homing of engineered MSCs and localized production of immunotherapy factors into human xenograft ovarian tumors versus other body sites in mice. This Example should also demonstrate significant reductions in tumor burden and extension of mouse survival with immunotherapy-expressing engineered MSCs correlating with changes in the immune system composition.

Methods.

To enable translation of engineered MSCs into human clinical trials, hMSC-hIT constructs are tested in humanized mouse models of human cancers. The effects of the immunotherapy-expressing hMSCs in mice are modeled by using xenografts of human ovarian cancer cell lines in immunodeficient mice (NSG) engrafted with CD34+ hematopoietic stem cells (HSCs).

For human ovarian cancer cells, OVCAR8 and SKOV3 cell lines are used. Similar assays as described in Example 3 are used to investigate tumor load and mouse survival over time.

Two alternative approaches may also be used. (1) Human T cells can be infused into the mice. (2) Human PBMCs can be infused into the mice.

Expression Vector: pL+MCS (SEQ ID NO: 8)

```
ACGCGTGTAGTCTTATGCAATACTCTTGTAGTCTTGCAACATGGTAACGATGAGTTAGCAACATGC

CTTACAAGGAGAGAAAAAGCACCGTGCATGCCGATTGGTGGAAGTAAGGTGGTACGATCGTGCCT

TATTAGGAAGGCAACAGACGGGTCTGACATGGATTGGACGAACCACTGAATTGCCGCATTGCAGA

GATATTGTATTTAAGTGCCTAGCTCGATACAATAAACGGGTCTCTCTGGTTAGACCAGATCTGAGC

CTGGGAGCTCTCTGGCTAACTAGGGAACCCACTGCTTAAGCCTCAATAAAGCTTGCCTTGAGTGCT

TCAAGTAGTGTGTGCCCGTCTGTTGTGTGACTCTGGTAACTAGAGATCCCTCAGACCCTTTTAGTCA

GTGTGGAAAATCTCTAGCAGTGGCGCCCGAACAGGGACCTGAAAGCGAAAGGGAAACCAGAGCT

CTCTCGACGCAGGACTCGGCTTGCTGAAGCGCGCACGGCAAGAGGCGAGGGCGGCGACTGGTGA

GTACGCCAAAAATTTTGACTAGCGGAGGCTAGAAGGAGAGAGATGGGTGCGAGAGCGTCAGTATT
```

-continued

```
AAGCGGGGAGAATTAGATCGCGATGGGAAAAAATTCGGTTAAGGCCAGGGGGAAAGAAAAAAT
ATAAATTAAAACATATAGTATGGGCAAGCAGGGAGCTAGAACGATTCGCAGTTAATCCTGGCCTG
TTAGAAACATCAGAAGGCTGTAGACAAATACTGGGACAGCTACAACCATCCCTTCAGACAGGATC
AGAAGAACTTAGATCATTATATAATACAGTAGCAACCCTCTATTGTGTGCATCAAAGGATAGAGAT
AAAAGACACCAAGGAAGCTTTAGACAAGATAGAGGAAGAGCAAACAAAAGTAAGACCACCGCA
CAGCAAGCGGCCACTGATCTTCAGACCTGGAGGAGGAGATATGAGGGACAATTGGAGAAGTGAAT
TATATAAATATAAAGTAGTAAAAATTGAACCATTAGGAGTAGCACCCACCAAGGCAAAGAGAAGA
GTGGTGCAGAGAGAAAAAAGAGCAGTGGGAATAGGAGCTTTGTTCCTTGGGTTCTTGGGAGCAGC
AGGAAGCACTATGGGCGCAGCCTCAATGACGCTGACGGTACAGGCCAGACAATTATTGTCTGGTA
TAGTGCAGCAGCAGAACAATTTGCTGAGGGCTATTGAGGCGCAACAGCATCTGTTGCAACTCACA
GTCTGGGCATCAAGCAGCTCCAGGCAAGAATCCTGGCTGTGGAAAGATACCTAAAGGATCAACA
GCTCCTGGGGATTTGGGGTTGCTCTGGAAAACTCATTTGCACCACTGCTGTGCCTTGGAATGCTAG
TTGGAGTAATAAATCTCTGGAACAGATTGGAATCACACGACCTGGATGGAGTGGGACAGAGAAAT
TAACAATTACACAAGCTTAATACACTCCTTAATTGAAGAATCGCAAAACCAGCAAGAAAAGAATG
AACAAGAATTATTGGAATTAGATAAATGGGCAAGTTTGTGGAATTGGTTTAACATAACAAATTGG
CTGTGGTATATAAAATTATTCATAATGATAGTAGGAGGCTTGGTAGGTTTAAGAATAGTTTTTGCT
GTACTTTCTATAGTGAATAGAGTTAGGCAGGGATATTCACCATTATCGTTTCAGACCCACCTCCCA
ACCCCGAGGGGACCCGACAGGCCCGAAGGAATAGAAGAAGAAGGTGGAGAGAGAGACAGAGAC
AGATCCATTCGATTAGTGAACGGATCTCGACGGTATCGGTTAACTTTTAAAAGAAAAGGGGGGAT
TGGGGGGTACAGTGCAGGGGAAAGAATAGTAGACATAATAGCAACAGACATACAAACTAAAGAA
TTACAAAAACAAATTACAAAAATCAAAATTTTATCTCGACATGGTGGCGACCGGTAGCGCTAGCG
GATCGATAAGCTTGATATCGCCTGCAGCCGAATTCCTTGACTTGGGATCCGCGTCAAGTGGAGCAA
GGCAGGTGGACAGTCCTGCAGGCATGCGTGACTGACTGAGGCCGCGACTCTAGTTTAAACTGCGT
GACTGACTCTAGAAGATCCGGCAGTGCGGCCGCGTCGACAATCAACCTCTGGATTACAAAATTTGT
GAAAGATTGACTGGTATTCTTAACTATGTTGCTCCTTTTACGCTATGTGGATACGCTGCTTTAATGC
CTTTGTATCATGCTATTGCTTCCCGTATGGCTTTCATTTTCTCCTCCTTGTATAAATCCTGGTTGCTG
TCTCTTTATGAGGAGTTGTGGCCCGTTGTCAGGCAACGTGGCGTGGTGTGCACTGTGTTTGCTGAC
GCAACCCCCACTGGTTGGGGCATTGCCACCACCTGTCAGCTCCTTTCCGGGACTTTCGCTTTCCCCC
TCCCTATTGCCACGGCGGAACTCATCGCCGCCTGCCTTGCCCGCTGCTGGACAGGGGCTCGGCTGT
TGGGCACTGACAATTCCGTGGTGTTGTCGGGGAAATCATCGTCCTTTCCTTGGCTGCTCGCCTGTGT
TGCCACCTGGATTCTGCGCGGGACGTCCTTCTGCTACGTCCCTTCGGCCCTCAATCCAGCGGACCTT
CCTTCCCGCGGCCTGCTGCCGGCTCTGCGGCCTCTTCCGCGTCTTCGCCTTCGCCCTCAGACGAGTC
GGATCTCCCTTTGGGCCGCCTCCCCGCCTGGTACCTTTAAGACCAATGACTTACAAGGCAGCTGTA
GATCTTAGCCACTTTTTAAAAGAAAAGGGGGGACTGGAAGGGCTAATTCACTCCCAACGAAAATA
AGATCTGCTTTTTGCTTGTACTGGGTCTCTCTGGTTAGACCAGATCTGAGCCTGGGAGCTCTCTGGC
TAACTAGGGAACCCACTGCTTAAGCCTCAATAAAGCTTGCCTTGAGTGCTTCAAGTAGTGTGTGCC
CGTCTGTTGTGTGACTCTGGTAACTAGAGATCCCTCAGACCCTTTTAGTCAGTGTGGAAAATCTCTA
GCAGTAGTAGTTCATGTCATCTTATTATTCAGTATTTATAACTTGCAAAGAAATGAATATCAGAGA
GTGAGAGGAACTTGTTTATTGCAGCTTATAATGGTTACAAATAAAGCAATAGCATCACAAATTTCA
CAAATAAAGCATTTTTTTCACTGCATTCTAGTTGTGGTTTGTCCAAACTCATCAATGTATCTTATCA
TGTCTGGCTCTAGCTATCCCGCCCCTAACTCCGCCCAGTTCCGCCCATTCTCCGCCCCATGGCTGAC
```

-continued

```
TAATTTTTTTTATTTATGCAGAGGCCGAGGCCGCCTCGGCCTCTGAGCTATTCCAGAAGTAGTGAG

GAGGCTTTTTTGGAGGCCTAGACTTTTGCAGAGACGGCCCAAATTCGTAATCATGGTCATAGCTGT

TTCCTGTGTGAAATTGTTATCCGCTCACAATTCCACACAACATACGAGCCGGAAGCATAAAGTGTA

AAGCCTGGGGTGCCTAATGAGTGAGCTAACTCACATTAATTGCGTTGCGCTCACTGCCCGCTTTCC

AGTCGGGAAACCTGTCGTGCCAGCTGCATTAATGAATCGGCCAACGCGCGGGGAGAGGCGGTTTG

CGTATTGGGCGCTCTTCCGCTTCCTCGCTCACTGACTCGCTGCGCTCGGTCGTTCGGCTGCGGCGAG

CGGTATCAGCTCACTCAAAGGCGGTAATACGGTTATCCACAGAATCAGGGGATAACGCAGGAAAG

AACATGTGAGCAAAAGGCCAGCAAAAGGCCAGGAACCGTAAAAAGGCCGCGTTGCTGGCGTTTTT

CCATAGGCTCCGCCCCCCTGACGAGCATCACAAAAATCGACGCTCAAGTCAGAGGTGGCGAAACC

CGACAGGACTATAAAGATACCAGGCGTTTCCCCCTGGAAGCTCCCTCGTGCGCTCTCCTGTTCCGA

CCCTGCCGCTTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGTAAGACACGA

CTTATCGCCACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGGACAGTATTTGGTATCTGCGCTC

TGCTGAAGCCAGTTACCTTCGGAAAAAGAGTTGGTAGCTCTTGATCCGGCAAACAAACCACCGCT

GGTAGCGGTGGTTTTTTTGTTTGCAAGCAGCAGATTACGCGCAGAAAAAAAGGATCTCAAGAAGA

TCCTTTGATCTTTTCTACGGGGTCTGACGCTCAGTGGAACGAAAACTCACGTTAAGGGATTTTGGT

CATGAGATTATCAAAAAGGATCTTCACCTAGATCCTTTTAAATTAAAAATGAAGTTTTAAATCAAT

CTAAAGTATATATGAGTAAACTTGGTCTGACAGTTACCAATGCTTAATCAGTGAGGCACCTATCTC

AGCGATCTGTCTATTTCGTTCATCCATAGTTGCCTGACTCCCCGTCGTGTAGATAACTACGATACGG

GAGGGCTTACCATCTGGCCCCAGTGCTGCAATGATACCGCGAGACCCACGCTCACCGGCTCCAGAT

TTATCAGCAATAAACCAGCCAGCCGGAAGGGCCGAGCGCAGAAGTGGTCCTGCAACTTTATCCGC

CTCCATCCAGTCTATTAATTGTTGCCGGGAAGCTAGAGTAAGTAGTTCGCCAGTTAATAGTTTGCG

CAACGTTGTTGCCATTGCTACAGGCATCGTGGTGTCACGCTCGTCGTTTGGTATGGCTTCATTCAGC

TCCGGTTCCCAACGATCAAGGCGAGTTACATGATCCCCCATGTTGTGCAAAAAAGCGGTTAGCTCC

TTCGGTCCTCCGATCGTTGTCAGAAGTAAGTTGGCCGCAGTGTTATCACTCATGGTTATGGCAGCA

CTGCATAATTCTCTTACTGTCATGCCATCCGTAAGATGCTTTTCTGTGACTGGTGAGTACTCAACCA

AGTCATTCTGAGAATAGTGTATGCGGCGACCGAGTTGCTCTTGCCCGGCGTCAATACGGGATAATA

CCGCGCCACATAGCAGAACTTTAAAAGTGCTCATCATTGGAAAACGTTCTTCGGGGCGAAAACTCT

CAAGGATCTTACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCGCAAAAAAG

GGAATAAGGGCGACACGGAAATGTTGAATACTCATACTCTTCCTTTTTCAATATTATTGAAGCATT

TATCAGGGTTATTGTCTCATGAGCGGATACATATTTGAATGTATTTAGAAAAATAAACAAATAGGG

GTTCCGCGCACATTTCCCCGAAAAGTGCCACCTGACGTCTAAGAAACCATTATTATCATGACATTA

ACCTATAAAAATAGGCGTATCACGAGGCCCTTTCGTCTCGCGCGTTTCGGTGATGACGGTGAAAAC

CTCTGACACATGCAGCTCCCGGAGACGGTCACAGCTTGTCTGTAAGCGGATGCCGGGAGCAGACA

AGCCCGTCAGGGCGCGTCAGCGGGTGTTGGCGGGTGTCGGGGCTGGCTTAACTATGCGGCATCAG

AGCAGATTGTACTGAGAGTGCACCATATGCGGTGTGAAATACCGCACAGATGCGTAAGGAGAAAA

TACCGCATCAGGCGCCATTCGCCATTCAGGCTGCGCAACTGTTGGGAAGGGCGATCGGTGCGGGC
```

-continued
CTCTTCGCTATTACGCCAGCTGGCGAAAGGGGGATGTGCTGCAAGGCGATTAAGTTGGGTAACGC

CAGGGTTTTCCCAGTCACGACGTTGTAAAACGACGGCCAGTGCCAAGCTG

Example 5. 4T1 Triple Negative Breast Carcinoma

In the following experiments, MSCs were engineered to express one of the following effector molecules, then administered, alone or in combinations, to an orthotopic breast cancer mouse model: IFNβ, IFNγ, IL12, IL15, IL36γ, IL7, TRAIL, cGAS, CCL21a, OX40L, CD40L, or HACv-PD1. In some examples, a checkpoint inhibitor (anti-CD40, anti-PD1, or anti-CTLA-4 antibody) was injected in combination with administration with the engineered MSCs.

MSC Homing

Figure 3:
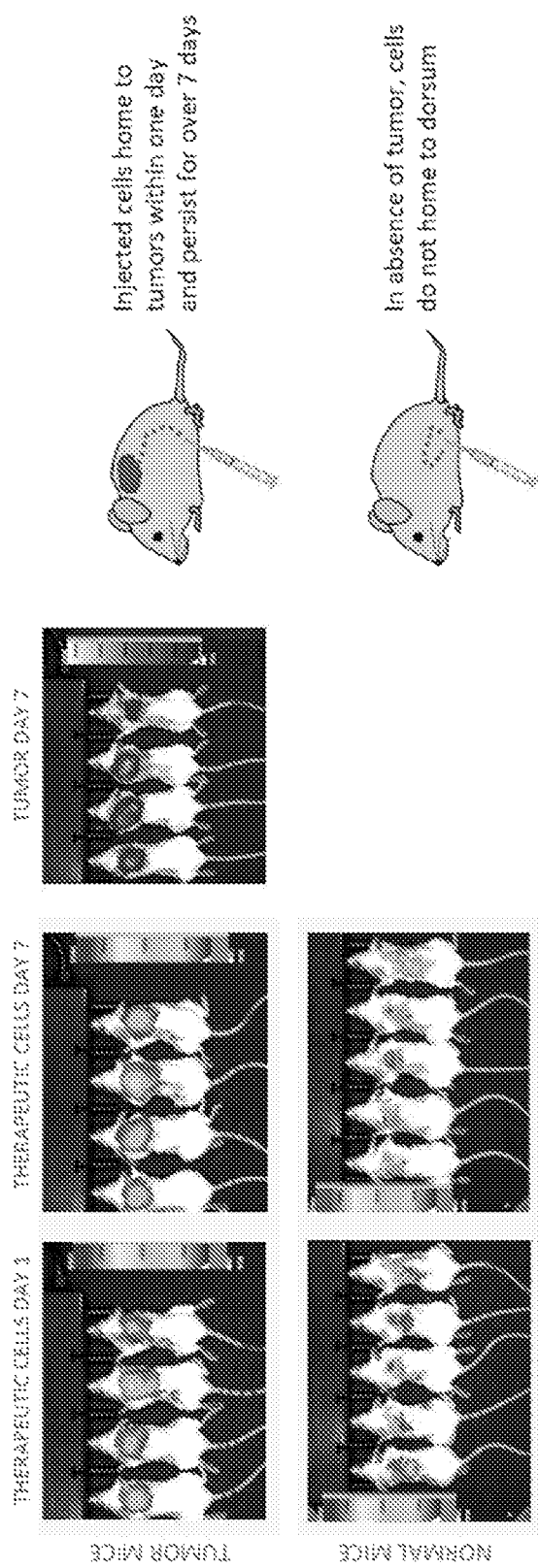
FIG. 3 shows data indicating that intraperitoneally injected murine BM-derived MSCs (BM-MSCs) home to the tumor site of 4T1 breast cancer cells in vivo. Fluorescently labeled BM-MSCs (therapeutic cells) were injected into mice bearing 4T1 breast tumor cells. The breast tumor cells express a luciferase reporter. The first top two panels on the left show imaging of therapeutic cells (BM-MSCs) in mice bearing tumors on day 1 and on day 7 after injection as indicated. The third top panel on the left shows imaging of tumor cells in mice bearing tumors on day 7 after injection. The bottom two panels on the left show imaging of therapeutic cells in normal mice not bearing tumors on day 1 and on day 7 after injection as indicated. A schematic showing the effect of tumors on homing of therapeutic cells is provided on the far right.

The following experiments demonstrate that murine MSCs home to tumors in an orthotopic mouse model of breast cancer. Luciferase-expressing 4T1 breast tumor cells ($5 \times 10^5$) were orthotopically implanted into the dorsal fat pad of female BALB/cJ mice. After 5 days, mice were intraperitoneally injected with 1 million fluorescently-labeled (with XenoLight DiR (Caliper Life Sciences)) murine BM-derived MSCs (BM-MSCs, therapeutic cells). At days 1 and 7 after MSC injection, fluorescence analysis was used to determine MSC localization using the Ami HT live animal imager (Spectral Instruments). On day 7, tumor localization and size was determined through the 4T1 cell's luciferase bioluminescence reporter using the Ami HT imager. As shown in FIG. 3, the injected MSCs co-localized to the site of the tumor, indicating that these cells do in fact specifically home in vivo to sites of 4T1 breast tumors. The injected MSCs home to tumors within one day and persist for over 7 days. In contrast, injected MSCs do not home to the dorsum in the absence of tumor in normal mice. These results suggest that MSCs can be used as a delivery vehicle for anti-cancer molecules, proteins or compounds.

Figure 11A:
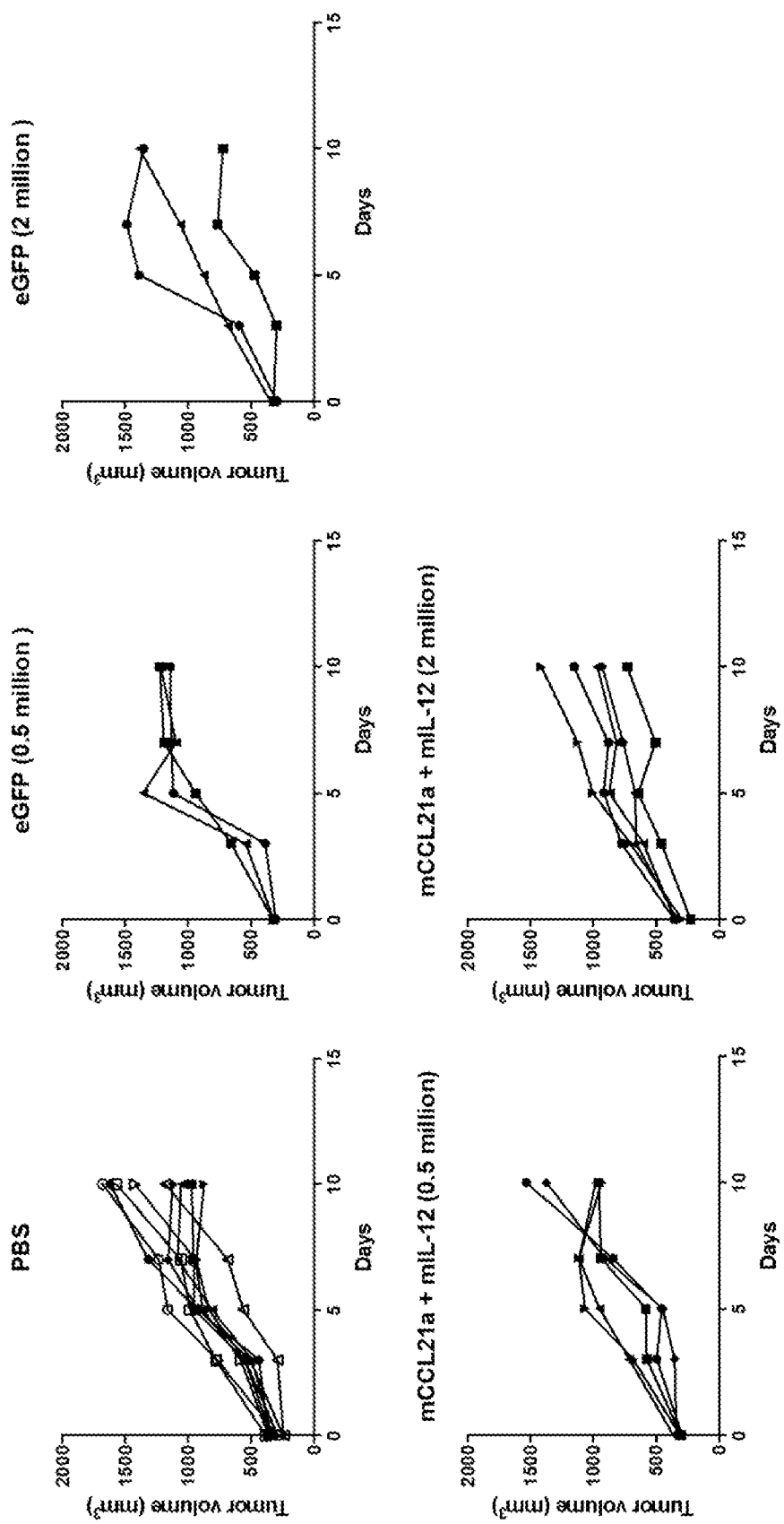
FIG. 11A shows that engineered human MSCs do not home to mouse 4T1 tumors.
Figure 11B:
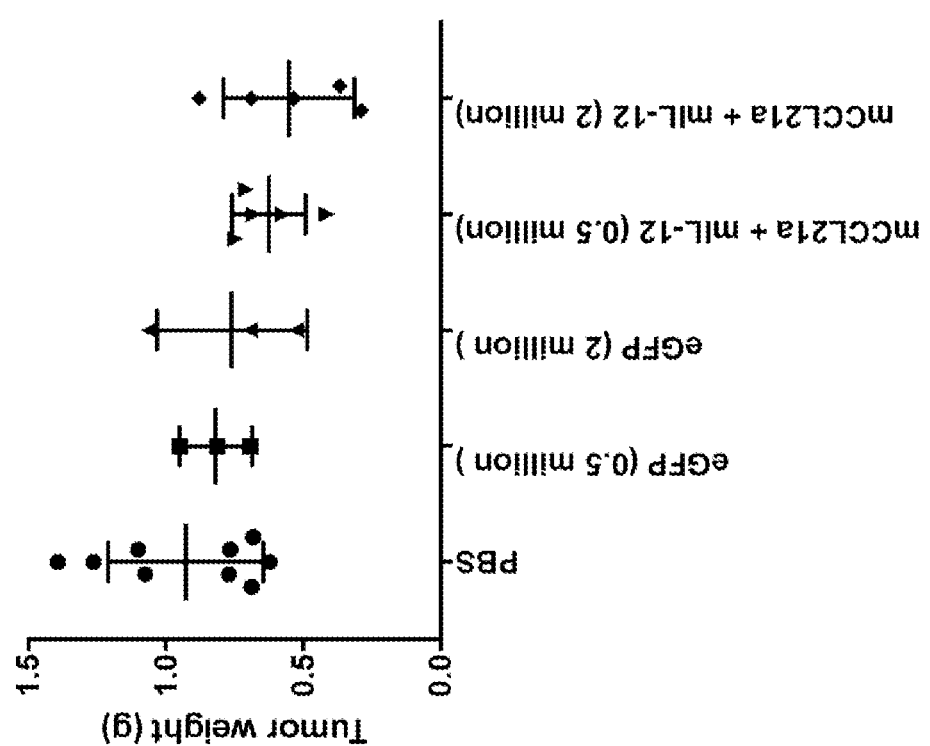
FIG. 11B shows the tumor weight for individual mice in each treatment. Efficacy was determined by tumor volume from caliper measurement every other day.

To determine whether engineered human MSCs can home toward mouse tumors, different lines of engineered human MSC expressing either GFP, IL2 or CCL21a were injected into BALB/c mice with 4T1 tumors. Efficacy was determined by tumor volume from caliper measurement every other day. FIGS. 11A-11B show that human MSCs do not home to mouse 4T1 tumors.

In Vivo Efficacy

The following experiments demonstrate the in vivo efficacy of MSCs expressing immunotherapy effectors (payloads) in the orthotopic model of breast cancer. 4T1-Neo-Fluc mouse breast tumor cells (Imanis Life Sciences, $5 \times 10^5$ cells) were implanted orthotopically into the dorsal fat pad of female BALB/cJ mice (The Jackson Laboratory). Mice were then randomized into the treatment groups 5 days after tumor implantation. Mice received intraperitoneal injection of either control MSC growth media or engineered MSCs ($2 \times 10^6$ cells) expressing different immunotherapy effectors (payloads) once a week for two weeks. Each immunotherapy was expressed by a different MSC, and MSCs were combined (1:1 ratio) for combinatorial treatment. Tumor growth was monitored by caliper measurements every other day, and mouse weights were recorded twice weekly. Mice were euthanized 14 days after first MSC treatment and tissues were collected for further analysis.

Figure 4:
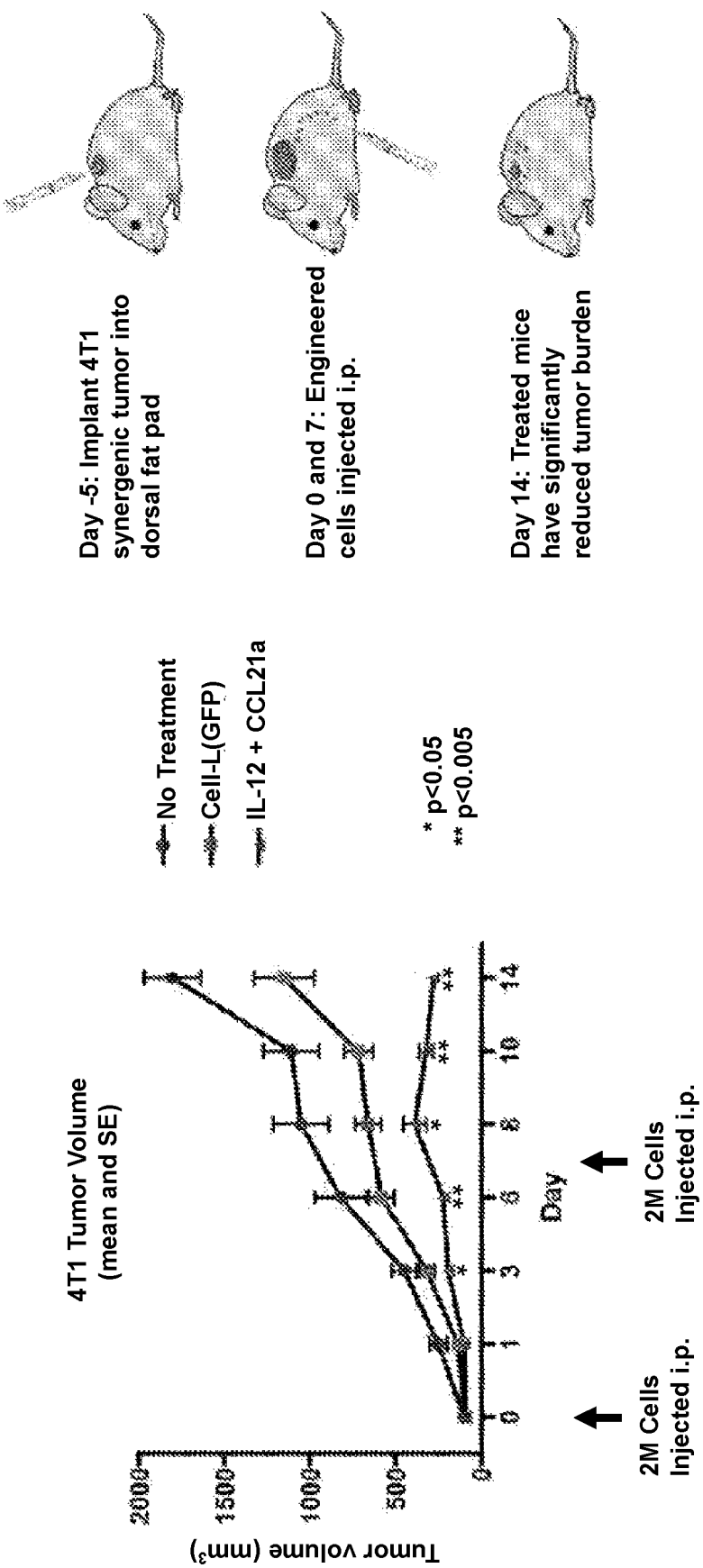
FIG. 4 shows data indicating that engineered MSCs expressing IL-12 and CCL21a induced significant tumor growth delay in an orthotopic mouse model of breast cancer. The chart on the left shows the effects of engineered MSCs on 4T1 breast tumor growth in mice (n=8). Each line in the chart represents tumor volume in mice receiving intraperitoneal injection of either control MSC growth media or engineered MSCs on day 0 and day 7. Mice received intraperitoneal injection of engineered MSCs expressing IL-12 and engineered MSCs expressing CCL21a. Tumor volume was determined by caliper measurements every other day. Data represent mean±SEM. *p<0.05, **p<0.005 as compared to control media group. The schematic on the right shows a timeline of treatment and the effect of engineered MSCs expressed combinatorial genes IL-12 and CCL21a on tumor burden in treated mice.

FIG. 4 shows that tumor growth was delayed in mice treated with engineered MSCs expressed combinatorial genes IL-12 and CCL21a compared to controls treated with media.

Figure 5A:
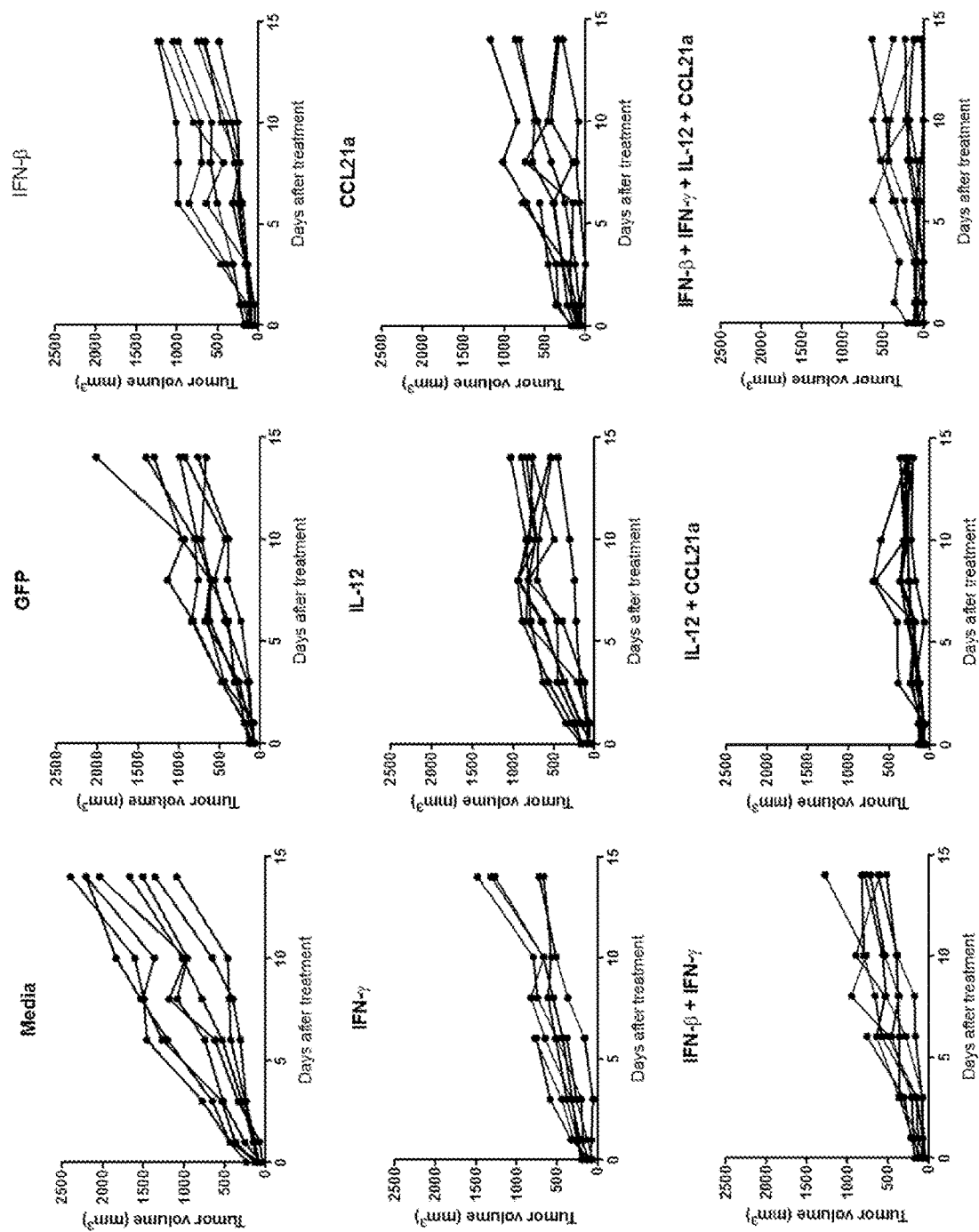
FIG. 5A includes data indicating that engineered MSCs expressing IFN-β, IFN-γ, IL-12, CCL21a, or combinations thereof inhibit tumor growth in an orthotopic mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 5A represents an individual mouse. The left graph of FIG. 5B shows the tumor weight for individual mice in each treatment on day 14. The right graph of FIG. 5B shows the tumor volume represented as mean±SEM for mice receiving each treatment over time.
Figure 5B:
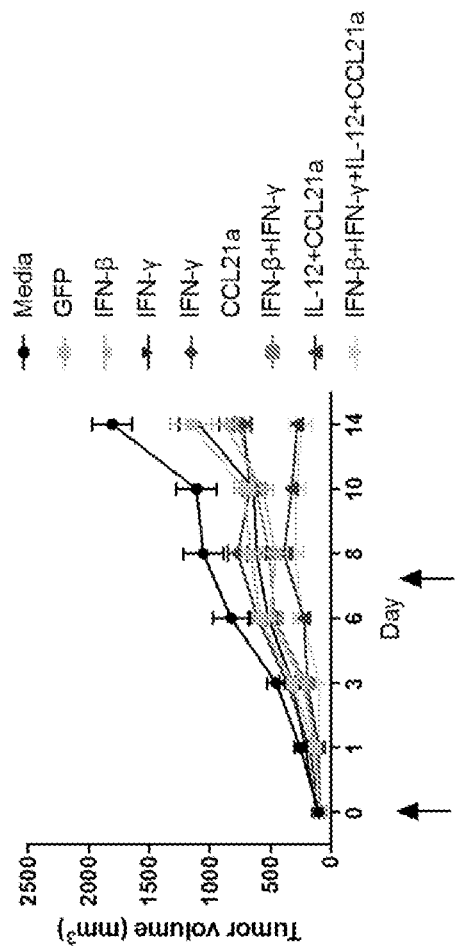
Figure 5B:
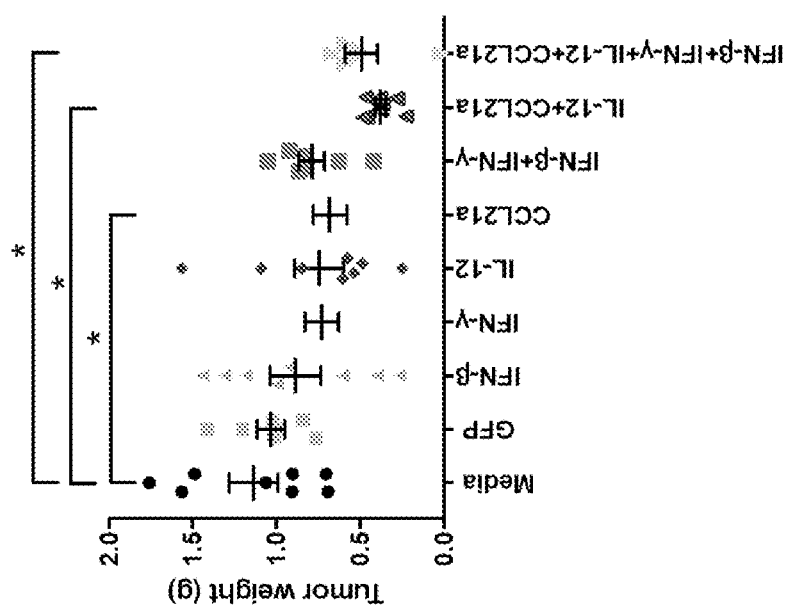

FIGS. 5A-5C show that engineered MSCs that express single immunotherapy effectors (e.g., IFN-β, IFN-γ, IL-12 or CCL21a) inhibited growth of syngeneic 4T1 mouse tumors compared to media-treated mice. Surprisingly, a synergistic effect on tumor growth was observed when the immunotherapy effectors were combined, particularly the combination of IL-12 and CCL21a, and the combination of IFN-β, IFN-γ, IL-12 and CCL21a (FIGS. 5A-5C).

Figure 6A:
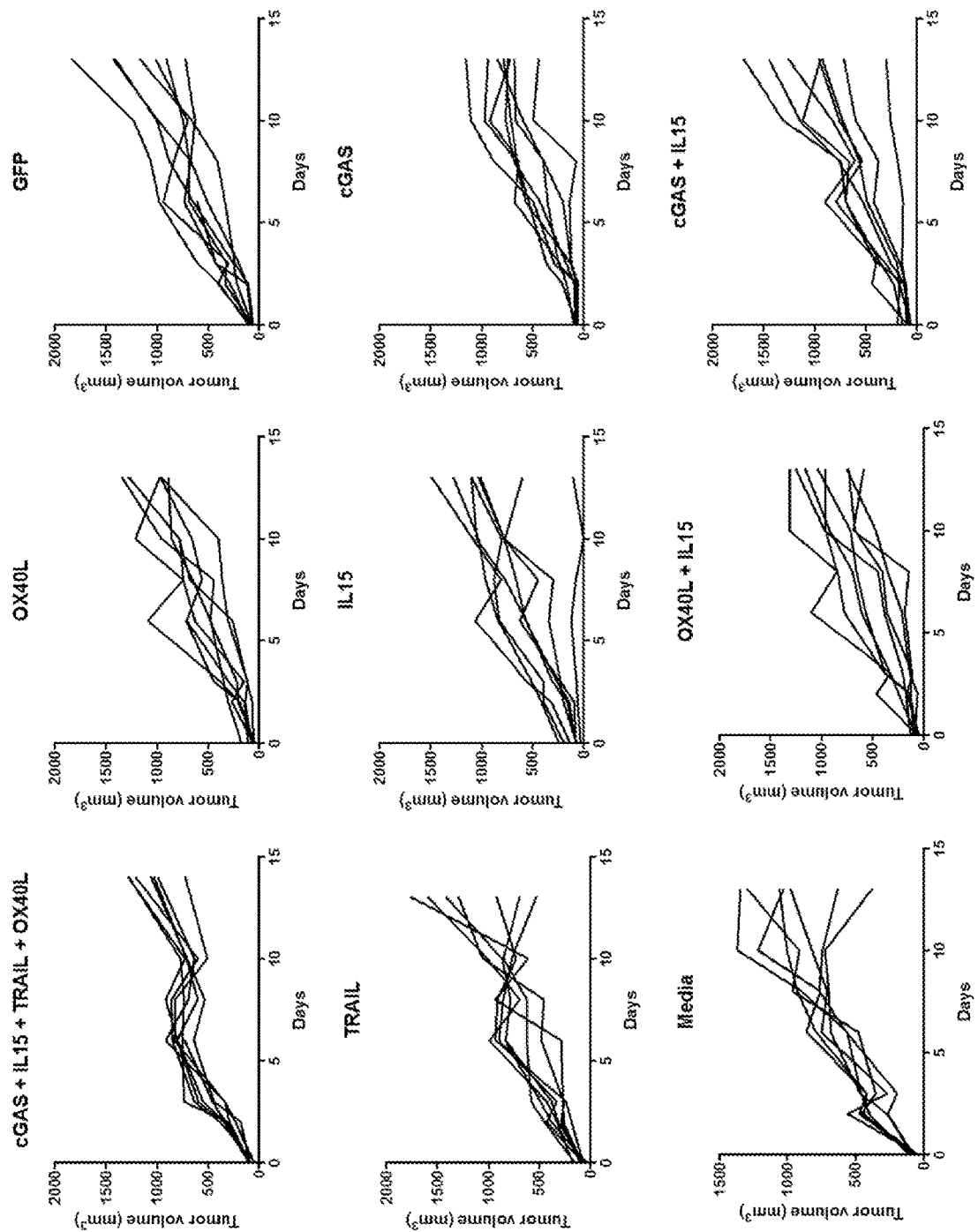
FIG. 6A includes data indicating that engineered MSCs expressing OX40L, TRAIL, IL15, cGAS, or combinations thereof do not inhibit tumor growth significantly in an orthotopic mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 6A represents an individual mouse. The left graph of FIG. 6B shows the tumor weight for individual mice in each treatment. The right graph of FIG. 6B shows body weight represented as mean±SEM for mice receiving each treatment over time.
Figure 6B:
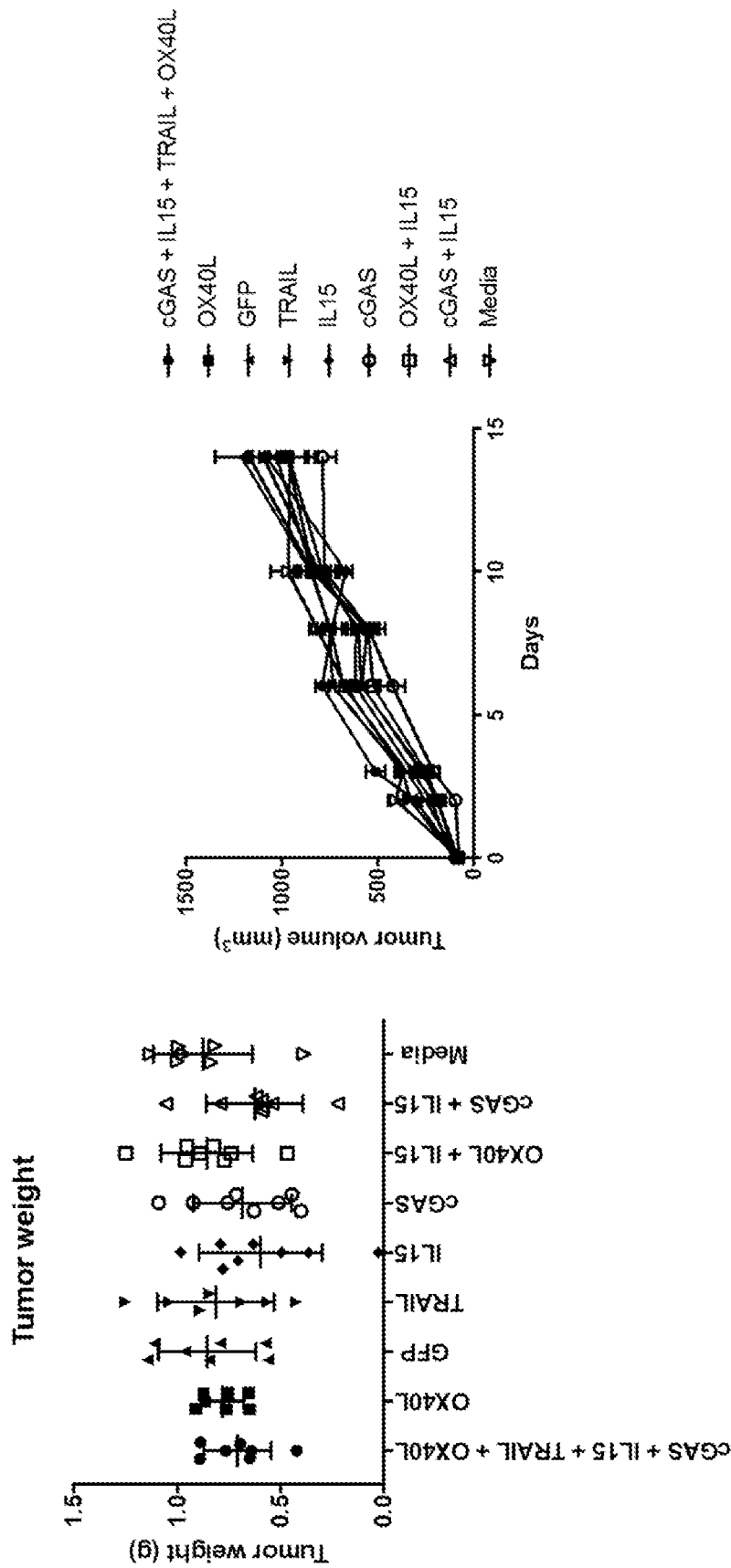

FIGS. 6A-6B show that engineered MSCs expressing OX40L, TRAIL, IL15, cGAS, or combinations thereof do not inhibit tumor growth.

Figure 7A:
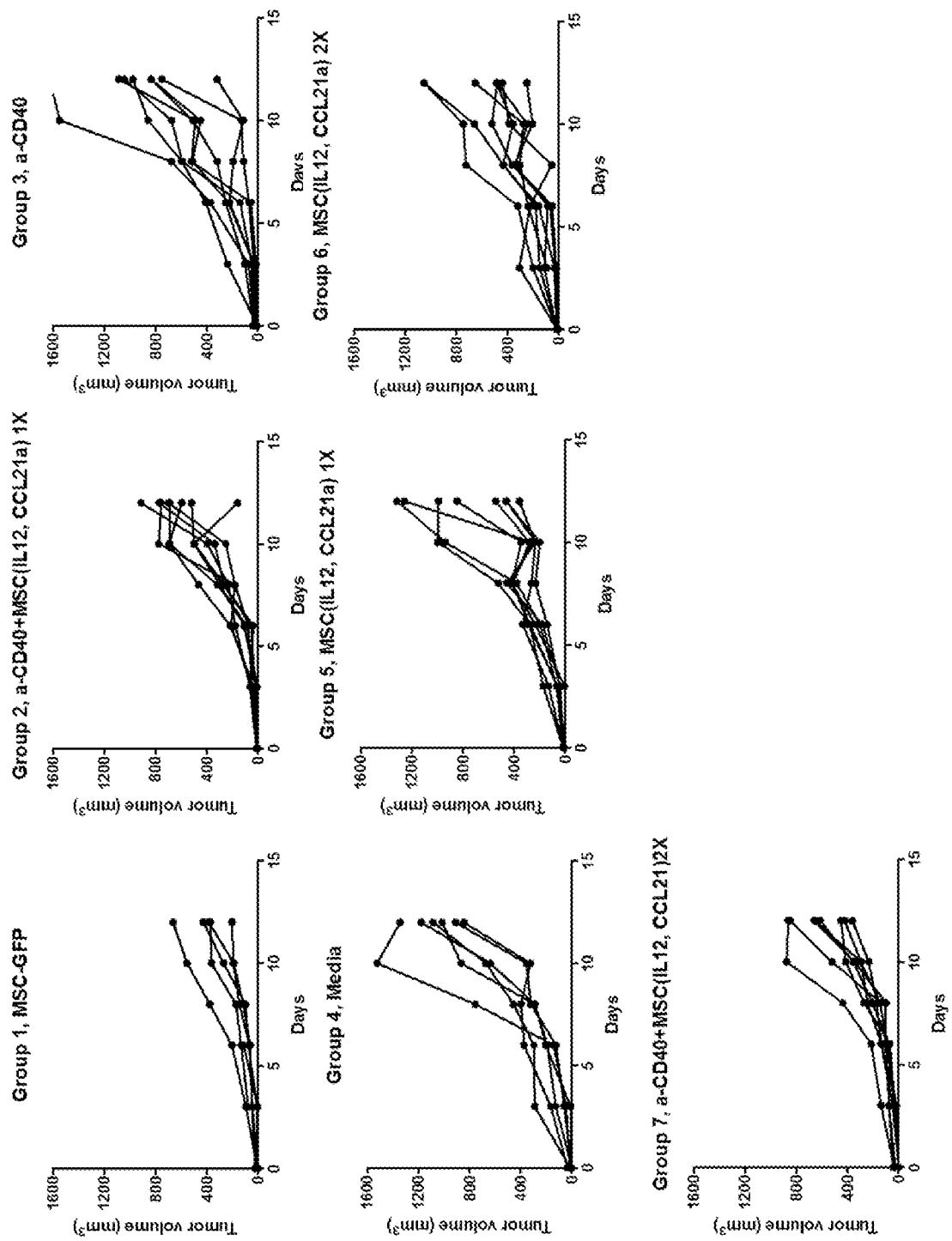
FIG. 7A includes data indicating that engineered MSCs expressing IL-12 and CCL21a inhibit tumor growth in an orthotopic mouse model of breast cancer (4T1 triple negative breast carcinoma); however the addition of anti-CD40 antibody does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 7A represents an individual mouse.
Figure 7B:
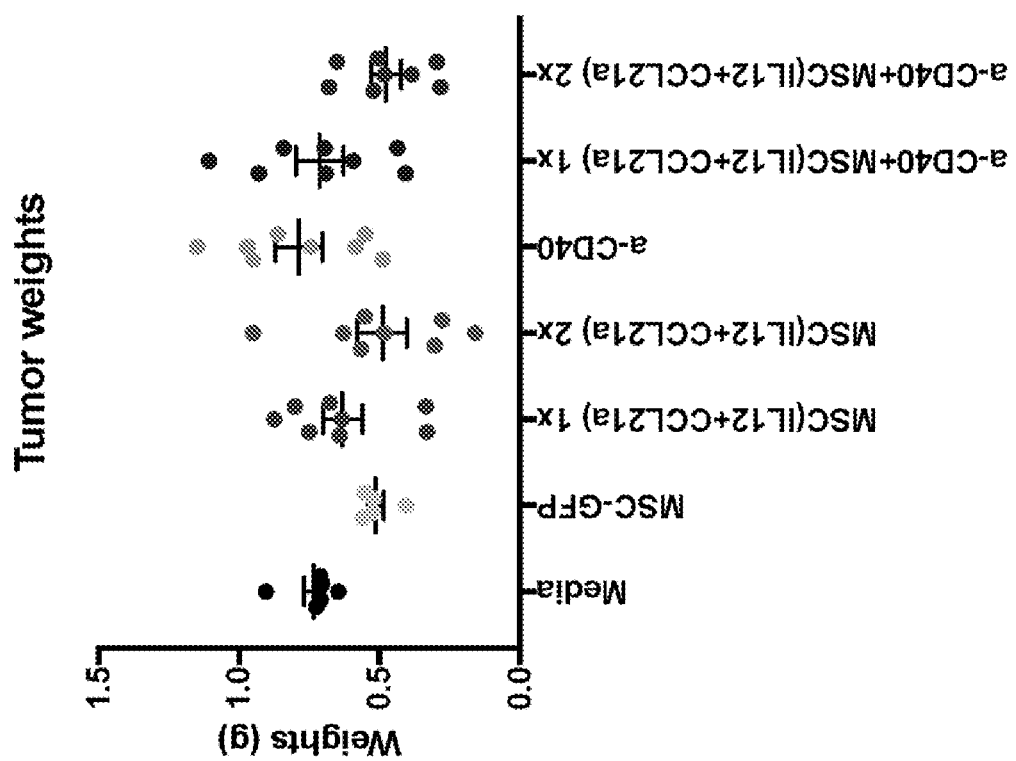
FIG. 7B shows the tumor weight for individual mice in each treatment.

FIGS. 7A-7B show that engineered MSCs expressing IL-12 and CCL21a inhibit tumor growth; however the addition of anti-CD40 antibody does not reduce tumor growth.

Figure 8A:
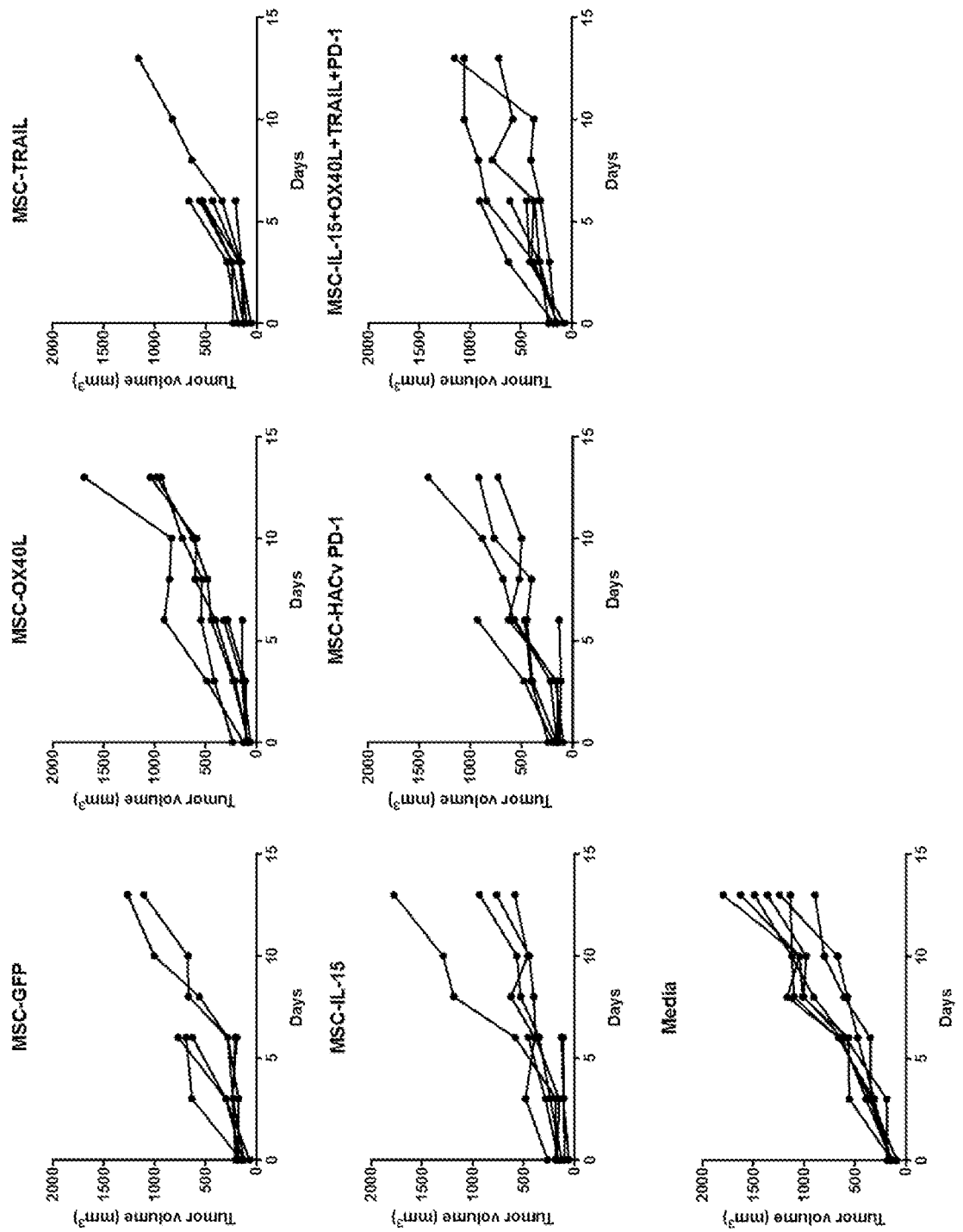
FIG. 8A includes data indicating that engineered MSCs expressing OX40L, TRAIL, IL15, HACvPD-1, or combinations thereof do not inhibit tumor growth significantly in an orthotopic mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 8A represents an individual mouse. The left graph of FIG. 8B shows the tumor weight for individual mice in each treatment. The right graph of FIG. 8B shows body weight represented as mean±SEM for mice receiving each treatment over time.
Figure 8B:
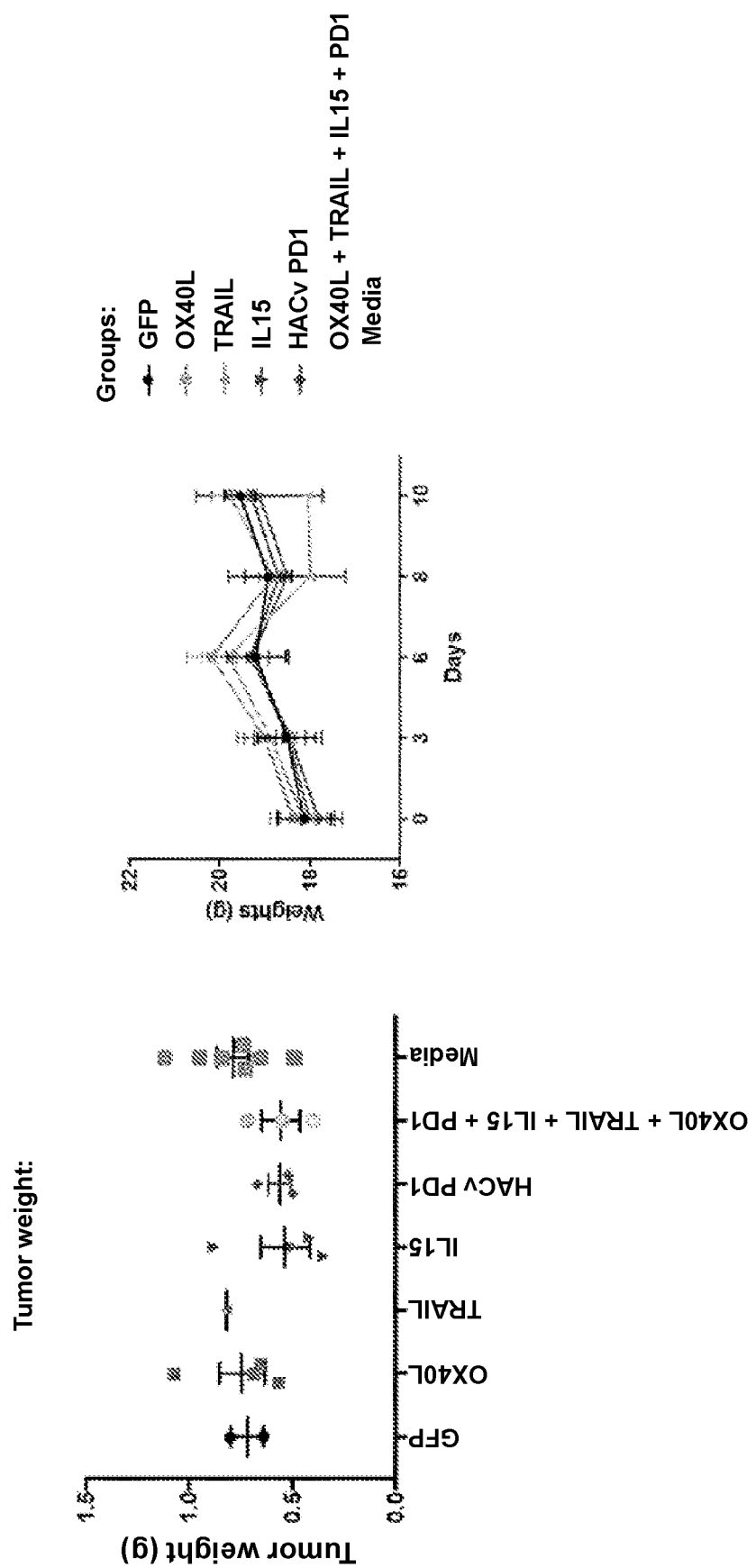

FIGS. 8A-8B show that engineered MSCs expressing OX40L, TRAIL, IL15, HACvPD-1, or combinations thereof do not inhibit tumor growth significantly.

Figure 9A:
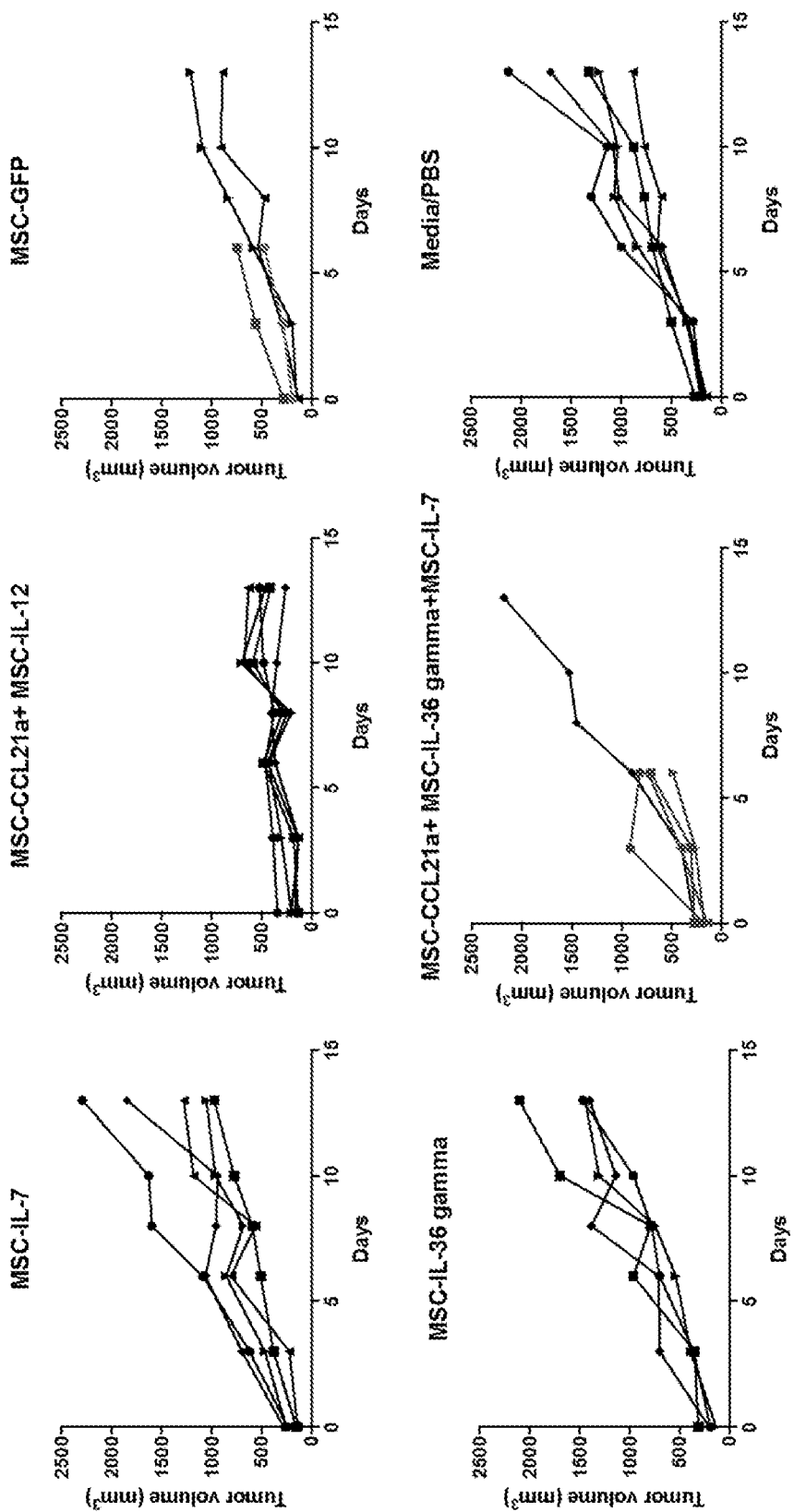
FIG. 9A includes data indicating that engineered MSCs expressing IL-12 and CCL21a inhibit tumor growth in an orthotopic mouse model of breast cancer (4T1 triple negative breast carcinoma); however the combination of MSCs expressing CCL21a, IL-36 gamma and IL-7 does not reduce tumor growth. Some of the effector combinations tested, however, may cause toxicity. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 9A represents an individual mouse.
Figure 9B:
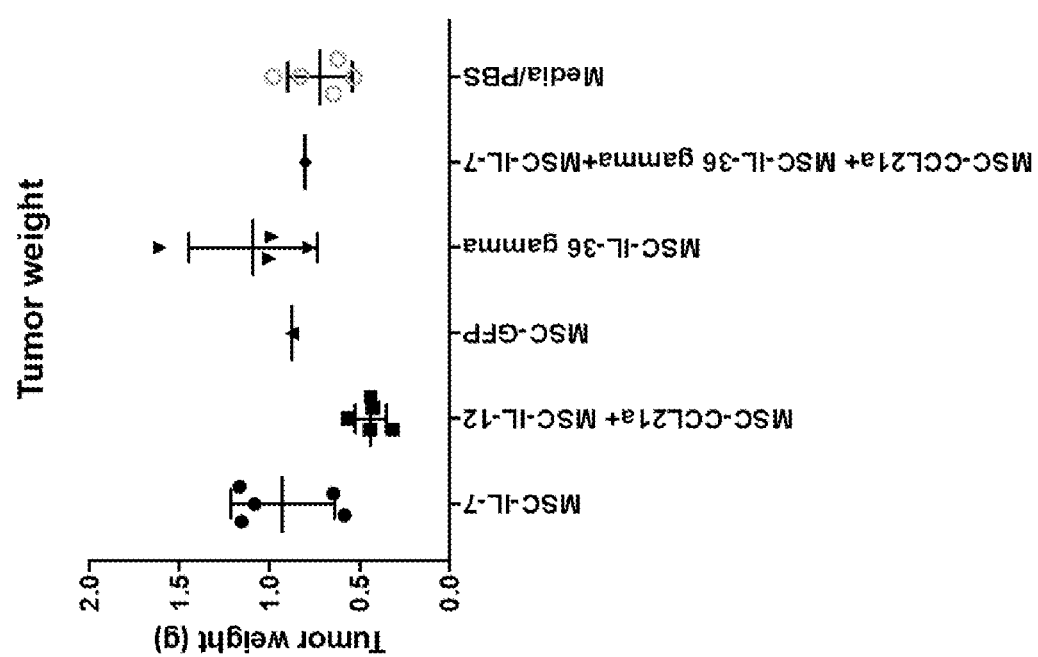
FIG. 9B shows the tumor weight for individual mice in each treatment.

FIGS. 9A-9B show that engineered MSCs expressing IL-12 and CCL21a inhibit tumor growth; however the combination of MSCs expressing CCL21a, IL-36 gamma and IL-7 does not reduce tumor growth. Some of the effector combinations tested, however, may cause toxicity.

Dose Escalation and Toxicity

Figure 10A:
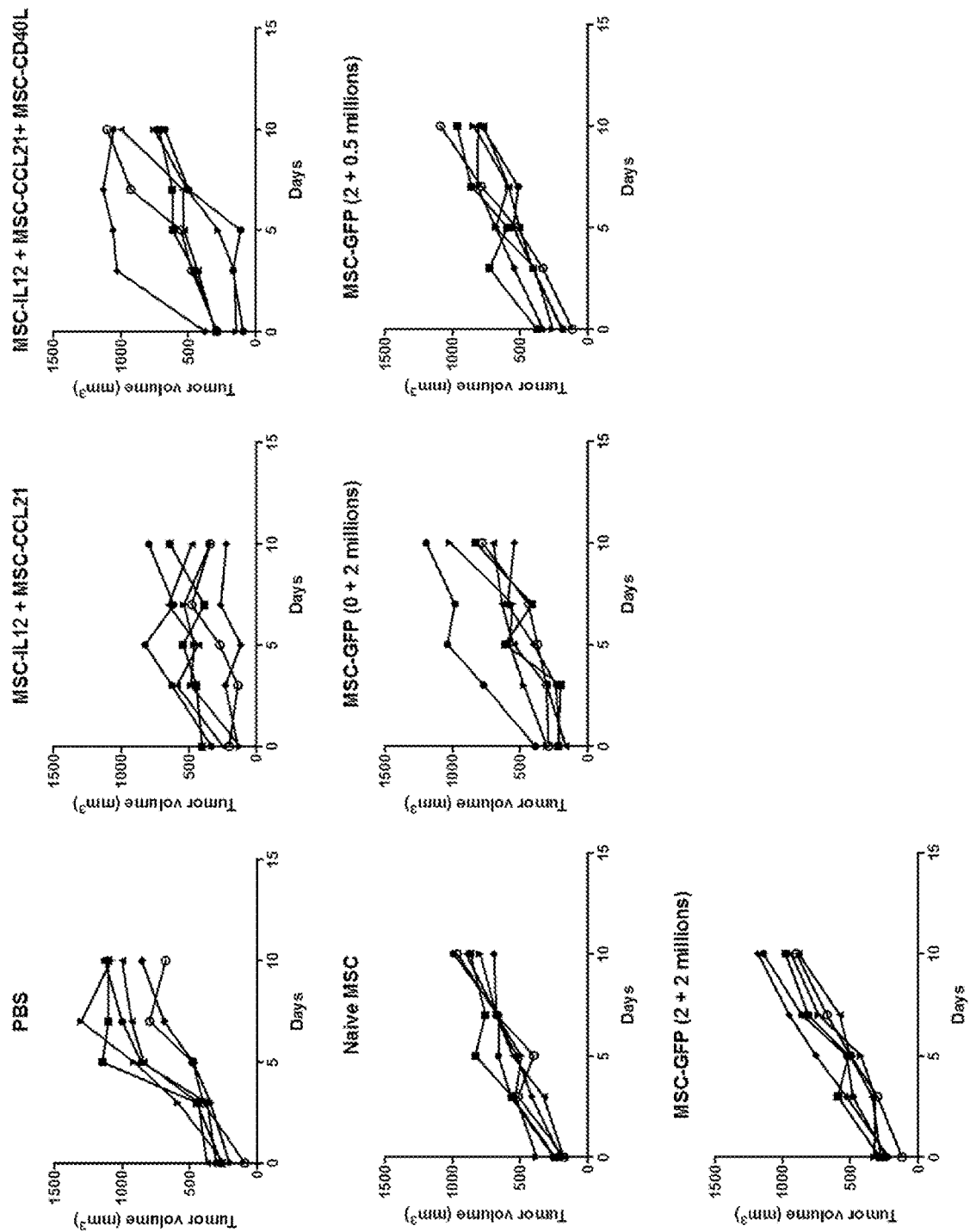
FIGS. 10A-10B include data from a GFP dose escalation study for toxicity and screening.
Figure 10B:
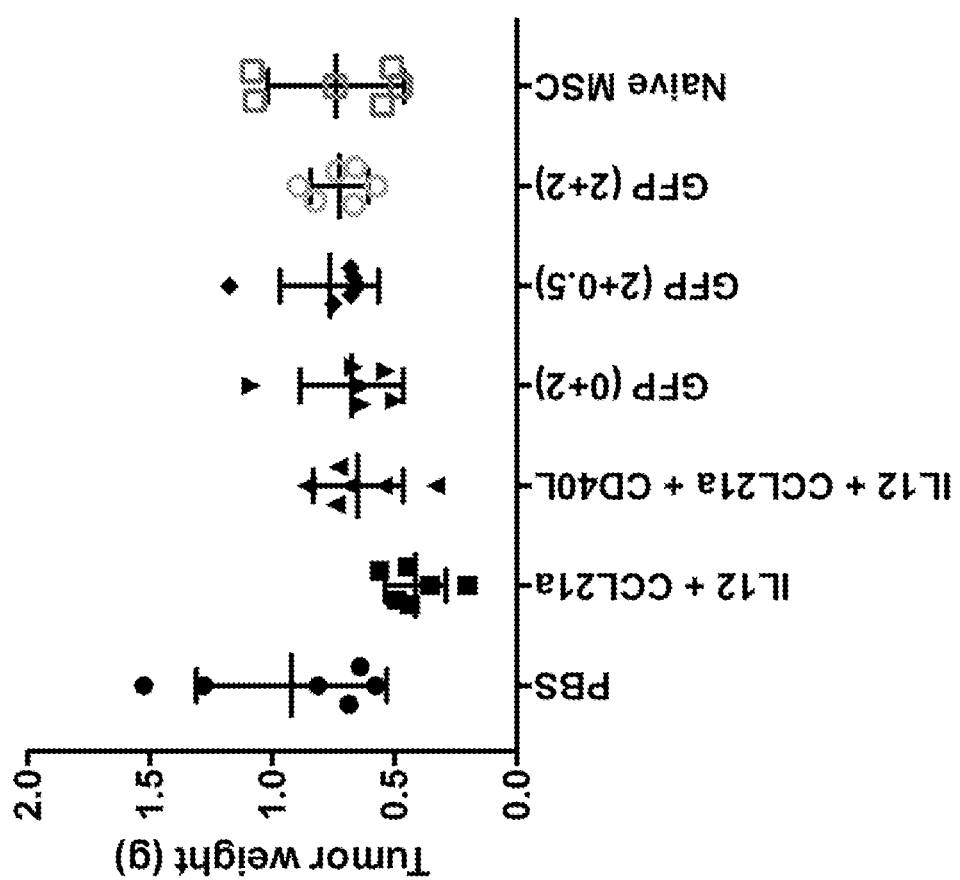

Toxicity was observed in some of the experiments above in the GFP groups, so a dose escalation study was performed to determine the underline cause of toxicity. This experiment determined that engineered MSC cell expression GFP does not elicit toxicity (FIGS. 10A-10B) but rather the MSC suspension media could be the main cause of toxicity.

Effect on Large Tumors

Figure 12:
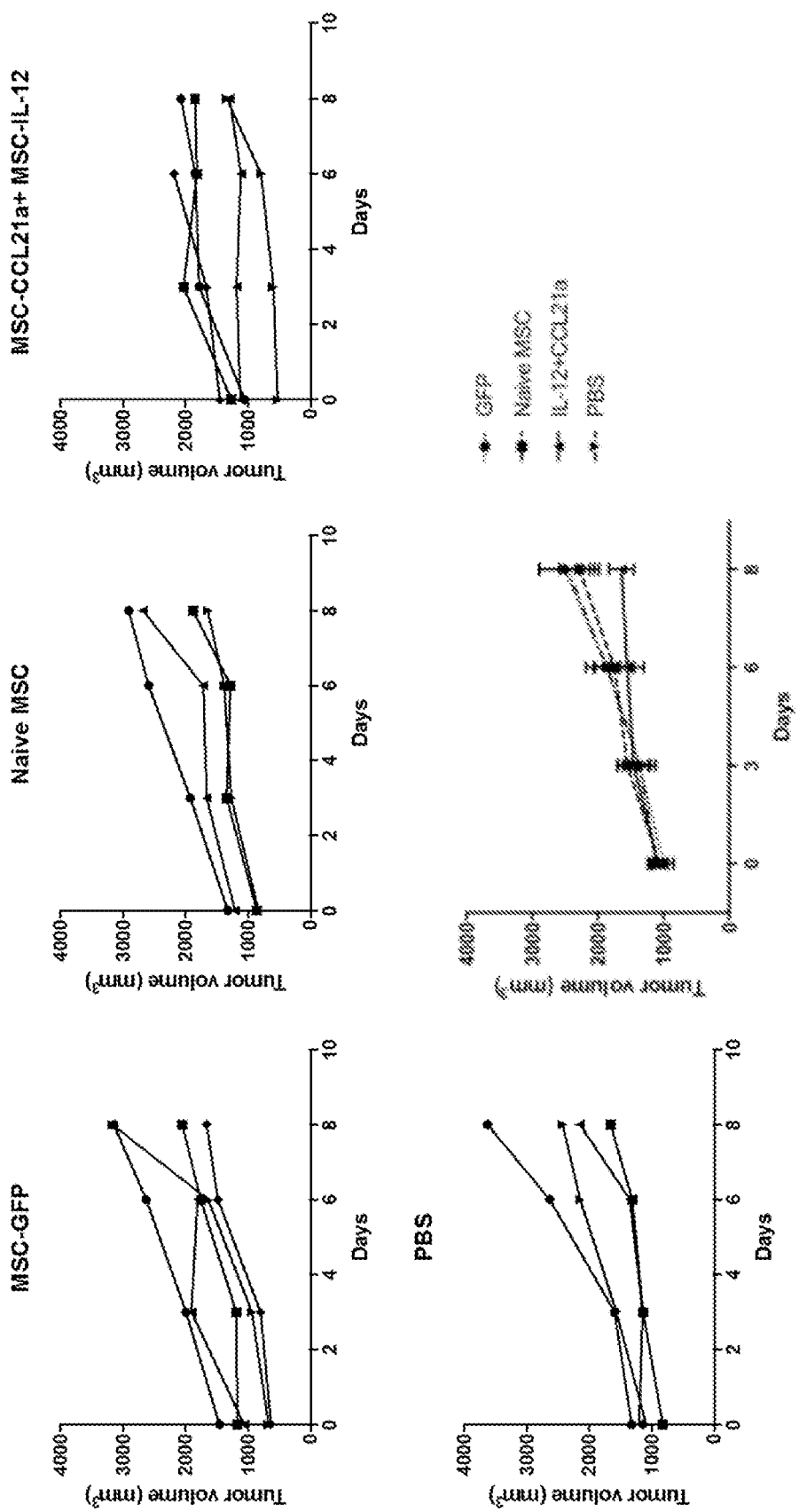
FIG. 12 includes data showing that IL-12 and CCL21a can reduce tumor expansion.

This experiment tested whether engineered mouse MSCs expressing IL12 and CCL21a can reduce tumor burden from larger tumor (>800 mm³). Larger tumor are more difficult to treat than small tumor, and this experiment demonstrates this effector combination can reduce tumor expansion (FIGS. 12A-12B).

Checkpoint Inhibitors

Figure 13A:
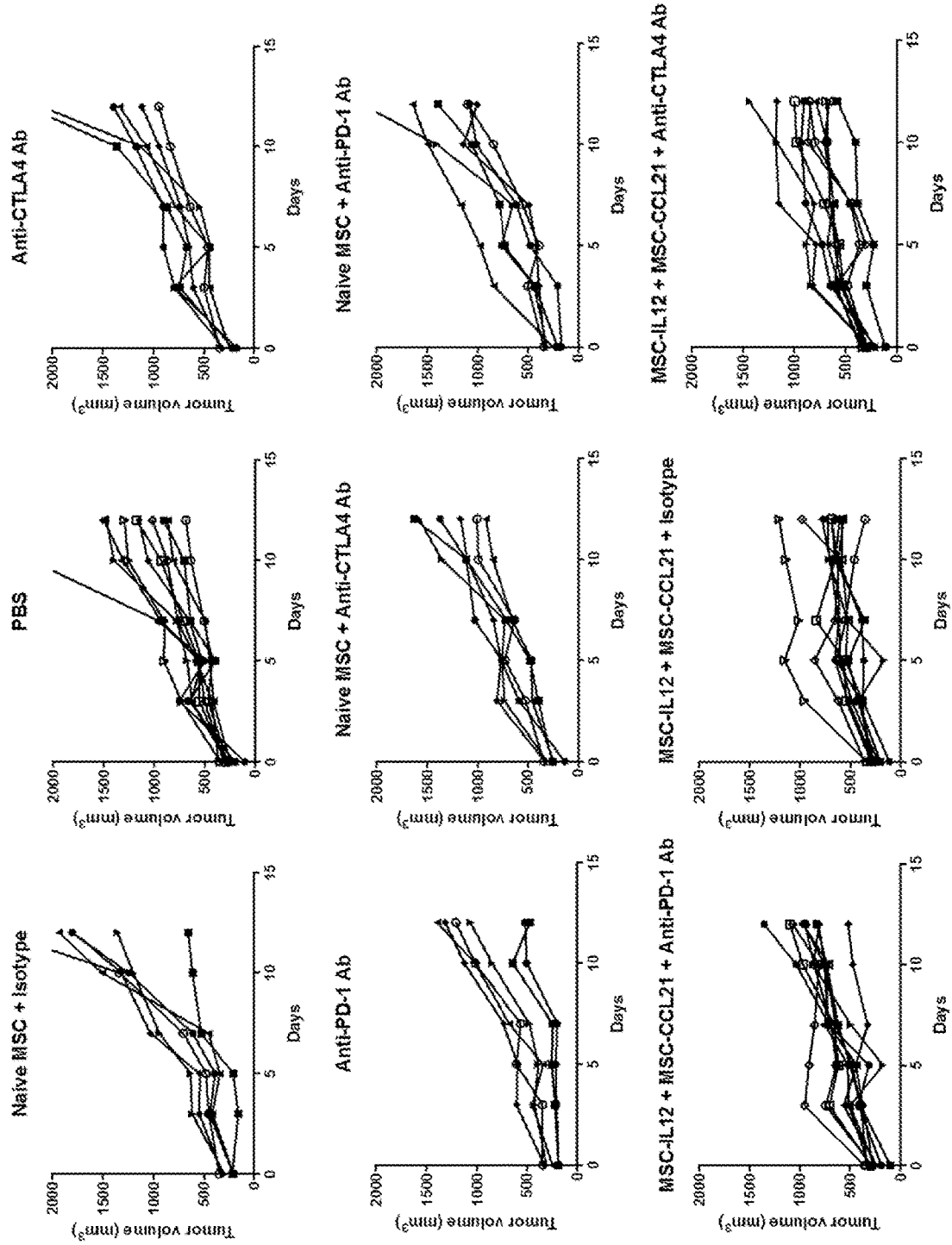
FIG. 13A includes data indicating that engineered MSCs expressing IL-12 and CCL21 are sufficient to inhibit tumor growth in an orthotopic mouse model of breast cancer (4T1 triple negative breast carcinoma), and the addition of a checkpoint inhibitor (anti-PD-1 antibody or anti-CTLA-4 antibody) did not increase efficacy. Each effector was expressed by a different MSC, and the MSCs were combined (at a 1:1 ratio) for combinatorial treatment, and the checkpoint inhibitor was injected separately. Each chart shows the effect of engineered MSCs expressing the indicated immunotherapies alone or in combination on the growth of 4T1 breast tumors in mice (n=6-8). Each line of FIG. 13A represents an individual mouse.
Figure 13B:
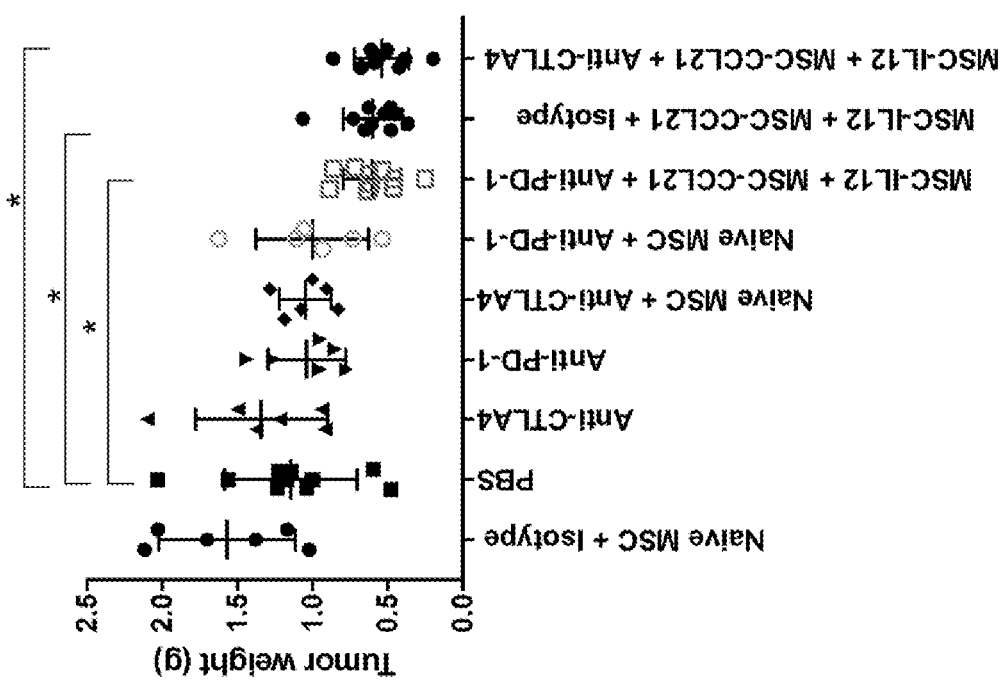
FIG. 13B shows the tumor weight for individual mice in each treatment.

FIG. 13A shows that engineered MSCs expressing IL-12 and CCL21 are sufficient to inhibit tumor growth, and the addition of a checkpoint inhibitor (anti-PD-1 antibody or anti-CTLA-4 antibody) by injection did not increase efficacy.

Example 6. CT26 Colorectal Carcinoma

In the following experiments, MSCs were engineered to express one of the following effector molecules, then administered, alone or in combinations, to a colorectal carcinoma mouse model: IFNβ, IL12, IL15, IL36γ, IL7, CCL21a, HACv-PD1, or 41BB. In some examples, a checkpoint inhibitor (anti-CD40 or anti-CTLA-4 antibody) was injected in combination with administration with the engineered MSCs.

Figure 14:
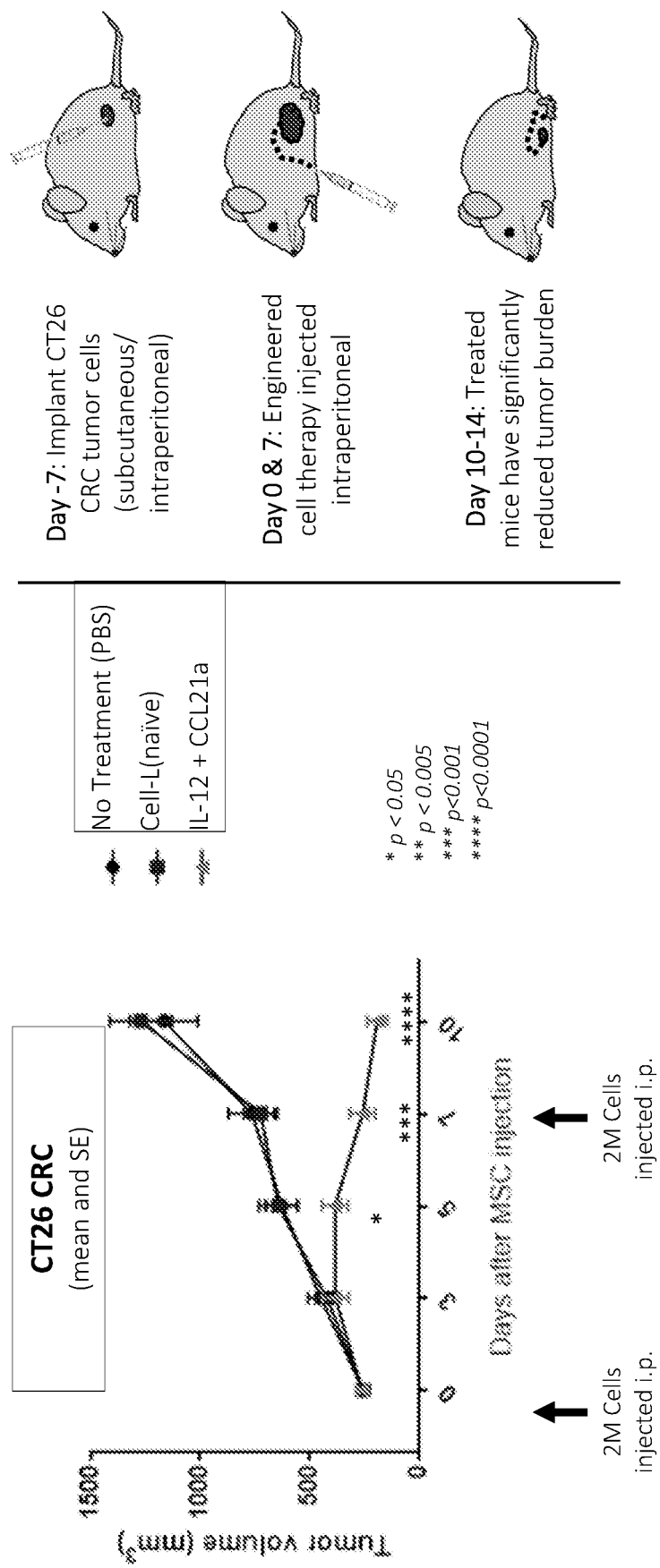
FIG. 14 shows data indicating that engineered MSCs expressing IL-12 and CCL21a induced significant tumor growth delay in a mouse model of colorectal cancer. The graph on the left shows the effects of engineered MSCs on CT26 colorectal tumor growth in mice (n=8). Each line in the chart represents tumor volume in mice receiving intraperitoneal injection of either control MSC growth media or engineered MSCs on day 0 and day 7. Mice received intraperitoneal injection of engineered MSCs expressing IL-12 and engineered MSCs expressing CCL21a. Tumor volume was determined by caliper measurements every other day. Data represent mean±SEM. *$p<0.05$, **$p<0.005$ as compared to control media group. The schematic on the right shows a timeline of treatment and the effect of engineered MSCs expressed combinatorial genes IL-12 and CCL21a on tumor burden in treated mice.

FIG. 14 shows that engineered MSCs expressing IL-12 and CCL21a induced significant tumor growth delay.

Figure 15:
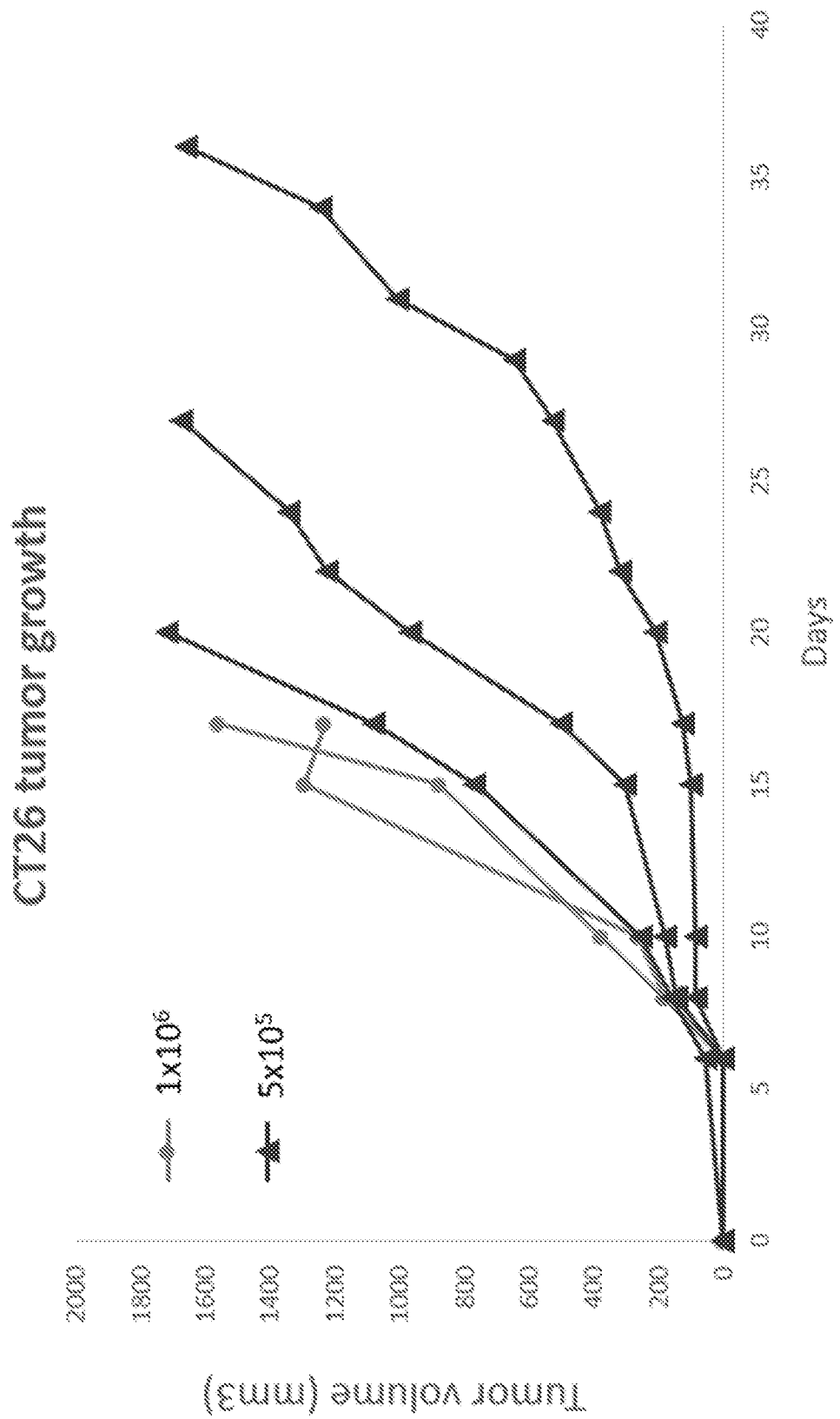
FIG. 15 is a graph showing tumor growth kinetics in the CT26 mouse model to determine optimal time for dosing the engineered MSC cells.

FIG. 15 shows tumor growth kinetics in the CT26 mouse model to determine optimal time for dosing the engineered MSC cells.

In Vivo Efficacy

Figure 16A:
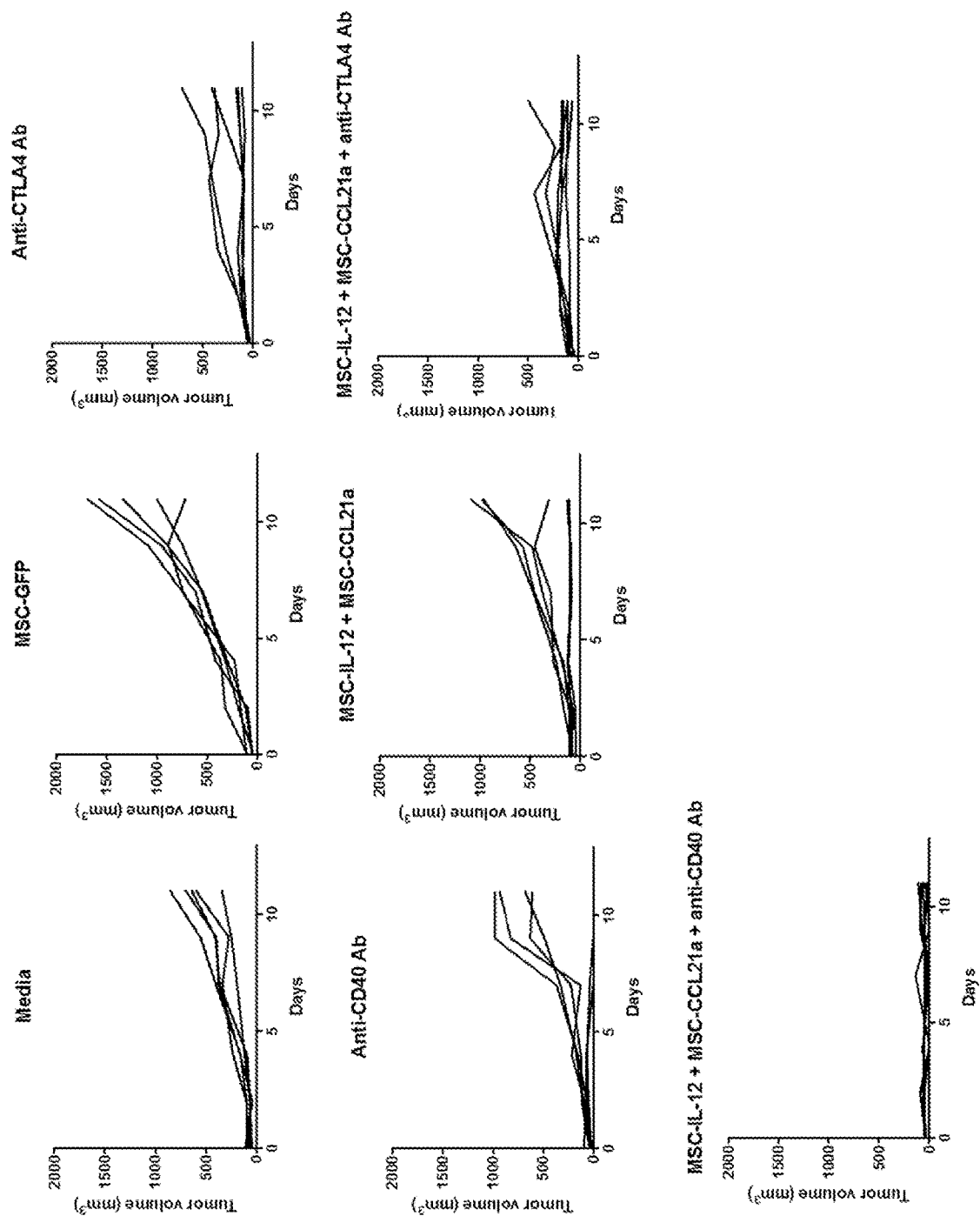
FIGS. 16A-16B include data indicating the effects of engineered MSCs expressing IL-12 and CCL21a combined with anti-CD40 or anti-CTLA4 antibodies on average tumor growth in a syngeneic mouse model of colon cancer. Mice bearing CT26 colon tumors were treated with one of seven treatments (n=5-6 per treatment group). MSC-IL-12+MSC-CCL21a indicates treatment with engineered cells expressing IL-12 and with engineered cells expressing CCL21a (at a 1:1 ratio) for combinatorial treatment. The left graph of FIG. 16B shows the tumor weight for individual mice in each treatment. The right graph of FIG. 16B shows the tumor volume represented as mean±SEM for mice receiving each treatment over time.
Figure 16B:
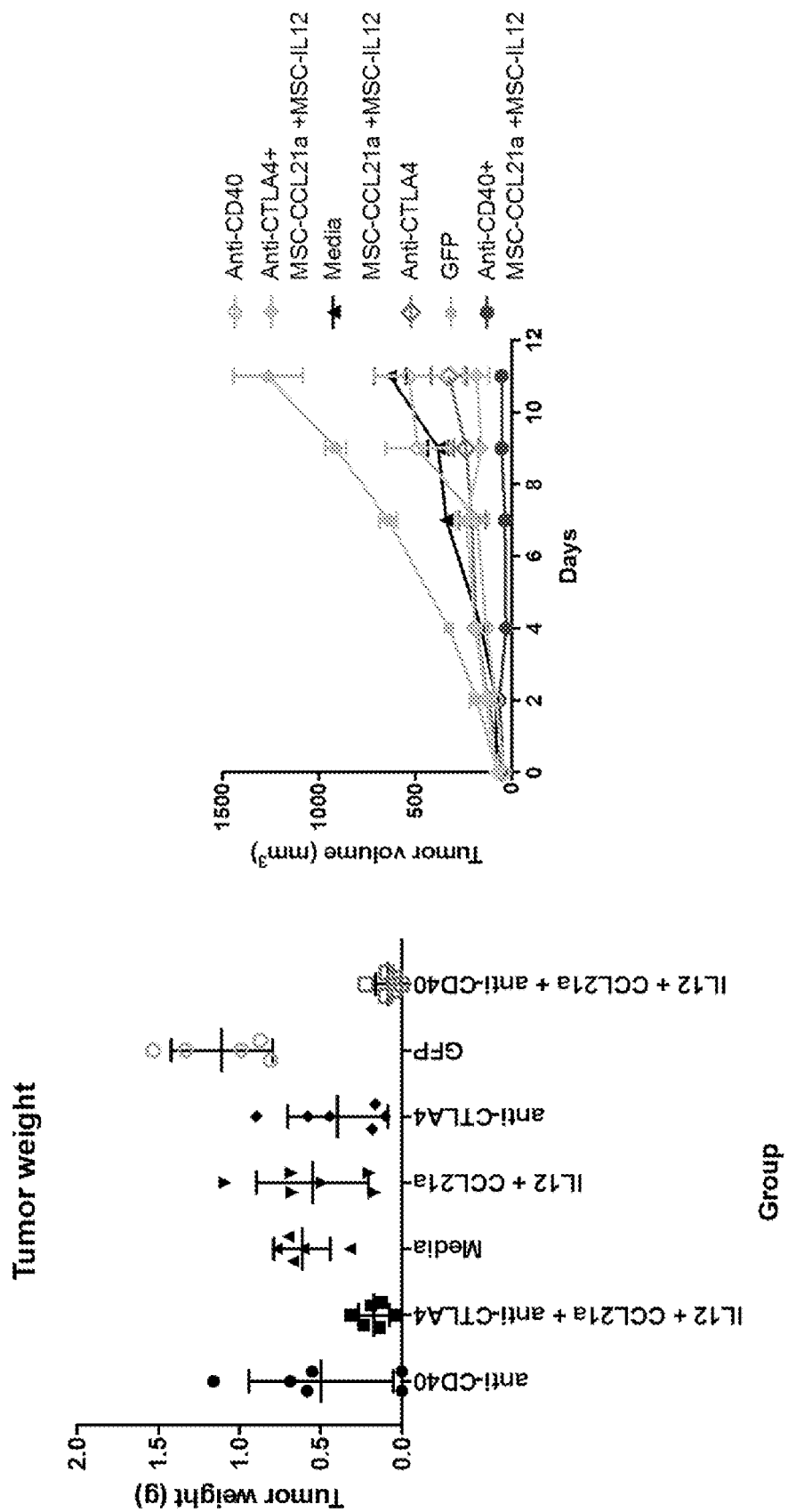

The following experiments demonstrate the in vivo efficacy of MSCs expressing immunotherapy effectors (payloads) in the subcutaneous mouse model of colon (colorectal) cancer. CT26-Neo-Fluc mouse colon cancer cells (Imanis Life Sciences, $5 \times 10^5$) were injected subcutaneously into the flanks of female BALB/cJ mice (The Jackson Laboratory). Seven days after tumor implantation, mice were then randomized into the following treatment groups: control MSC growth media, engineered MSCs (MSC-12+CCL21a), anti-CD40 antibody, anti-CTLA4 antibody (Bio X cell), MSC-12+CCL21a in combination with anti-CD40 antibody or MSC-12+CCL21a in combination with anti-CTLA4 antibody. Engineered MSCs ($2 \times 10^6$ cells) were injected intraperitoneally (ip) once a week for two weeks (Day 0 and 7). Anti-CD40 antibodies were injected ip (100 µg) on Days 0 and 3. Anti-CTLA4 antibodies were injected ip (100 µg) on Days 0, 3 and 7. Tumor growth was monitored by caliper measurements every other day, and mouse weights were recorded twice weekly. Mice were euthanized 11 days after first MSC treatment and tumors were collected and weighed. The tumor weight of individual mice in each treatment group was measured and the results are shown in the bottom left of FIG. 16B (left graph). The average tumor volume of each treatment group was monitored over time (FIG. 16B, right graph). Treatment Groups 2 (IL-12+CCL21a+anti-CTLA4 antibody), 4 (IL-12+CCL21a) and 7 (IL-12+CCL21a+anti-CD40 antibody) inhibited the average growth of CT26 colon tumors compared to GFP-treated mice (FIG. 16B, right graph). Similar results were observed when the tumor volume of individual mice in each treatment group was measured over time (FIG. 16A). Therefore, combinatorial treatment with MSCs expressing immunotherapies inhibited the growth of colon cancer cells in vivo.

Figure 18A:
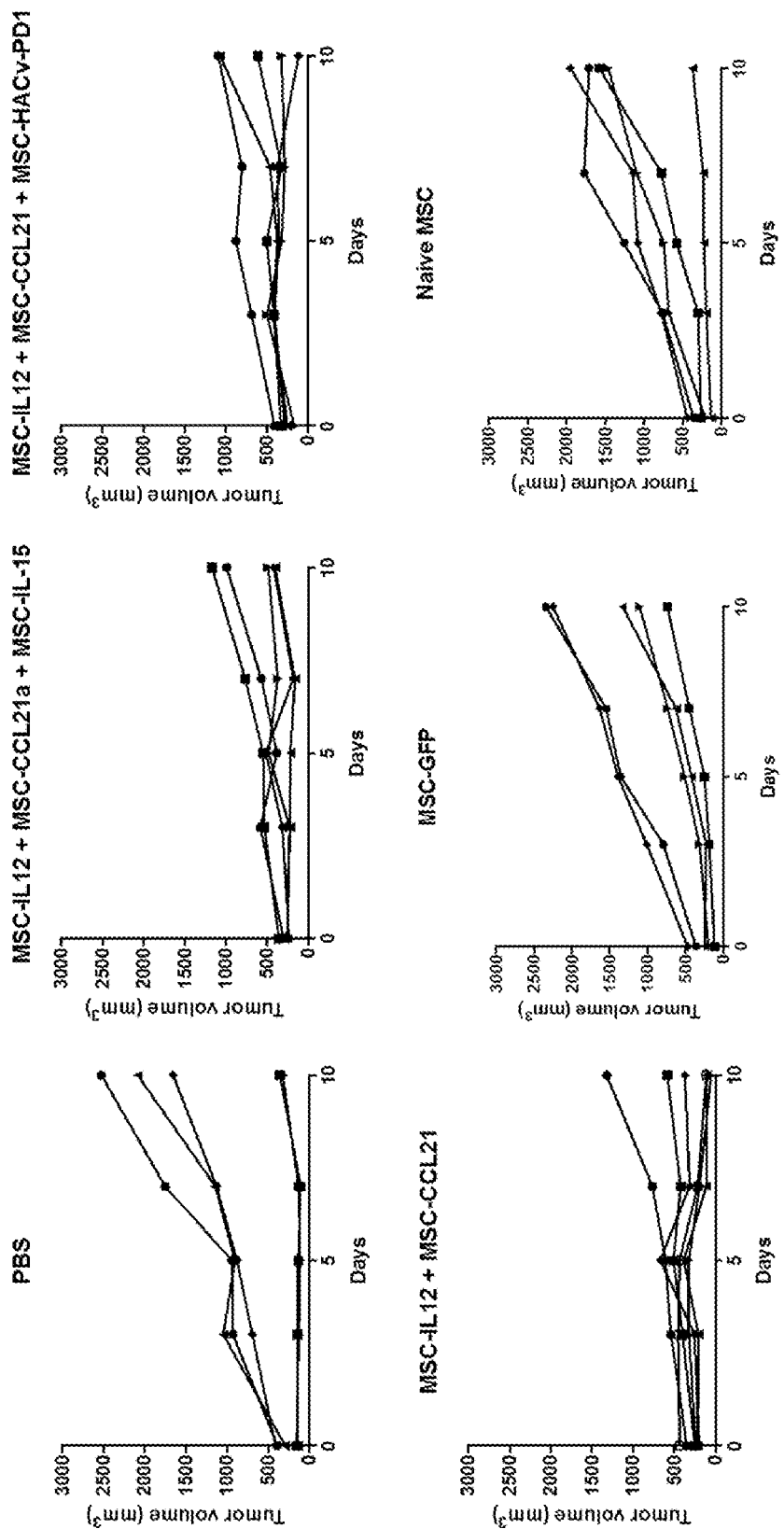
FIG. 18A includes data indicating that engineered MSCs expressing IL-12, CCL21a, and either IL15 or HACvPD-1 inhibit tumor growth significantly in a moue model colorectal cancer. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 colorectal tumors in mice (n=6-8). Each line of FIG. 18A represents an individual mouse.
Figure 18B:
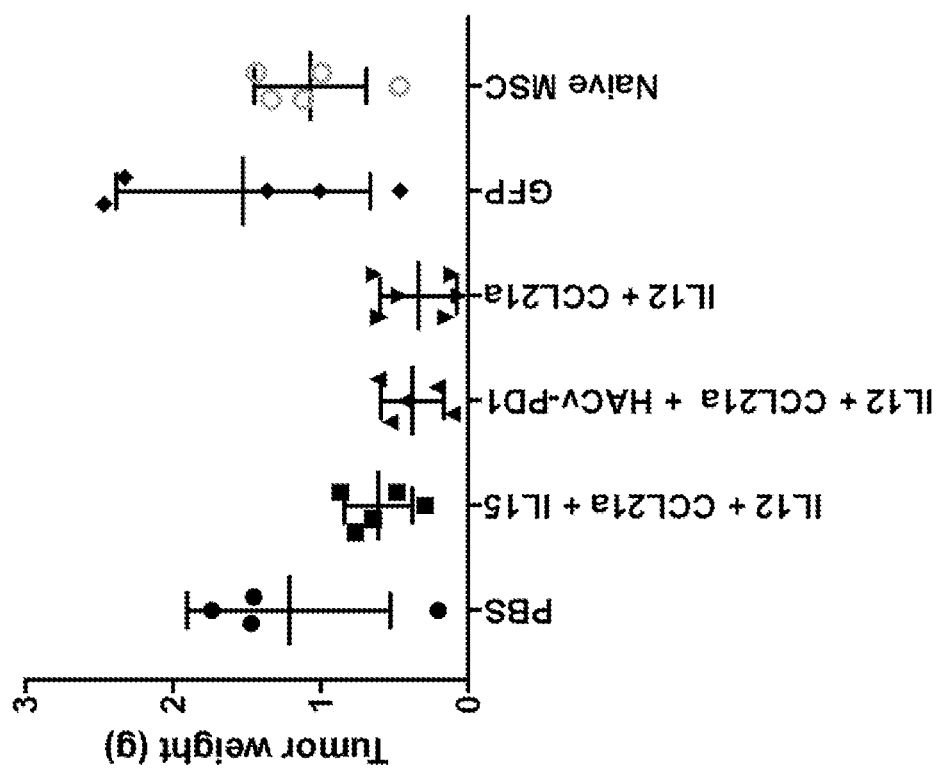
FIG. 18B shows the tumor weight for individual mice in each treatment.
Figure 18C:
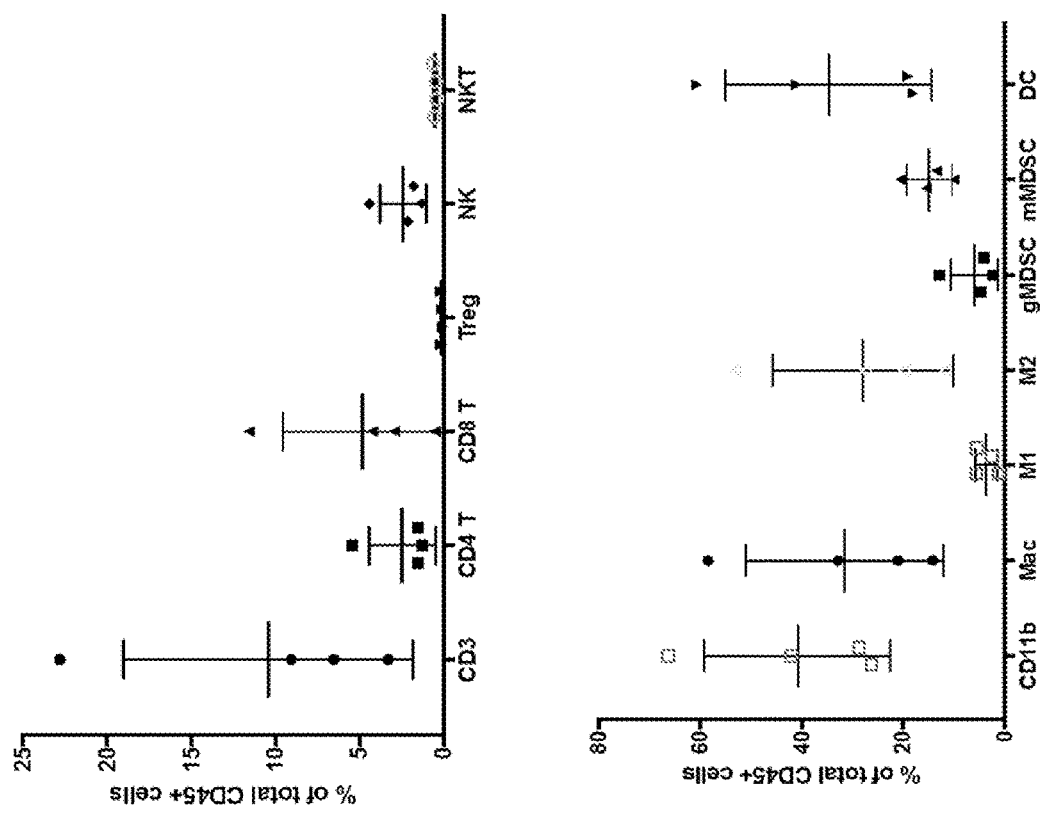
FIG. 18C is a representative graph of the infiltrating immune population within the tumor microenvironment.
Figure 18D:
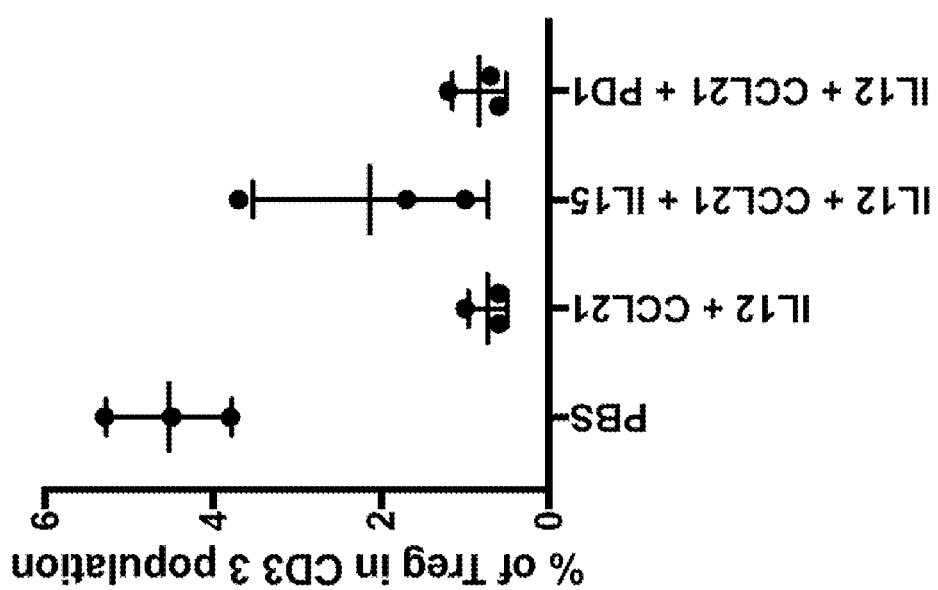
Figure 18E:
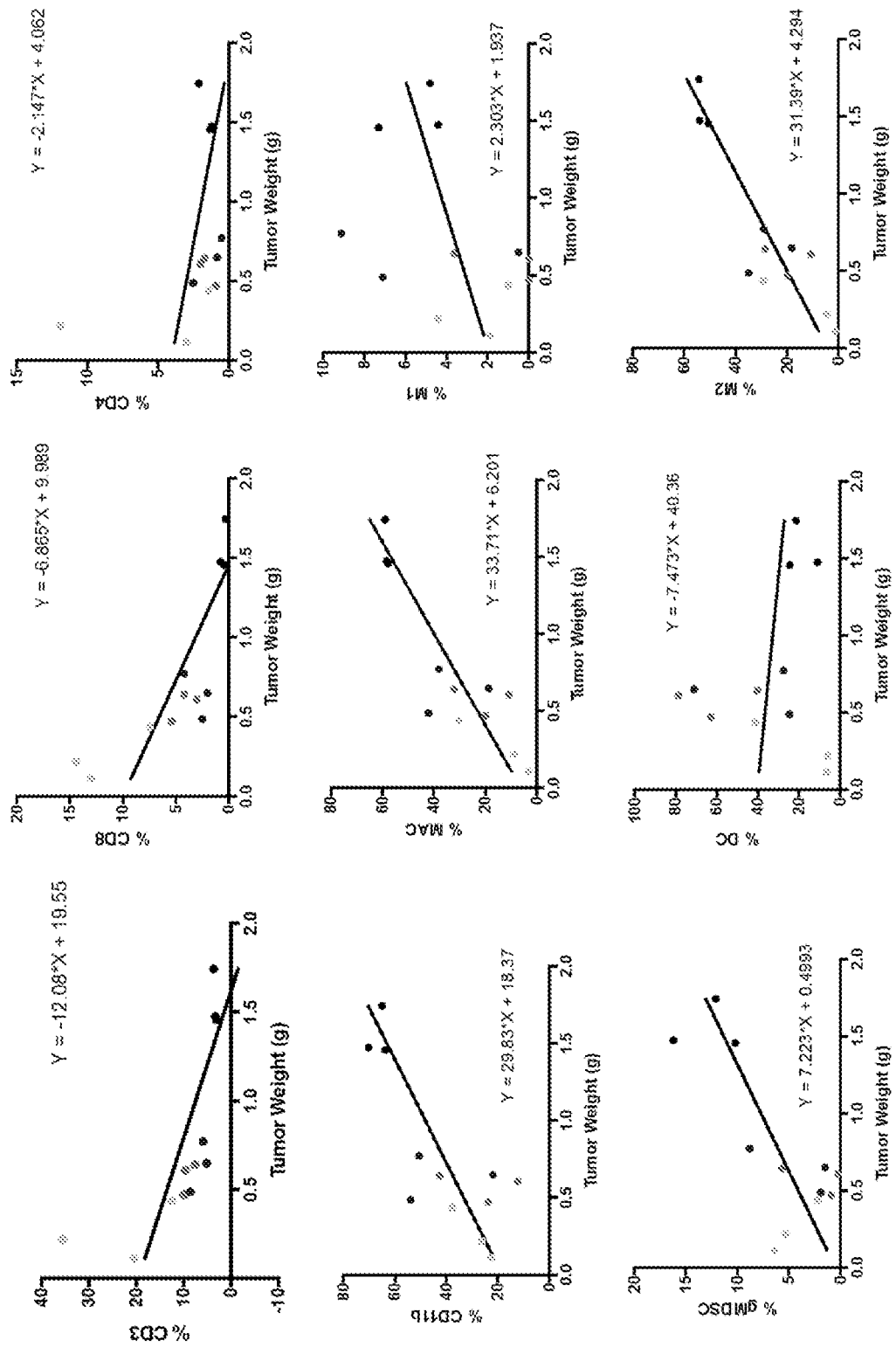
FIG. 18E correlates the percentage of immune infiltration with tumor weight. Samples with high lymphocytes (CD3+) were found to correlate with low tumor weight, while samples with high myeloid (CD11b+) infiltration were correlated with higher tumor burden.

FIG. 18A shows that engineered MSCs expressing IL-12, CCL21a, and either IL15 or HACvPD-1 inhibit tumor growth significantly in a moue model colorectal cancer. FIG. 18B shows the tumor weight for individual mice in each treatment. FIG. 18C is a representative graph of the infiltrating immune population within the tumor microenvironment. FIG. 18D shows the percentage of regulatory T cells (Treg) in the total CD3 population. There was a significant decrease in the numbers of Tregs in the tumor microenvironment treated with engineered MSC-IL2 and CCL21a. FIG. 18E correlates the percentage of immune infiltration with tumor weight. Samples with increase in lymphocytes (CD3+) were found to correlate with low tumor weight, while samples with high myeloid (CD11b+) infiltration were correlated with higher tumor burden.

Long-Term Survival

Figure 17A:
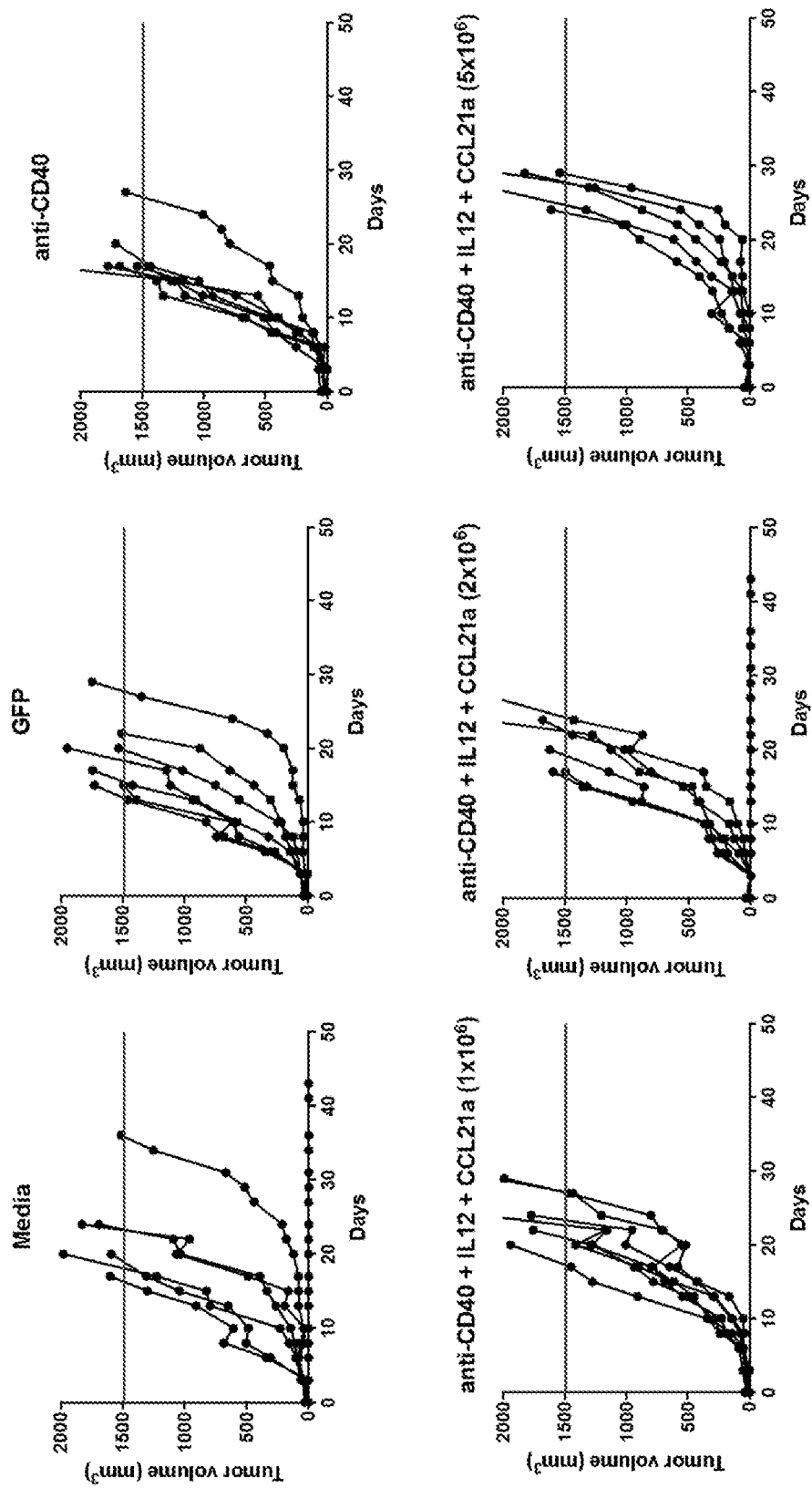
FIGS. 17A-17B include data from a dose-dependent long-term survival study.
Figure 17B:
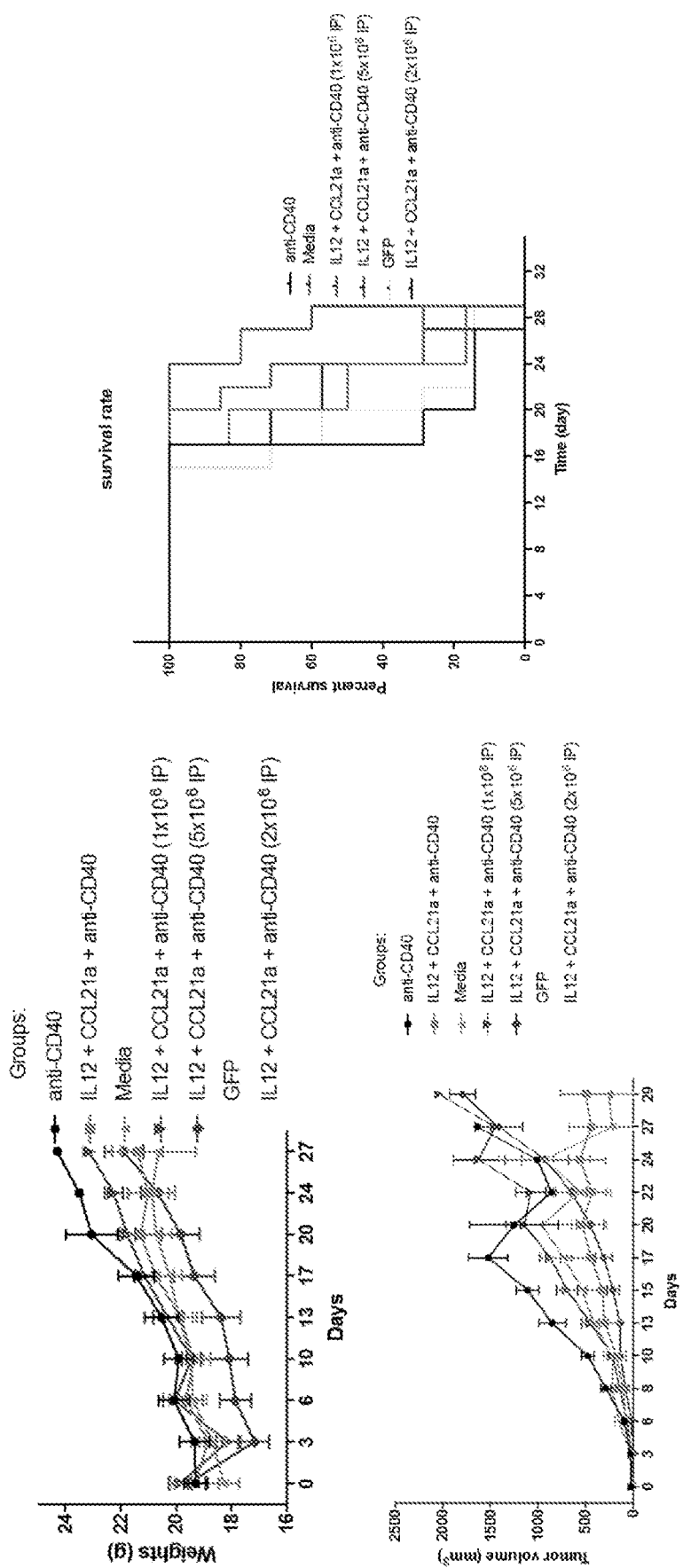

Mice were dosed twice with different concentration of engineered MSC-IL12 and CCL21a therapy in combination with injected anti-CD40 antibody. After the second dose, tumor volume was monitored twice a week until tumor burden is greater than 1500 mm³ and the mice were sacrificed. FIG. 17A shows the tumor volume of the individual group. FIG. 17B, left graph, tracks the mice weight and tumor volume from individual group over time. FIG. 17B, right graph, shows the survival plot of the different groups.

MSC Homing

Figure 19:
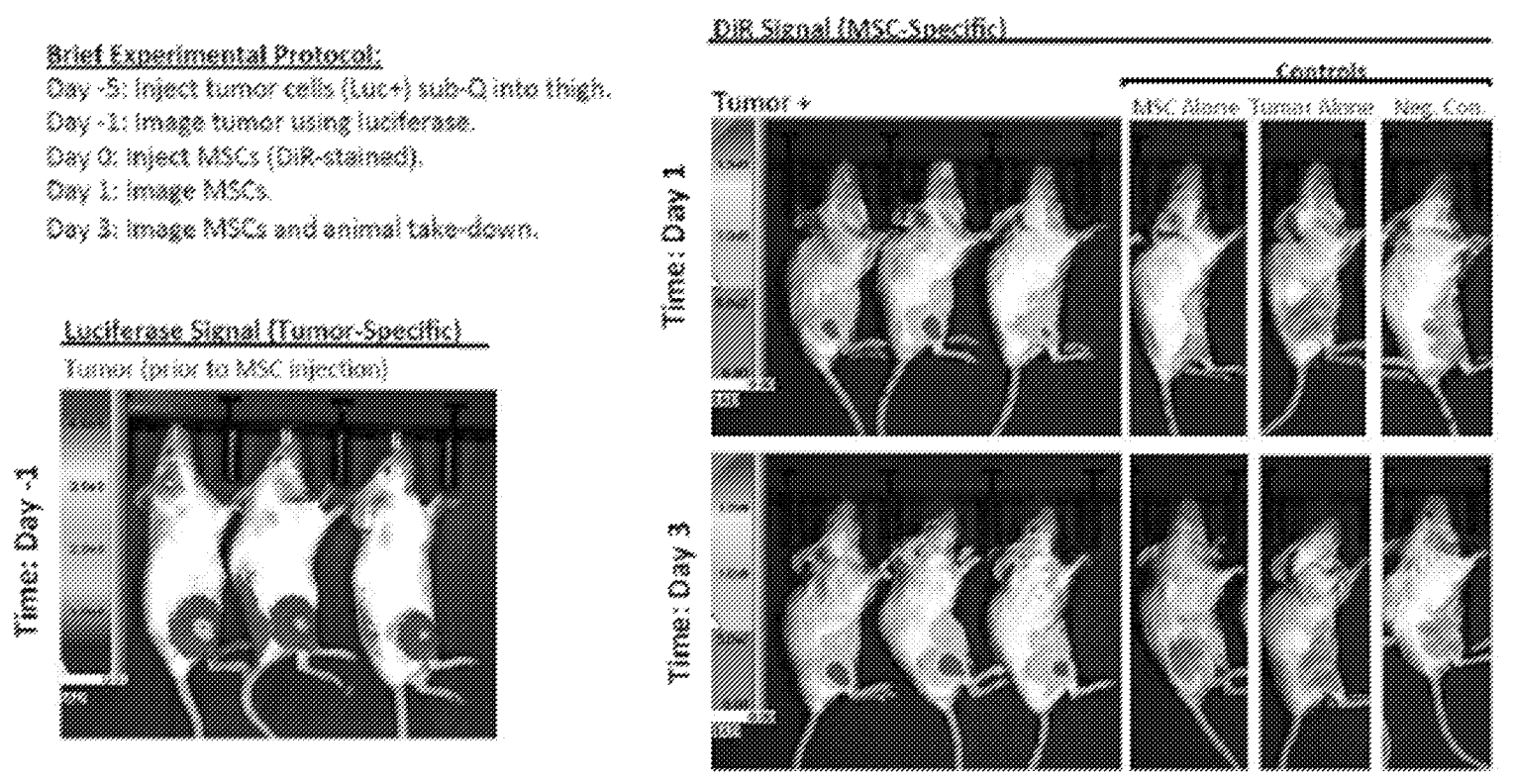

This following experiments demonstrate that murine MSCs home to tumors in a mouse model of colon cancer. A brief experimental protocol is provided in the top left section of FIG. 19. Luciferase-expressing CT26 colon cancer tumor cells ($5 \times 10^5$) were subcutaneously implanted into the right thigh of female BALB/cJ mice. After 4 days, tumor localization and size was determined through the CT26 cell's luciferase reporter using the Ami HT live animal imager (Spectral Instruments) (FIG. 19, bottom left panel, Luciferase Signal (Tumor-Specific)). At 5 days post-tumor implantation, 2 million murine BM-MSCs fluorescently labeled with XenoLight DiR (Caliper Life Sciences) were transplanted into the tumor-bearing mice (Tumor+) via intraperitoneal injection. At days 1 and 3 post-MSC injection, localization of XenoLight DiR fluorescently labelled MSCs was determined using the Ami HT imager (FIG. 19, right panel, DiR Signal (MSC-Specific)). Injected MSCs co-localized to the site of CT26 colon tumors (FIG. 19, compare localization of tumor-specific luciferase signal in mice prior to MSC injection in bottom left panel and MSC-Specific DiR signal in Tumor+mice on Day 1 and Day 3 after injection on the right). Therefore, MSCs do specifically home in vivo to sites of CT26 colon tumors, and these results show that the MSCs can be used as delivery vehicles for anti-cancer molecules, proteins or compounds.

Figure 20A:
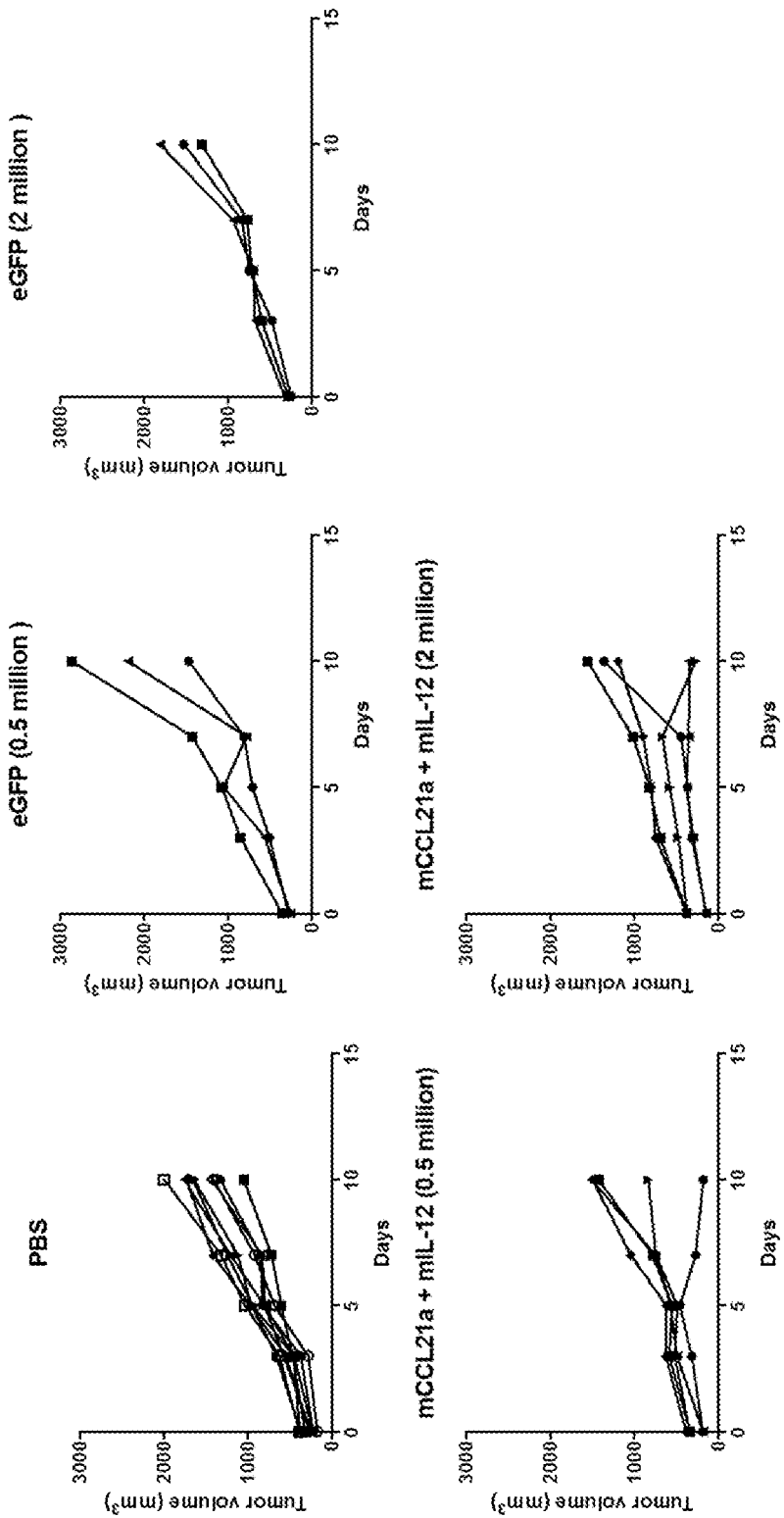
FIG. 20A shows that engineered human MSCs do not home to mouse CT26 tumors.
Figure 20B:
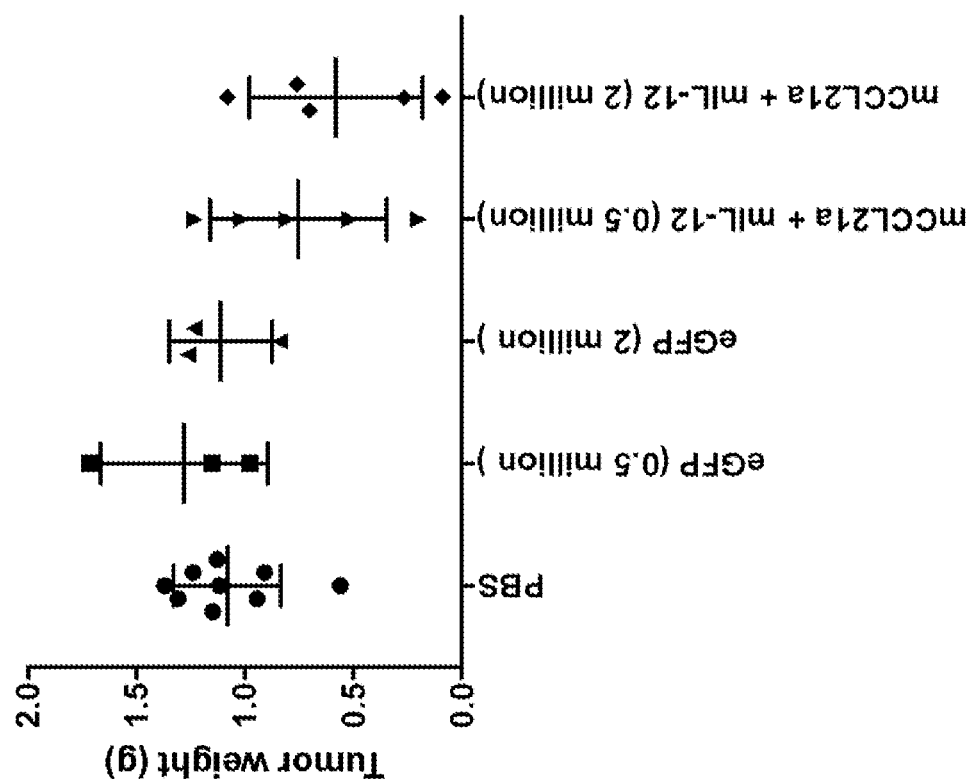
FIG. 20B shows the tumor weight for individual mice in each treatment. Efficacy was determined by tumor volume from caliper measurement every other day.

FIG. 20A shows that engineered human MSCs do not home to mouse CT26 tumors. FIG. 20B shows the tumor weight for individual mice in each treatment. Efficacy was determined by tumor volume from caliper measurement every other day.

Tumor Growth Kinetics

Figure 21A:
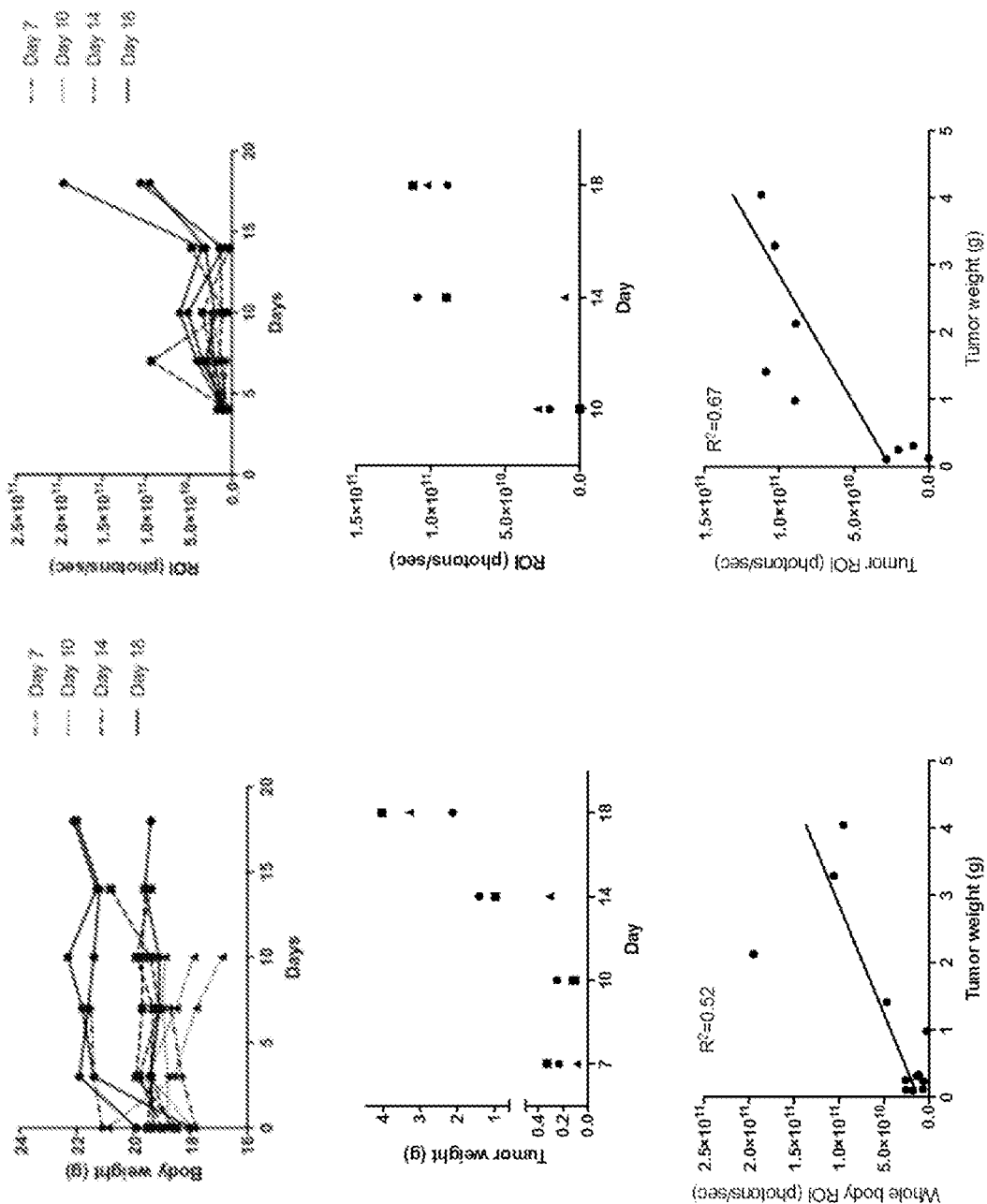
FIGS. 21A-21B show the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth. The first row of FIG. 21A measures the mice body weight and ROI with an IVIS imager to monitor tumor burden. The second row monitors the tumor weight and the ROI of the tumor of individual mice in each group. The third row correlates the tumor weight with either whole body ROI or tumor ROI.
Figure 21B:
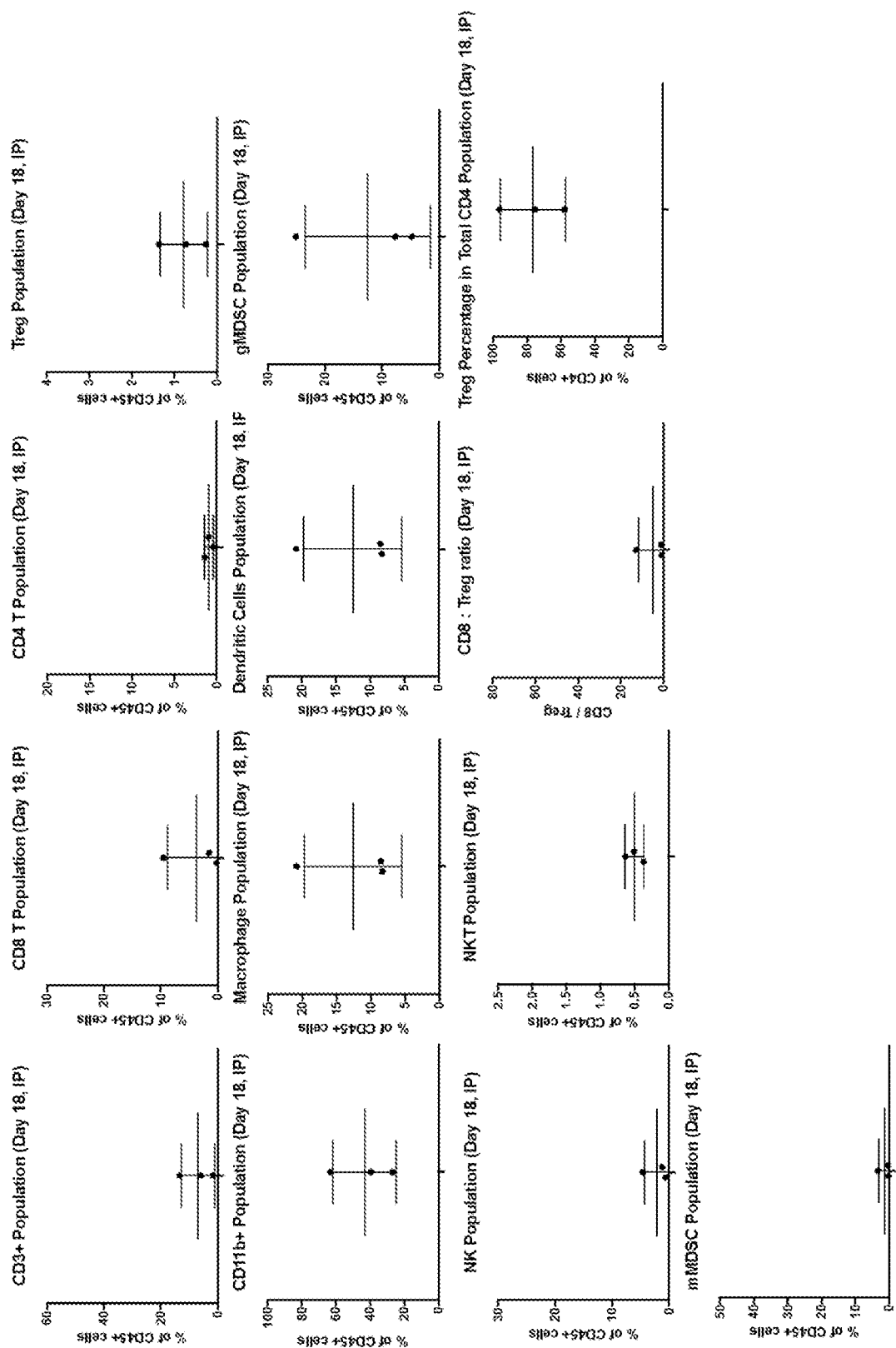

FIGS. 21A-21B show the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth. The first row of FIG. 21A measures the mice body weight and ROI with an IVIS imager to monitor tumor burden. The second row monitors the tumor weight and the ROI of the tumor of individual mice in each group. The third row correlates the tumor weight with either whole body ROI or tumor ROI. FIG. 21B shows the immune profile of three (3) mice in the day 18 group to better understand the tumor microenvironment.

Figure 22A:
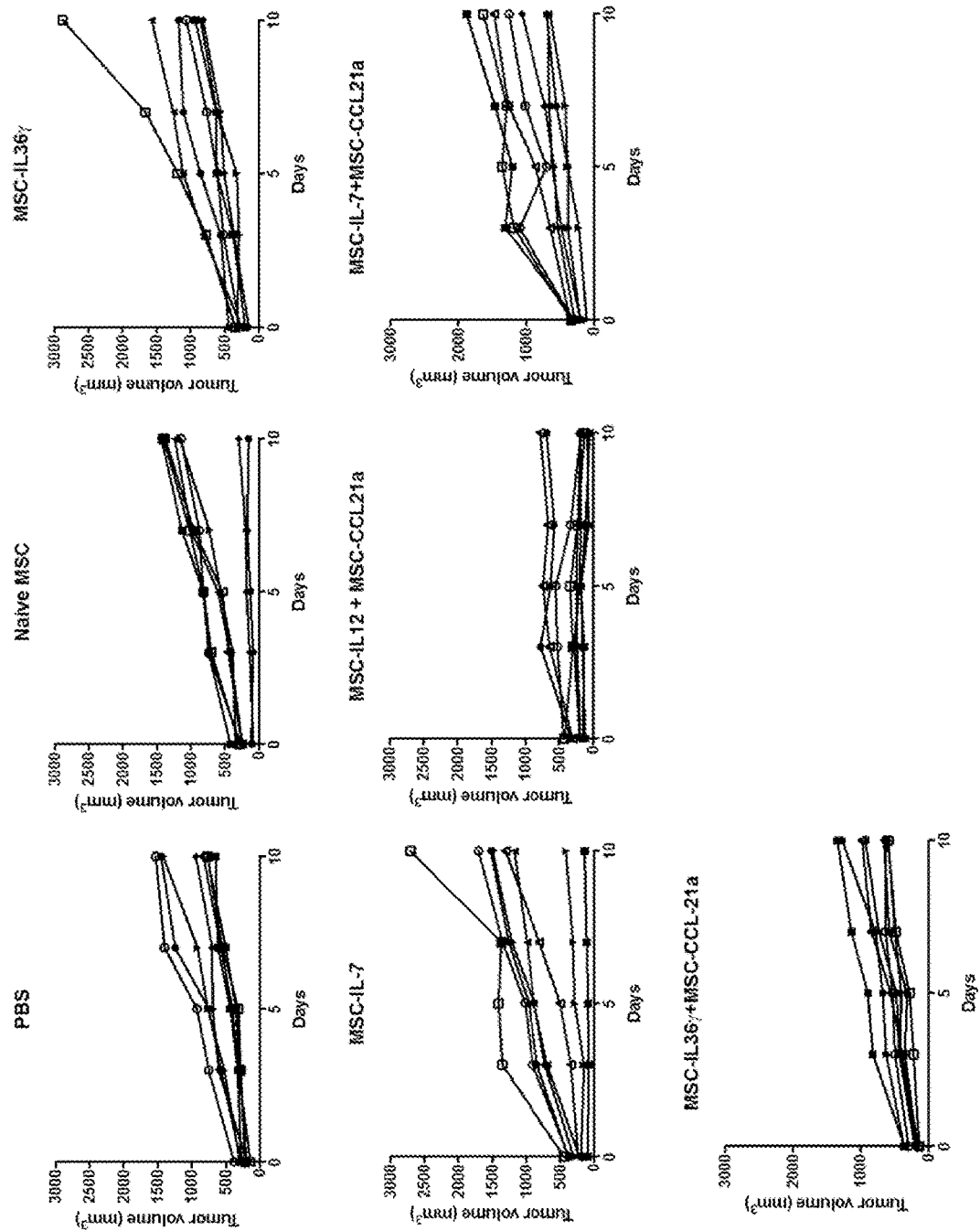
FIG. 22A includes data indicating that engineered MSCs expressing IL-12 and CCL21a inhibit tumor growth in a subcutaneous mouse model of colorectal cancer; however the combination of MSCs expressing CCL21a and IL-36 gamma or IL-7 does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 colon tumors in mice (n=6-8). Each line of FIG. 22A represents an individual mouse.
Figure 22B:
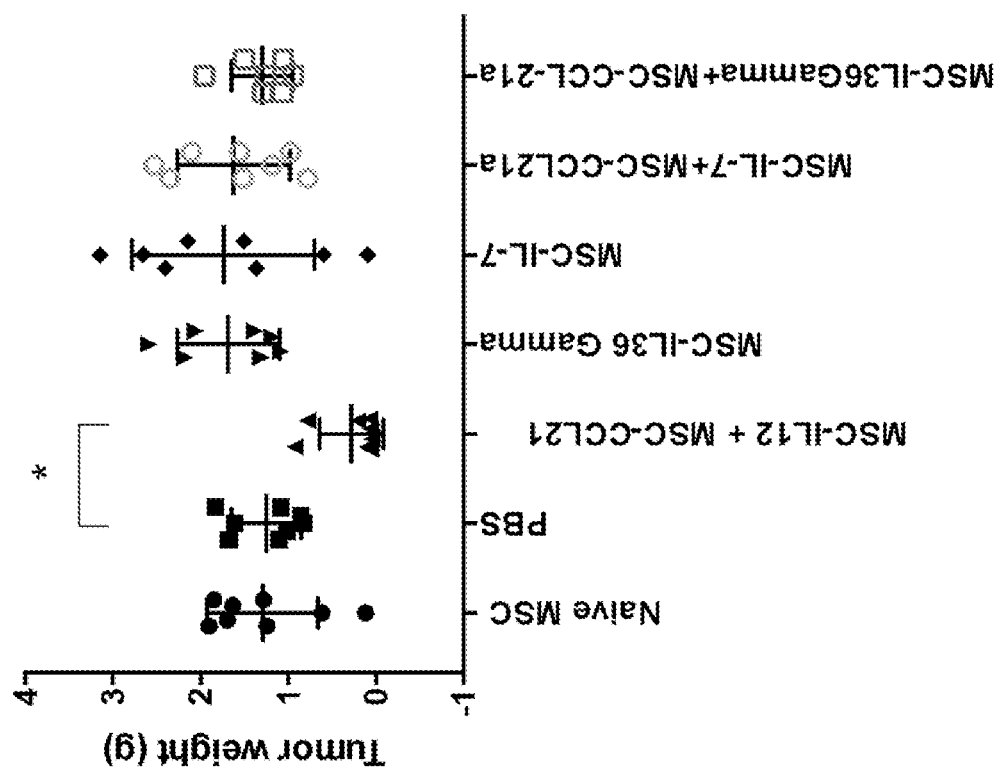
FIG. 22B shows the tumor weight for individual mice in each treatment group.
Figure 23A:
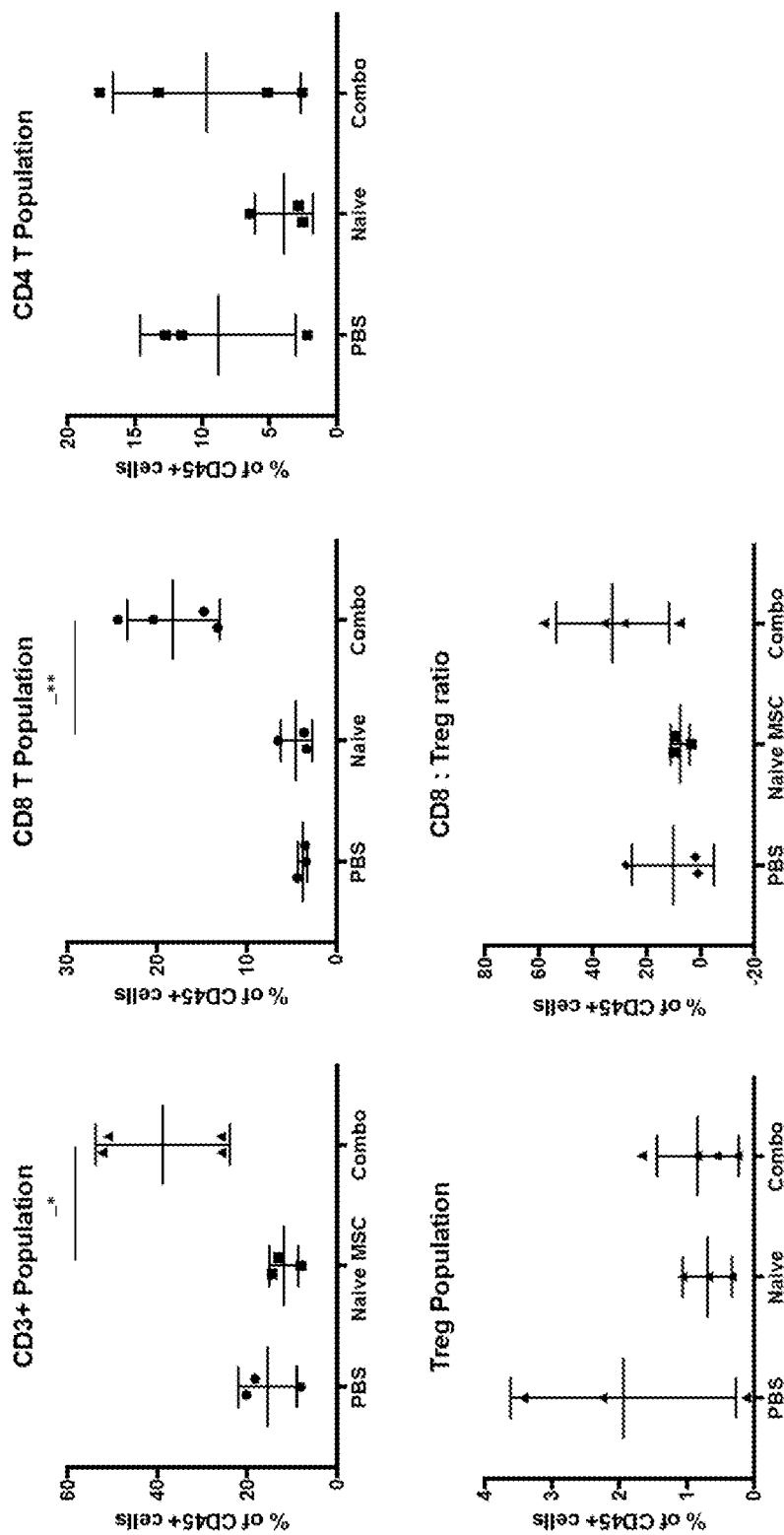
FIGS. 23A-23B include tumor immune infiltrate statistics from the experiment represented by FIGS. 22A-22B. Three mice were selected from PBS, Naïve MSC, and MSC-IL12+ MSC-CCL21a (combo) group to run flow cytometry to immune profile tumor microenvironment.
Figure 23B:
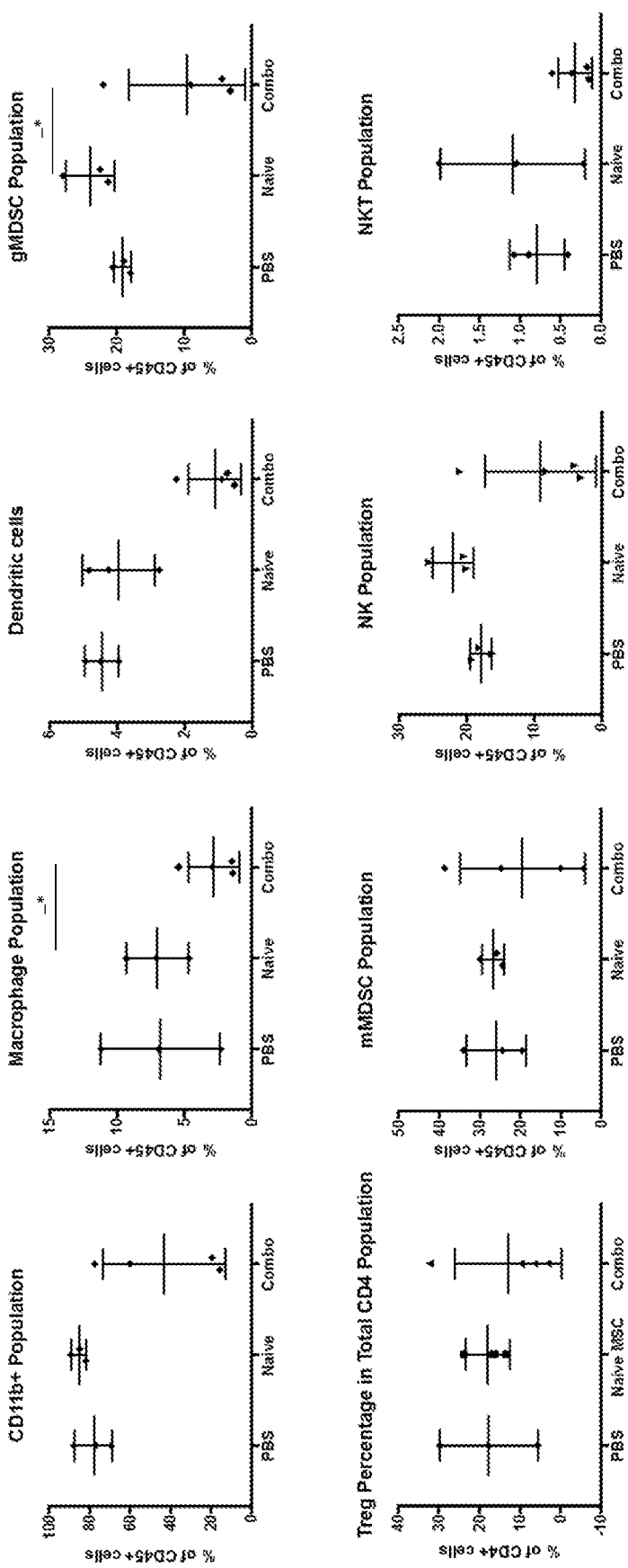

Tumor Infiltrate Statistics/Immune Percentage/Tumor Weight Subcutaneous Mouse Model FIG. 22A includes data indicating that engineered MSCs expressing IL-12 and CCL21a inhibit tumor growth in an subcutaneous mouse model of colorectal cancer; however the combination of MSCs expressing CCL21a and IL-36 gamma or IL-7 does not reduce tumor growth. FIGS. 23A-23B include the tumor immune infiltrate statistics. Three mice were selected from PBS, Naïve MSC, and MSC-IL12+MSC-CCL21a (combo) group to run flow cytometry to immune profile tumor microenvironment. FIG. 23A shows a significant increase in infiltrating CD3 and CD8 cytotoxic T population in the combo group compared to the group dosed with naïve MSC. FIG. 23B shows a significant reduction in granulocytic myeloid-derived suppressor cells (gMDSCs) and macrophage population in the combo group compared to group treated with Naïve MSC.

Figure 24A:
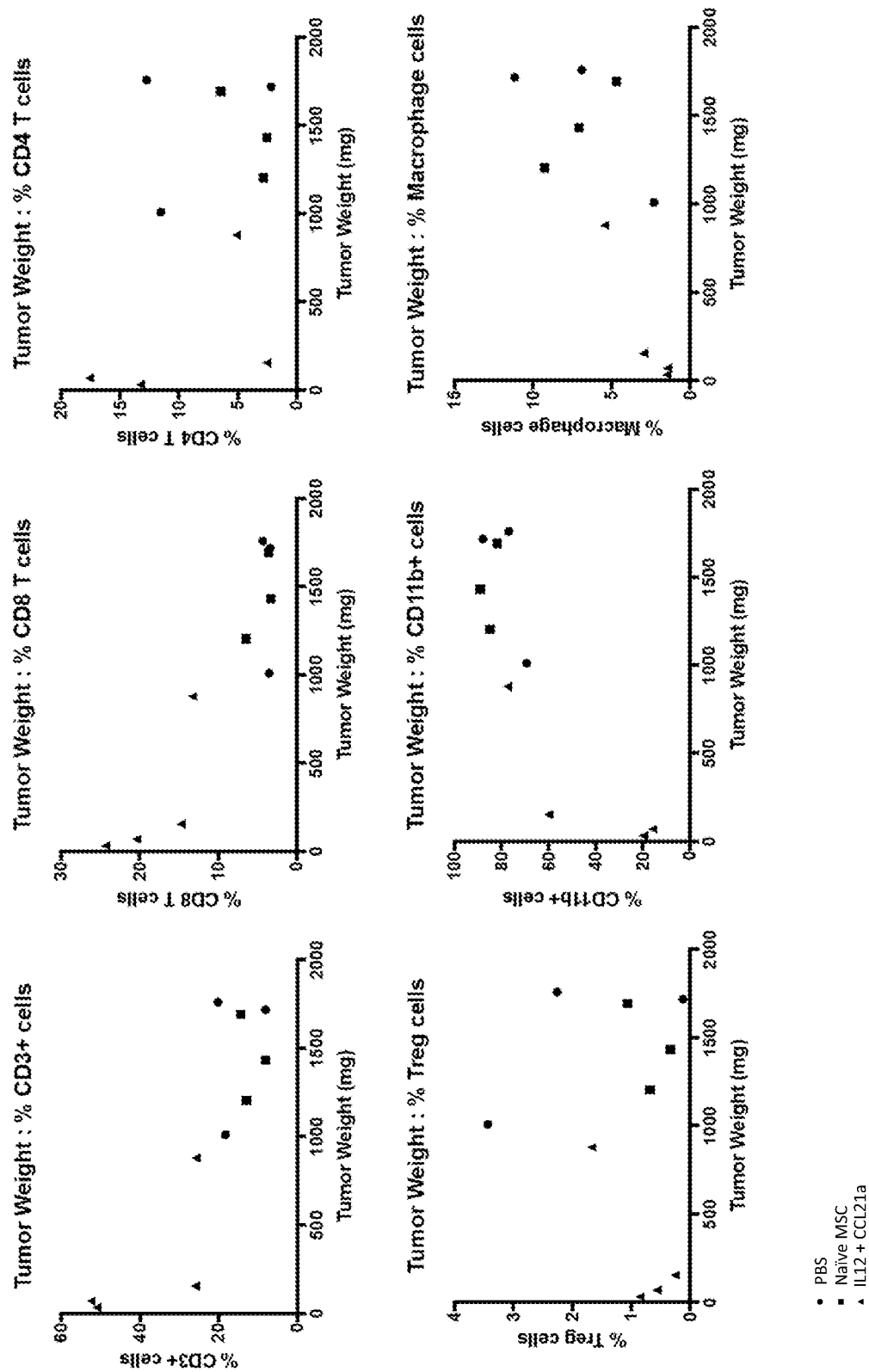
FIGS. 24A-24B include data relating to immune percentage and tumor weight, relating to the experiments represented by FIGS. 22A-22B.
Figure 24B:
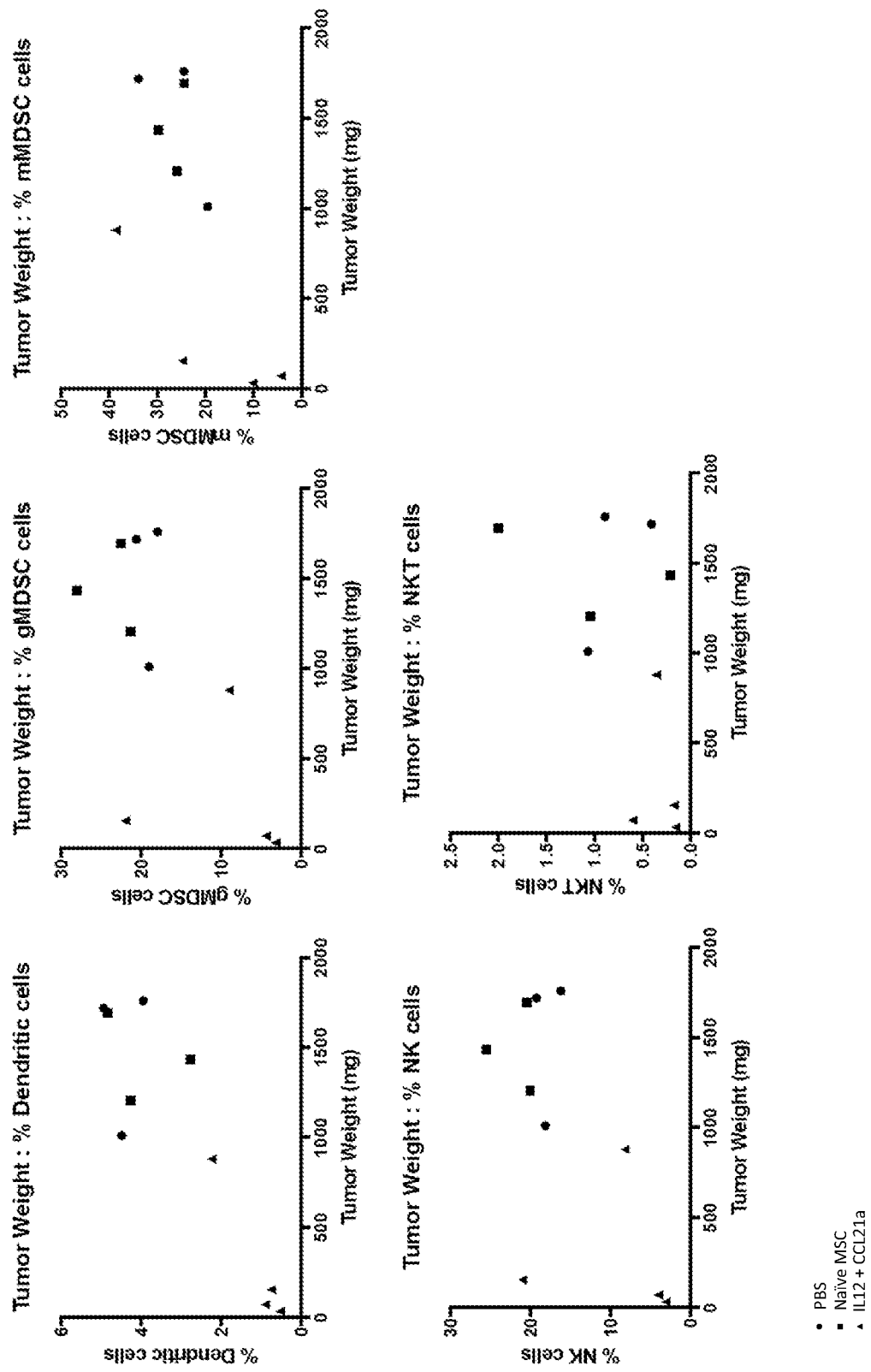

FIGS. 24A-24B include data relating to immune percentage and tumor weight, showing that samples with more CD3+ and CD8+ T cells (top left and center graph) correlate strongly with a decrease in tumor weight. These figures also show that samples with fewer CD11b myeloid cells, including macrophage, dendritic cells, and MDSC, display lower tumor burden (lower center and right graph of FIG. 24A and upper row of FIG. 24B).

Orthotopic Mouse Model

Figure 26A:
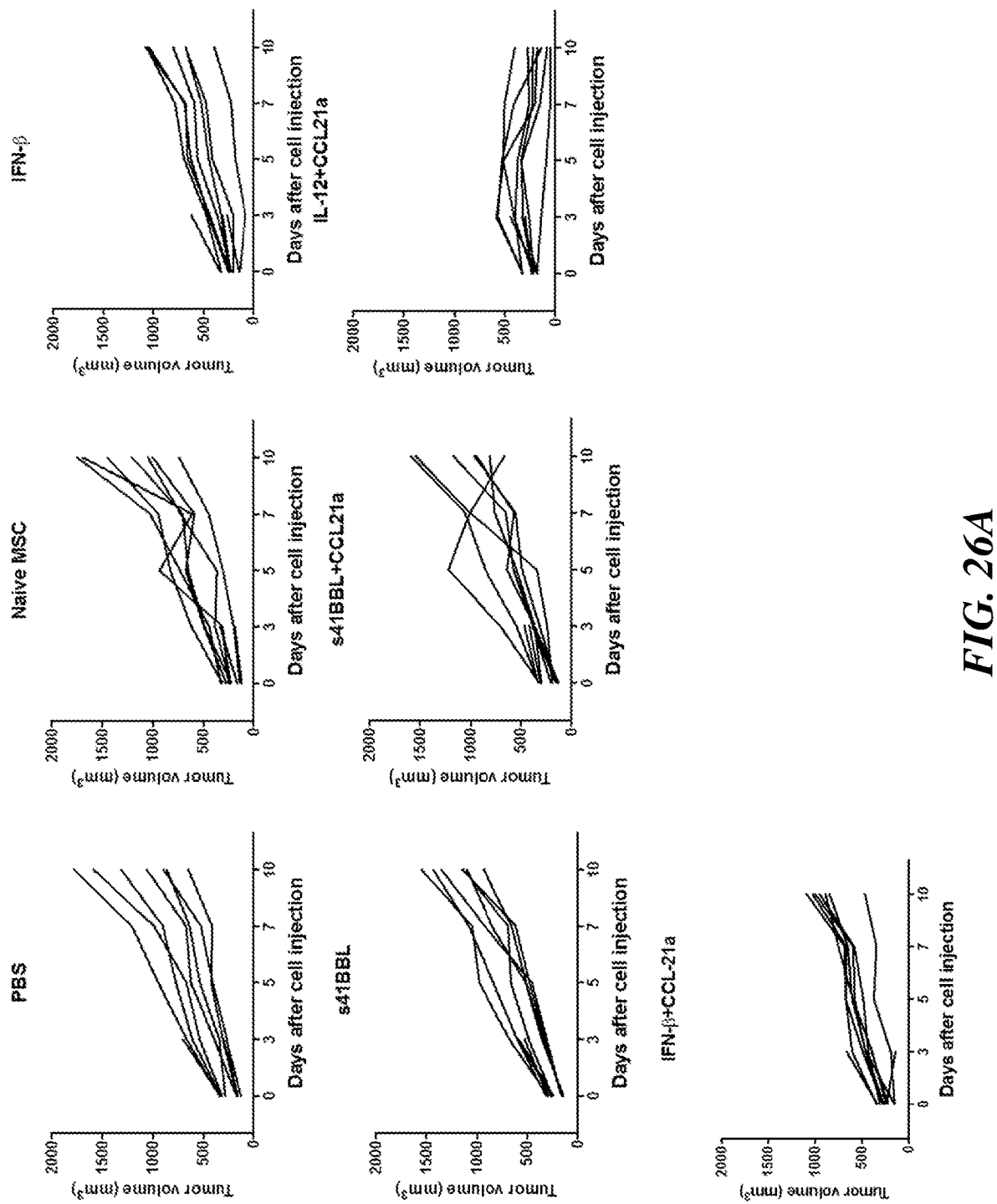
FIG. 26A includes data indicating that engineered combination treatment MSC-IL-12+MSC-CCL21a, or MSC-CCL21a+MSC-IFN-β, inhibit tumor growth in a subcutaneous mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 tumors in mice (n=6-8). Each line of FIG. 26A represents an individual mouse.
Figure 26B:
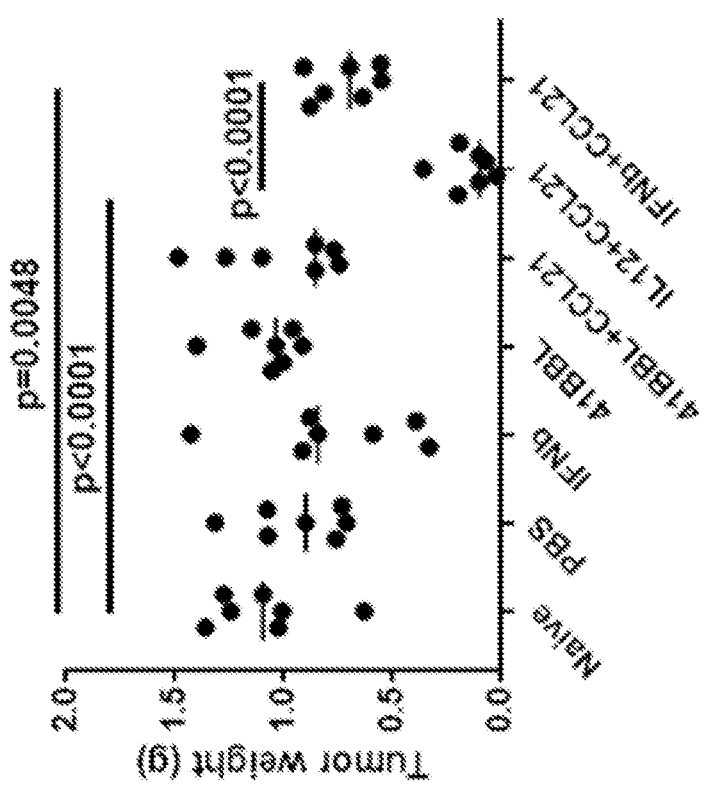

FIG. 26A shows that engineered MSCs expressing IL-12 and CCL21a, or CCL21a and IFN-β, inhibit tumor growth in an orthotopic mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 26A represents an individual mouse. FIG. 26B shows the tumor weight for individual mice in each treatment. MSC-IL12+ MSC-CCL21a shows best efficacy compared to mice injected with naïve MSC. Treatment efficacy was also observed in the group treated with MSC-IFNb+MSC-CCL21a.

Figure 27A:
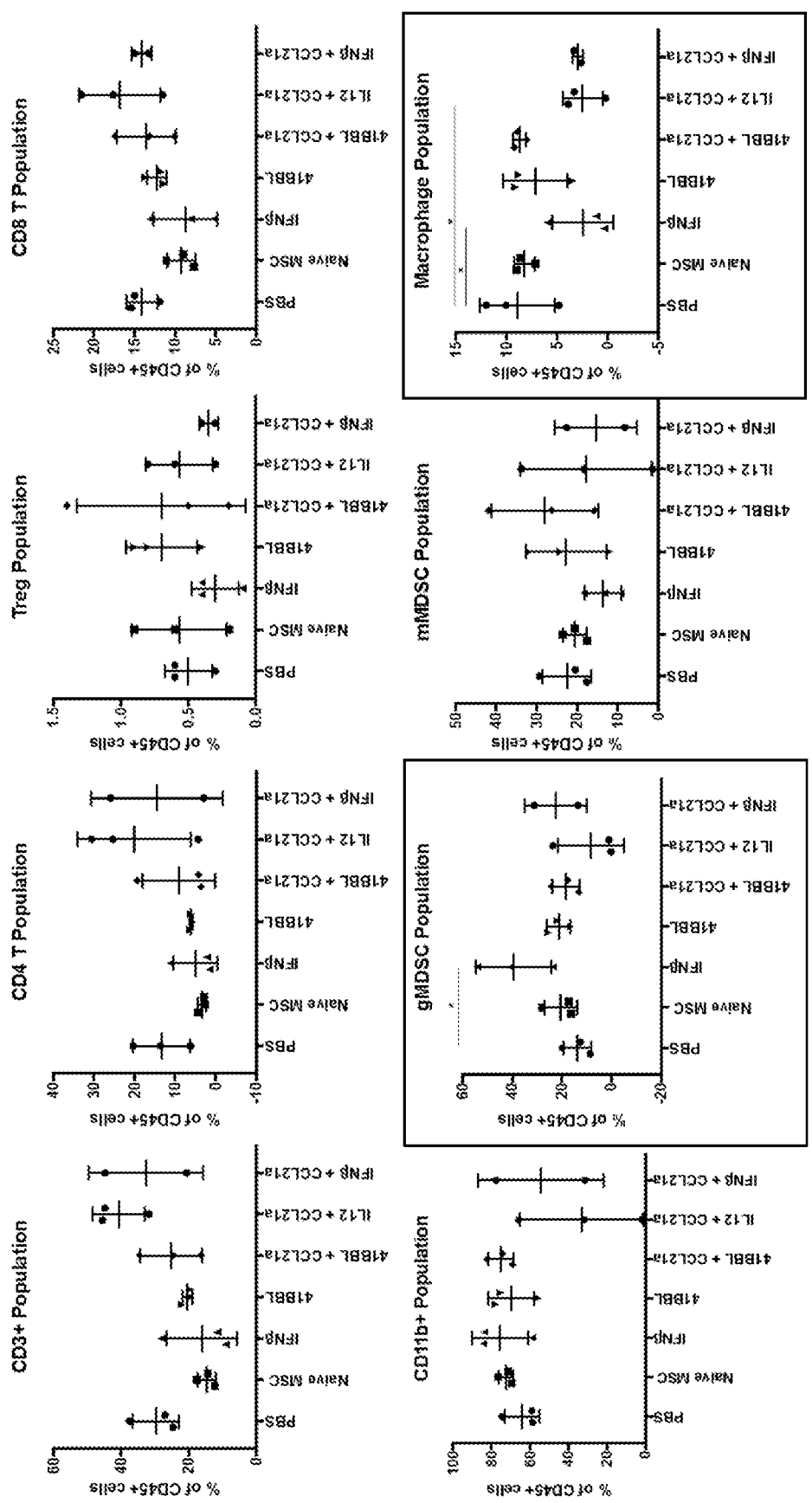
FIGS. 27A-27B provide additional data from the experiment represented by FIGS. 26A-26B.
Figure 27B:
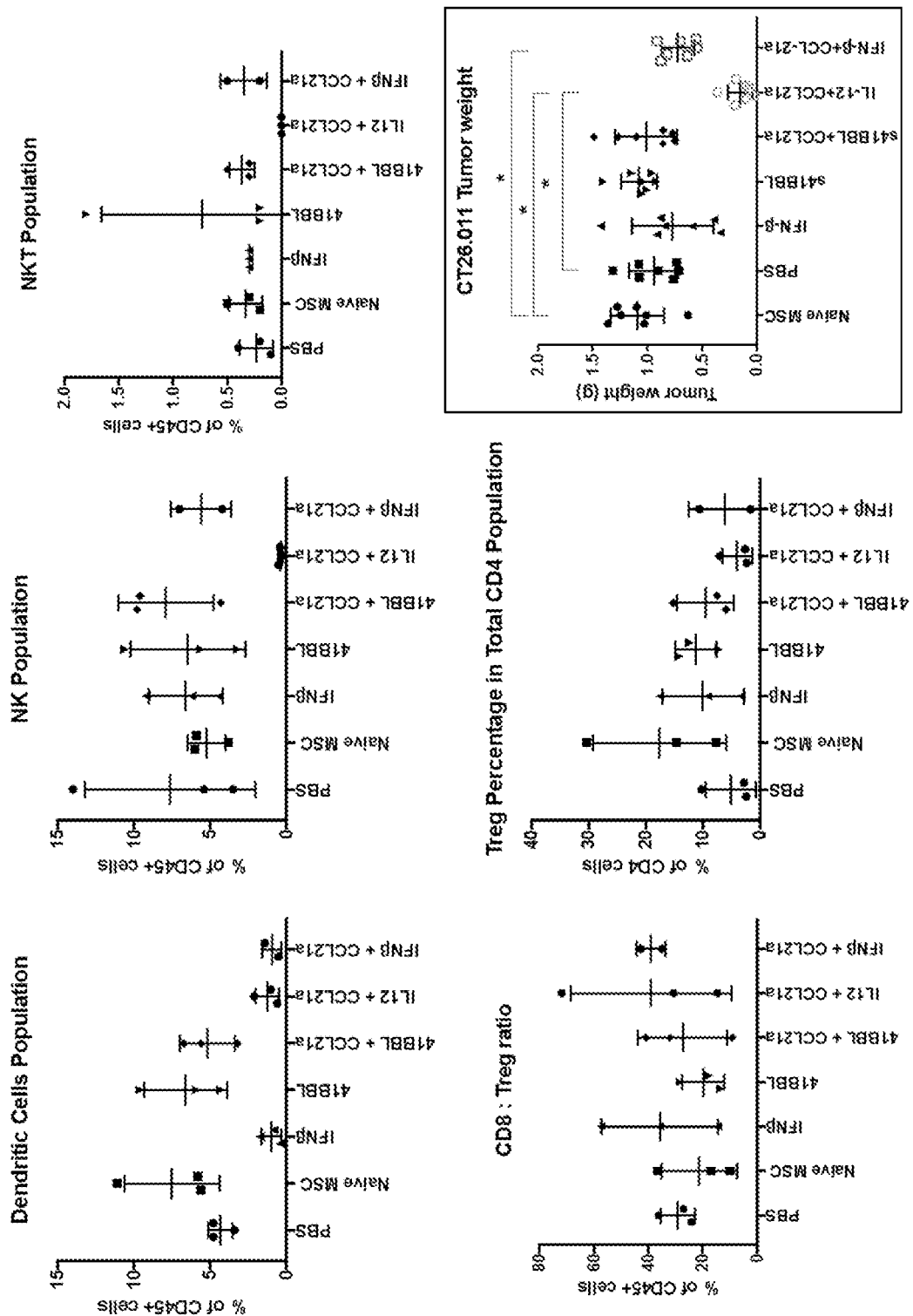

FIGS. 27A-27B are graphs that show immune profiles of each group treated with indicated engineered MSC. A consistent decrease in macrophage population was observed after treating with MSC-IL12+MSC-CCL21a (FIG. 27A). A general trend of increased infiltration in CD3+ population and decreased infiltration in CD11b+ population was also observed when compared to group treated with MSC-IL12+ MSC-CCL21a against naïve MSC (FIG. 27A and FIG. 27B).

Figure 28A:
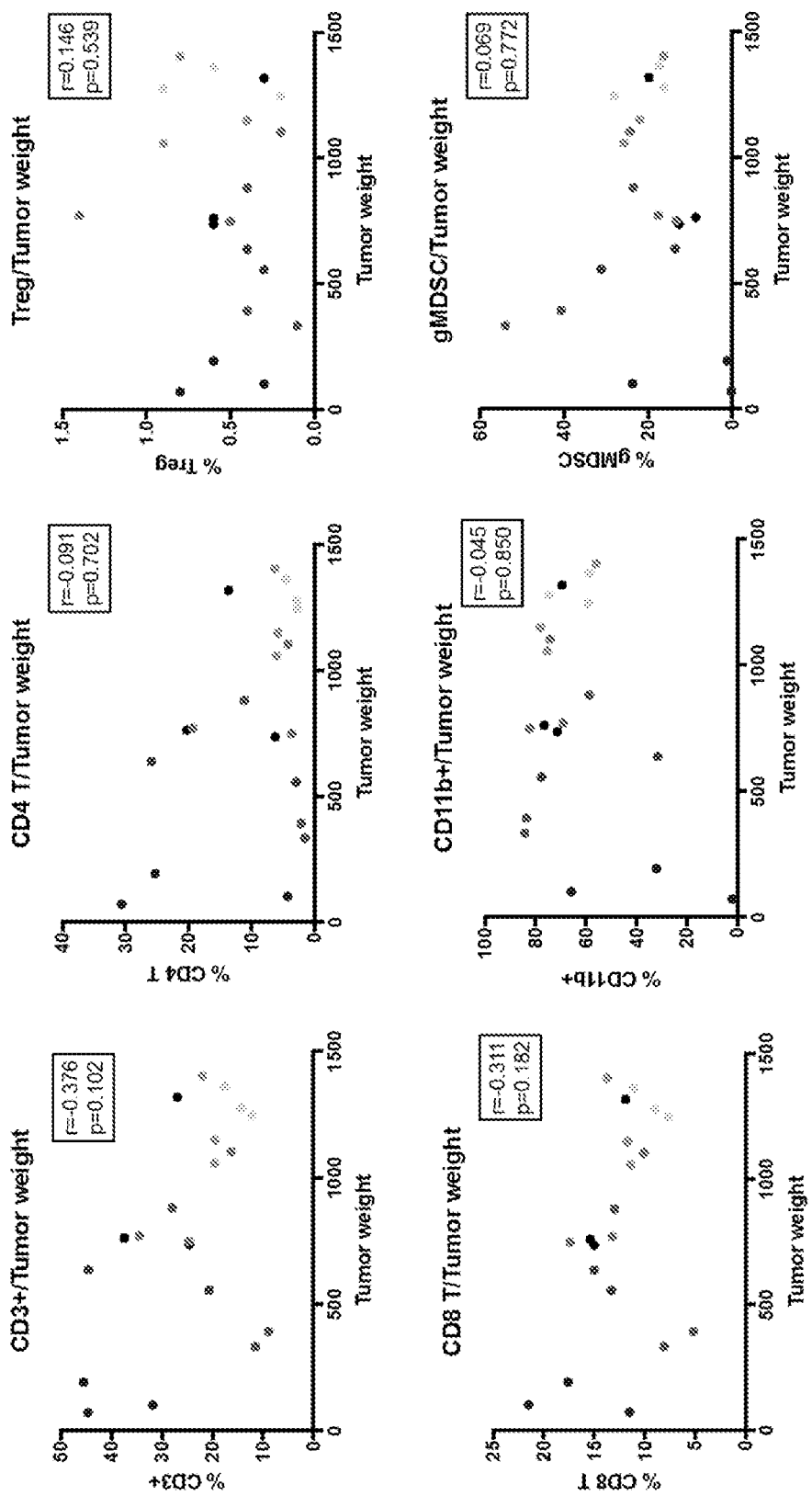
FIGS. 28A-28B also provide additional data from the experiment represented by FIGS. 26A-26B.
Figure 28B:
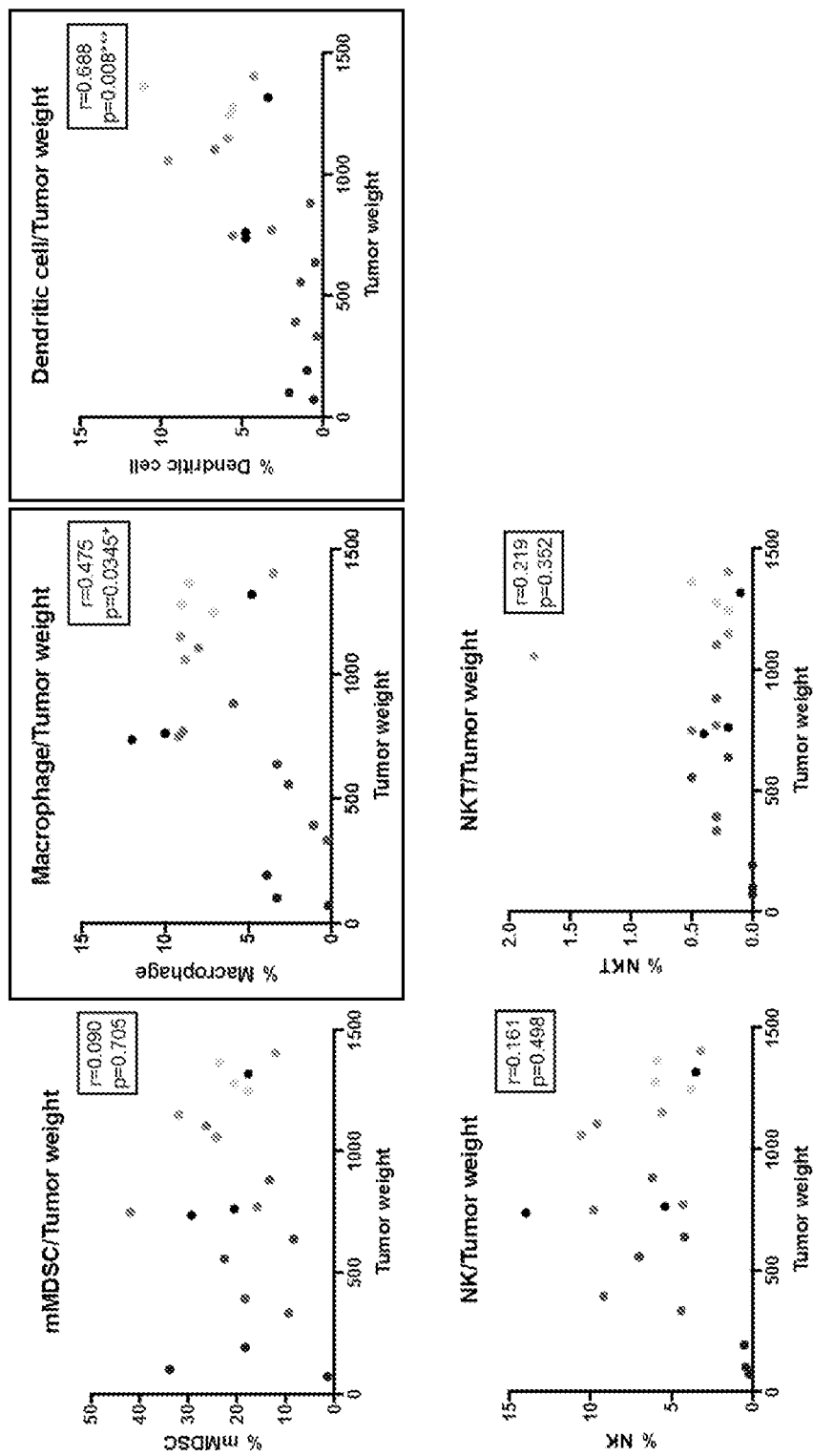

FIG. 28A-28B show the correlation of immune infiltration with tumor weight. Samples with low macrophage and dendritic cells have lower tumor burden (FIG. 28B, top center and top right). FIG. 28C shows the average tumor weight from each group. Statistical significance was observed with both MSC-IL12+MSC-CCL21a, or MSC-IFNb+MSC-CCL21a compared with naïve MSC.

Figure 29:
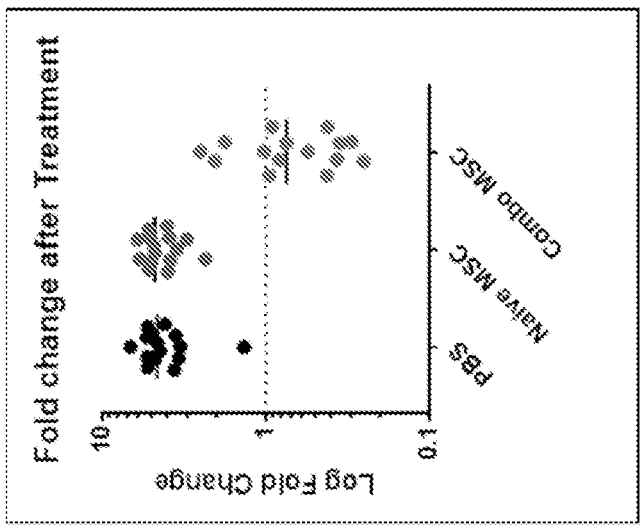
Figure 29:
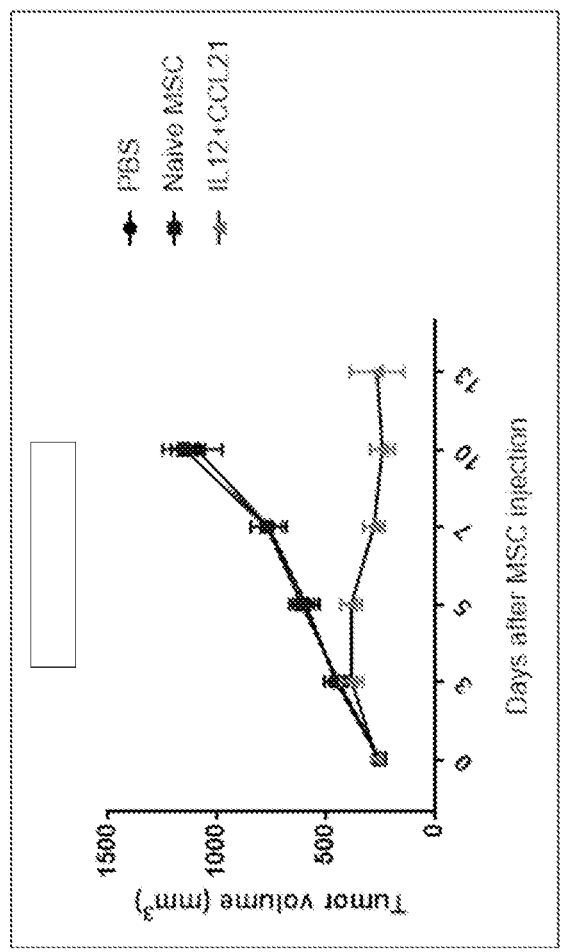

FIG. 29 shows graphs combining the in vivo data from the colorectal cancer models above (FIG. 22A and FIG. 26A). The combined CT26 data from FIG. 22A and FIG. 26A capture three groups: tumor only (PBS), treated with naïve MSC, and treated with MSC-IL12+MSC-CCL21a.

Figure 30A:
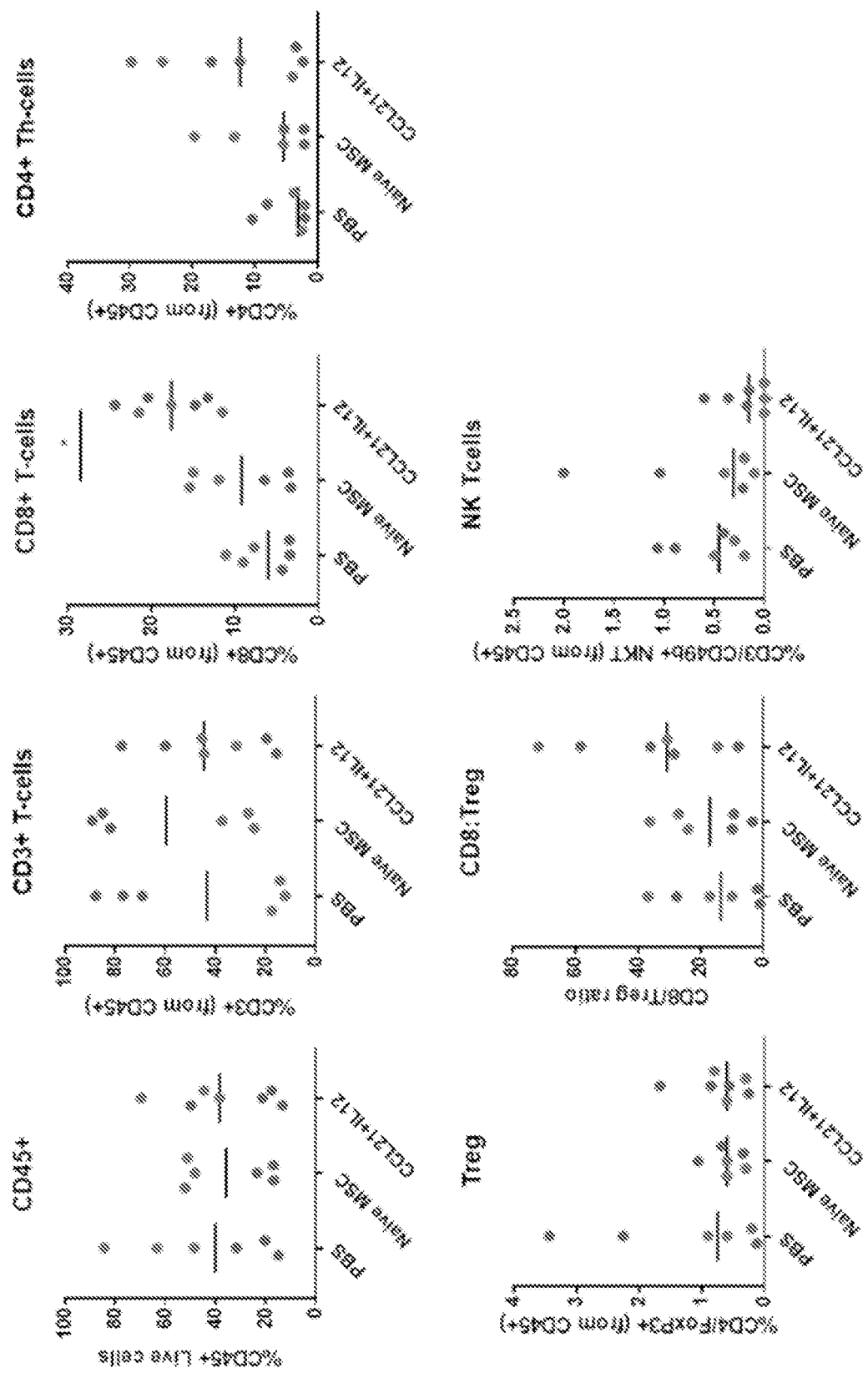
FIGS. 30A-30B also show combined data from FIG. 22A and FIG. 26A. The graphs show the average number of immune infiltration from the flow cytometry experiment data. Statistical significance was observed in CD8+T from FIG. 30A, demonstrating the ability of MSC-IL12+MSC-CCL21a to repolarize tumor microenvironment and allow more cytotoxic T cell infiltration. Furthermore, there was a reduction in CD11b+myeloid population infiltration in the groups that were treated by MSC-IL12+MSC-CCL21a (FIG. 30B). The data collected using dendritic cells and the macrophage population was statistical significance.
Figure 30B:
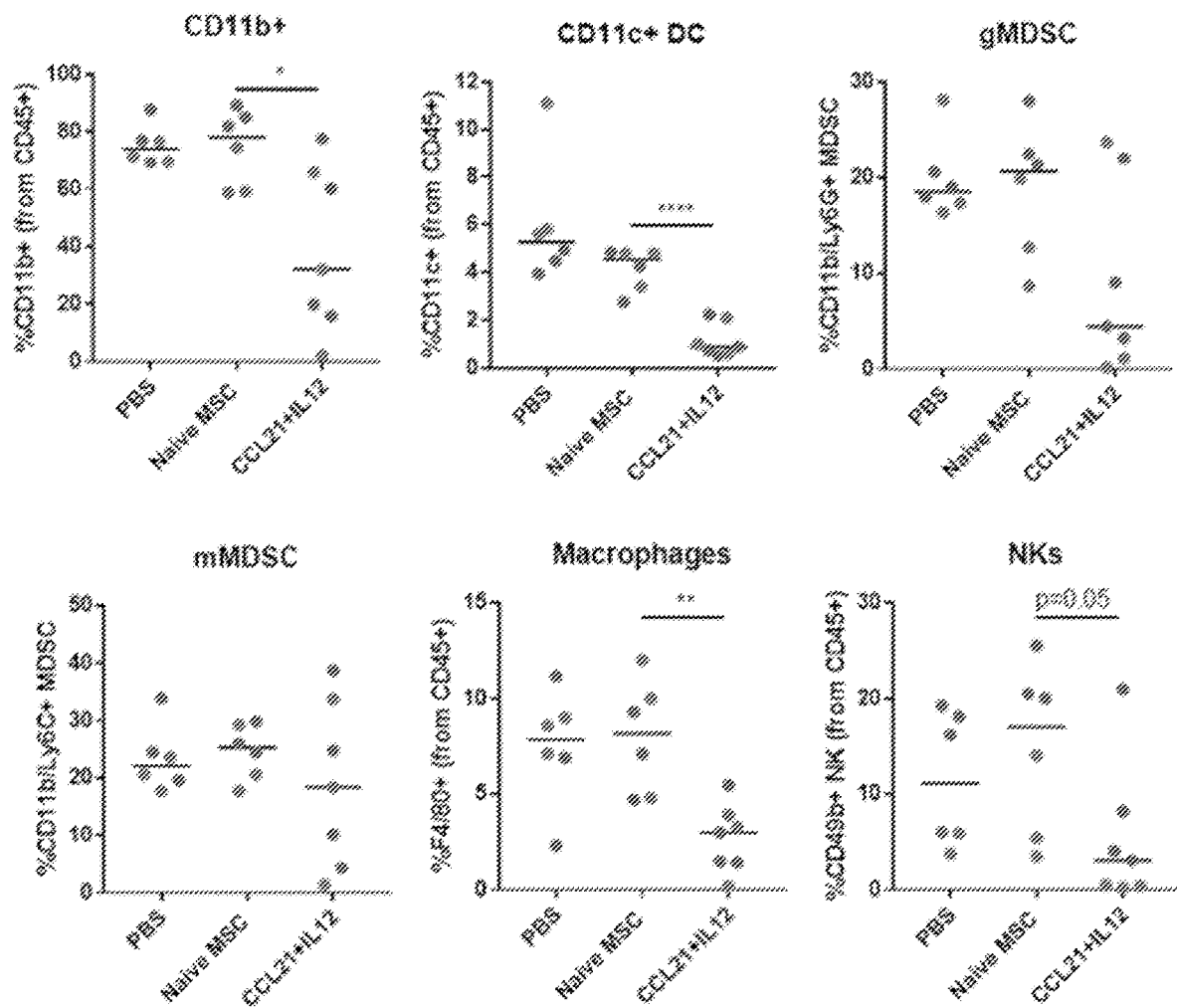

FIGS. 30A-30B also show combined data from FIG. 22A and FIG. 26A. The graphs show the average number of immune infiltration from the flow cytometry experiment data. Statistical significance was observed in CD8+T from FIG. 30A, demonstrating the ability of MSC-IL12+MSC-CCL21a to repolarize tumor microenvironment and allow more cytotoxic T cell infiltration. Furthermore, there was a reduction in CD11b+myeloid population infiltration in the groups that were treated by MSC-IL12+MSC-CCL21a (FIG. 30B). The data collected show that the dendritic cells and the macrophage population was statistical significance.

Figure 25A:
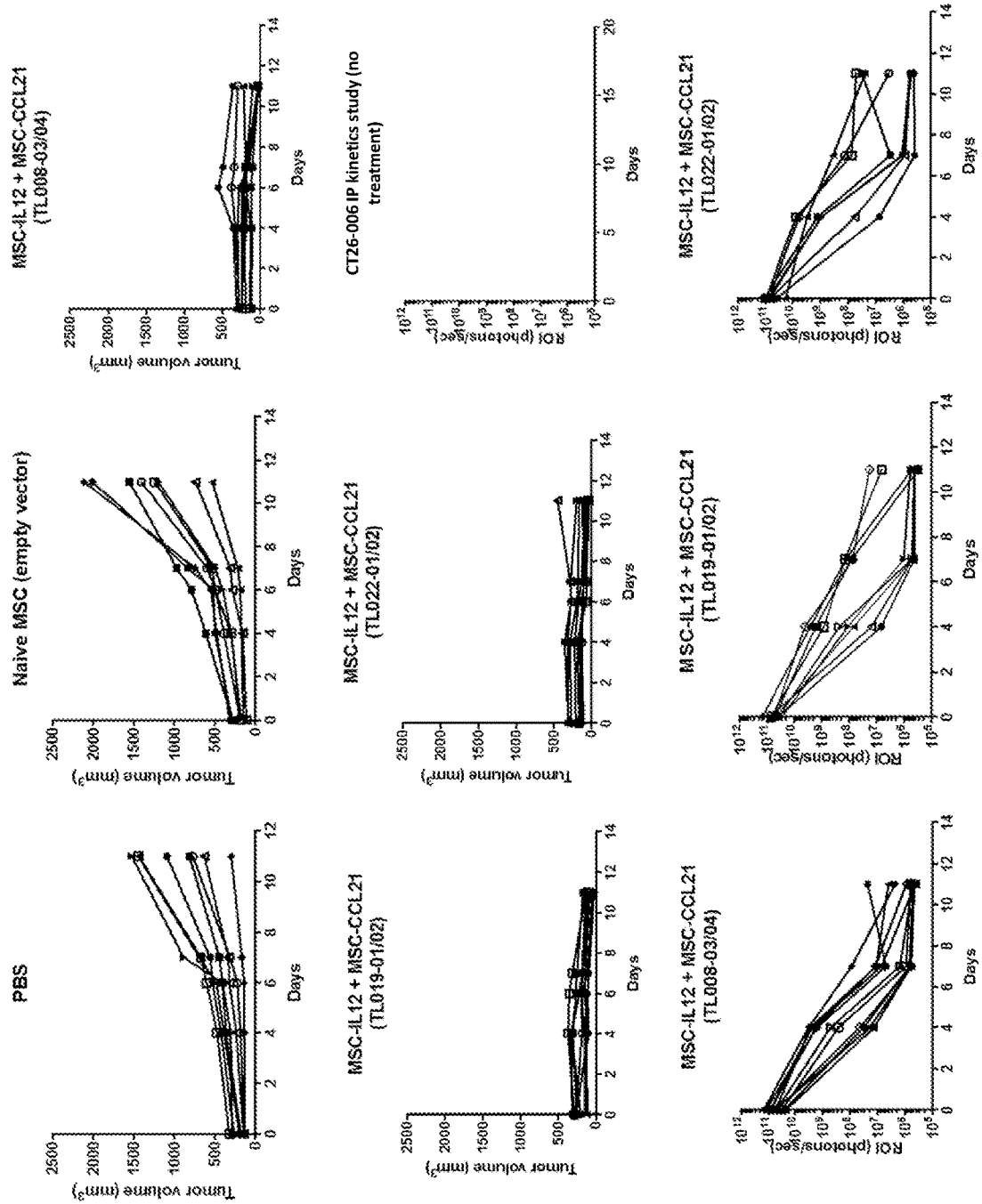
FIGS. 25A-25B include data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02; each TL number represents one lot).
Figure 25B:
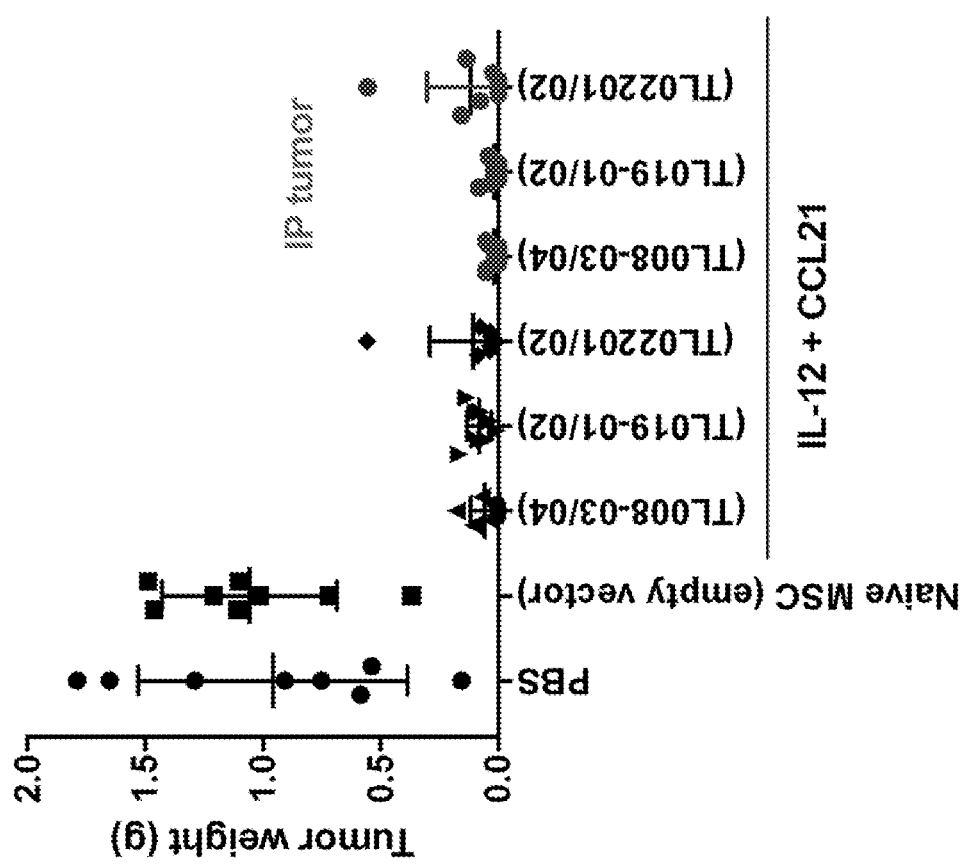

IL12 and CCL21a Therapy in Intraperitoneal and Subcutaneous Mouse Models of Colorectal Cancer FIGS. 25A-25B include data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02; each TL number represents one lot). FIG. 25A shows that all three lots of MSC-IL12+MSC-CCL21a can reduce tumor burden in both subcutaneous and intraperitoneal model (first 5 graphs are from the SC model and last 3 are from the IP model). Tumors from all mice were collected on day 11. FIG. 25B shows the average tumor weight from each group.

REFERENCES

1. Kidd S, et al. (2009) Stem Cells 27(10):2614-2623.
2. Dembinski J L, et al. (2013) Cytotherapy 15(1):20-32.
3. Siegel R L, et al. (2016) CA Cancer J Clin 66(1):7-30.
4. Dizon D M J (2010) Gynecol Oncol 116(3).
5. Woo S R, et al. (2015) Trends Immunol 36(4):250-256.
6. Hamanishi J, et al. (2016) Int Immunol 28(7):339-348.
7. Li S, et al. (2012) Oncolytic Virother 1:1-21.
8. Koneru M, et al. (2015) J Transl Med 13:102.
9. Cruz C R, et al. (2010) Cytotherapy 12(6):743-749.
10. Li Y Q, et al. (2013) PLoS One 8(10):e76379.
11. Wiedemann G M, et al. (2016) Oncoimmunology 5(9): e1175794.
12. Squillaro T, et al. (2016) Cell Transplant 25(5):829-848.
13. Studeny M, et al. (2004) J Natl Cancer Inst 96(21):1593-1603.
14. Ling X, et al. (2010) Cancer Microenviron 3(1):83-95.
15. Schukur L, et al. (2015) Sci Transl Med 7(318): 318ra201.
16. Howlader N N A, Krapcho M, Garshell J, Miller D, Altekruse S F, Kosary C L, Yu M, Ruhl J, Tatalovich Z, Mariotto A, Lewis D R, Chen H S, Feuer E J and Cronin K A. (2015).
17. Lengyel E (2010) Am J Pathol 177(3):1053-1064.
18. McGuire W P, et al. (1996) The New England journal of medicine 334(1):1-6.
19. McGuire W P, et al. (1989) Annals of internal medicine 111(4):273-279.
20. Adams S F & Benencia F (2015) Future Oncology 11(9):1293-1296.
21. Maude S L, et al. (2014) N Engl J Med 371(16):1507-1517.
22. Bargou R, et al. (2008) Science 321(5891):974-977.
23. Kershaw M H, et al. (2014) Clin Trans Immunol 3:e16.
24. Gilham D E, et al. (2012) Trends Mol Med 18(7):377-384.
25. Klinger M, et al. (2012) Blood 119(26):6226-6233.
26. Fu J, et al. (2015) Sci Transl Med 7(283):283ra252.
27. Moynihan K D, et al. (2016) Nat Med 22(12):1402-1410.
28. Mohammadi M, et al. (2016) Cancer Gene Ther 23(9): 285-286.
29. Wang D, et al. (2013) Cell Transplant 22(12):2267-2277.
30. Nowakowski A, et al. (2016) Stem Cells Int 2016: 4956063.
31. Sun Z, et al. (2014) J Hematol Oncol 7:14.
32. Ando M, et al. (2015) Stem Cell Reports 5(4):597-608.
33. Zhao Q, et al. (2015) Proc Natl Acad Sci USA 112(2): 530-535.
34. Xie C, et al. (2013) Br J Cancer 109(5):1198-1205.
35. Parker B S, et al. (2016) Nat Rev Cancer 16(3):131-144.
36. Roby K F, et al. (2000) Carcinogenesis 21(4):585-591.
37. Sharma A D, et al. (2015) J Vis Exp (95):e52242.
38. Waterman R S, et al. (2012) PLoS One 7(9):e45590.
39. Dubinett S M, et al. (2010) Cancer J 16(4):325-335.
40. Tang E D & Wang C Y (2015) PLoS One 10(3): e0120090.
41. Cieri N, et al. (2013) Blood 121(4):573-584.
42. Fitzgerald K A, et al. (2003) Nat Immunol 4(5):491-496.
43. Wong A S, et al. (2016) Proc Natl Acad Sci USA 113(9):2544-2549.
44. Wong A S, et al. (2015) Nat Biotechnol 33(9):952-961.
45. Nissim L, et al. (2014) Mol Cell 54(4):698-710.
46. Deng P, et al. (2016) Neural Regen Res 11(5):702-705.
47. Beegle J R, et al. (2016) Mol Ther Methods Clin Dev 3:16053.
48. Boutros C, et al. (2016) Nat Rev Clin Oncol 13(8):473-486.
49. Valsecchi M E (2015) New Engl J Med 373(13):1270-1270.
50. Pardoll D M (2012) Nat Rev Cancer 12(4):252-264.
51. Legat A, et al. (2013) Front Immunol 4:455.
52. Justus C R, et al. (2014) J Vis Exp (88).
53. Jedema I, et al. (2004) Blood 103(7):2677-2682.
54. Peng D, et al. (2015) Nature 527(7577):249-253.
55. Gitzinger M, et al. (2009) Proc Natl Acad Sci USA 106(26):10638-10643.

56. Clackson T, et al. (1998) Proc Natl Acad Sci USA 95(18):10437-10442.
57. Siuti P, et al. (2013) Nature Biotechnology 31(5):448-452.
58. Farzadfard F & Lu T K (2014) Science 346(6211): 1256272.
59. Perli S D, et al. (2016) Science 353(6304).
60. Roquet N, et al. (2016) Science 353(6297):aad8559.
61. Wong A S L, et al. (2016) Proceedings of the National Academy of Sciences.
62. Gardner T S, et al. (2000) Nature 403(6767):339-342.
63. Deans T L, et al. (2007) Cell 130(2):363-372.
64. Warren L, et al. (2010) Cell Stem Cell 7(5):618-630.
65. Yang B X, et al. (2015) Cell 163(1):230-245.
66. Kumar R M, et al. (2014) Nature 516(7529):56-61.
67. Zhang J, et al. (2016) Cell Stem Cell 19(1):66-80.
68. Cahan P, et al. (2014) Cell 158(4):903-915.
69. Doulatov S, et al. (2013) Cell Stem Cell 13(4):459-470.
70. Kim K, et al. (2011) Nat Biotechnol 29(12):1117-1119.
71. Chavez A, et al. (2016) Nat Methods 13(7):563-567.
72. Slomovic S & Collins J J (2015) Nat Methods 12(11): 1085-1090.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of reducing tumor volume in a subject, the method comprising delivering to a subject having a tumor a composition comprising mesenchymal stem cells engineered to produce multiple effector molecules comprising at least a first effector molecule and a second effector molecule that each modulate tumor-mediated immunosuppressive mechanisms in an effective amount to reduce the volume of the tumor, wherein the first effector molecule comprises interleukin 12 (IL-12),
  wherein the multiple effector molecules except the first effector molecule are each independently selected from the group consisting of: cytokines, receptors/ligands, antibodies, nucleotides, peptides, and enzymes,
  wherein the composition comprises (a) a first mesenchymal stem cell engineered to produce the first effector molecule and (b) a second mesenchymal stem cell engineered to produce the second effector molecule, and
  wherein tumor reduction is greater than tumor reduction following administration of either the first mesenchymal stem cell alone or the second mesenchymal stem cell alone.

2. The method of claim 1, wherein the tumor is selected from the group consisting of: bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and uterine tumors.

3. The method of claim 1, wherein the second effector molecule is selected from the group consisting of: MIP1a (CCL3), MIP1b (CCL5), CCL21, CXCL9, CXCL10 CXCL11, IFN-β, IFN-γ, IL-2, IL-4, IL-15, IL-16, IL-7, IL-9, IL-36y, IL-18, IL-21, IL-1β, OX40-ligand, CD40L, an anti-PD-1 antibody, an anti-PD-L1 antibody, an anti-CTLA-4 antibody, CCR9, CXCR3, CXCR4, CCR2, CCR4, FPR2, VEGFR, IL6R, CXCR1, CSCR7, and PDGFR.

4. The method of claim 1, wherein the method further comprises delivering to the subject a checkpoint inhibitor.

5. The method of claim 4, wherein the checkpoint inhibitor is an anti-PD-1 antibody, an anti-PD-1L antibody, or an anti-CTLA-4 antibody.

6. The method of claim 4, wherein the checkpoint inhibitor is an anti-CTLA-4 antibody.

7. The method of claim 1, wherein the method further comprises delivering to the subject an anti-CD40 antibody.

8. The method of claim 1, wherein the volume of the tumor is reduced by at least 25% relative to a control.

9. The method of claim 1, wherein the second effector molecule comprises IL-21.

10. The method of claim 1, wherein the composition is administered intraperitoneally.

11. The method of claim 1, wherein the tumor is an ovarian tumor.

12. A method of modulating an immunosuppressive mechanism in a subject, the method comprising delivering to a subject a composition comprising mesenchymal stem cells engineered to produce multiple effector molecules comprising at least a first effector molecule and a second effector molecule that each modulate tumor-mediated immunosuppressive mechanisms in an effective amount to modulate the immunosuppressive mechanism, wherein the first effector molecule comprises IL-12,
  wherein modulating the immunosuppressive mechanism comprises increasing an immune response in the subject,
  wherein the multiple effector molecules except the first effector molecule are each independently selected from the group consisting of: cytokines, receptors/ligands, antibodies, nucleotides, peptides, and enzymes,
  wherein the composition comprises (a) a first mesenchymal stem cell engineered to produce the first effector molecule and (b) a second mesenchymal stem cell engineered to produce the second effector molecule, and
  wherein the increased immune response is greater than the immune response following administration of either the first mesenchymal stem cell alone or the second mesenchymal stem cell alone.

13. The method of claim 12, wherein the subject has a tumor selected from the group consisting of: bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and uterine tumors.

14. The method of claim 12, wherein the subject has an ovarian tumor.

15. The method of claim 12, wherein the second effector molecule comprises IL-21.

16. The method of claim 12, wherein the composition is administered intraperitoneally.

17. The method of claim 1, wherein the tumor reduction is equal to or greater than the sum of the tumor reduction following separate administration of the first mesenchymal stem cell and the second mesenchymal stem cell.

18. The method of claim 12, wherein the tumor reduction is equal to or greater than the sum of the tumor reduction following separate administration of the first mesenchymal stem cell and the second mesenchymal stem cell.

* * * * *